United States Patent
Ma

(10) Patent No.: US 11,801,302 B2
(45) Date of Patent: *Oct. 31, 2023

(54) FORMULATIONS AND USES THEREOF

(71) Applicant: Joyce H. Ma, Redding, CA (US)

(72) Inventor: Joyce H. Ma, Redding, CA (US)

(*) Notice: Subject to any disclaimer, the term of this patent is extended or adjusted under 35 U.S.C. 154(b) by 227 days.

This patent is subject to a terminal disclaimer.

(21) Appl. No.: 17/186,548

(22) Filed: Feb. 26, 2021

(65) Prior Publication Data

US 2021/0268110 A1 Sep. 2, 2021

Related U.S. Application Data

(60) Provisional application No. 62/982,918, filed on Feb. 28, 2020.

(51) Int. Cl.
  *A61K 47/14* (2017.01)
  *A61K 45/06* (2006.01)
  *A61K 47/02* (2006.01)
  *A61K 47/44* (2017.01)

(52) U.S. Cl.
  CPC .............. *A61K 47/14* (2013.01); *A61K 45/06* (2013.01); *A61K 47/02* (2013.01); *A61K 47/44* (2013.01)

(58) Field of Classification Search
  CPC ......... A61K 47/02; A61K 47/14; A61K 41/44
  See application file for complete search history.

(56) References Cited

U.S. PATENT DOCUMENTS

| | | |
|---|---|---|
| 6,280,751 B1 | 8/2001 | Fletcher et al. |
| 9,566,306 B2 | 2/2017 | Zemtsov |
| 9,757,324 B2 | 9/2017 | Weisenfluh et al. |
| 2004/0185115 A1 | 9/2004 | Pearson et al. |
| 2005/0123619 A1 | 6/2005 | Farrell |
| 2006/0229222 A1 | 10/2006 | Muller et al. |
| 2009/0186094 A1 | 7/2009 | Bahney |
| 2011/0144142 A1 | 6/2011 | Hu et al. |
| 2012/0171186 A1 | 7/2012 | Liang |
| 2012/0328549 A1 | 12/2012 | Edelson et al. |
| 2013/0171078 A1 | 7/2013 | Lawson |
| 2017/0360073 A1 | 12/2017 | Vadakkemuri |
| 2019/0053996 A1 | 2/2019 | Collier et al. |
| 2020/0000693 A1 | 1/2020 | Traynor et al. |

FOREIGN PATENT DOCUMENTS

WO WO 2013/186108 A2 12/2013

OTHER PUBLICATIONS

Wertz, "Lipids and the Permeability and Antimicrobial Barriers of the Skin", Journal of Lipids, vol. 2018, pp. 1-7 (2018).*
K. Warner et al. "Frying Stability of Soybean and Canola Oils with Modified Fatty Acid Compositions" Food Quality and Safety Research; JAOCS, vol. 70, No. 10 (Oct. 1993); pp. 983-988.
International Search Report dated May 6, 2021, in connection with corresponding International Application No. PCT/US21/19821.
Written Opinion of the International Searching Authority dated May 6, 2021, in connection with corresponding International Application No. PC/US21/19821.

\* cited by examiner

*Primary Examiner* — Kevin E Weddington
(74) *Attorney, Agent, or Firm* — Davidson, Davidson & Kappel, LLC

(57) ABSTRACT

Preparations and formulations capable of crossing and incorporating into a membrane of a cell or an organelle or an exosome are described. Methods of treatments utilizing the preparations and formulations are also described.

27 Claims, 14 Drawing Sheets

Scanning Electron Microscopy Image of Unloaded Diatom (1.2 – 180 um)

Schematic of Unloaded Diatom With Many Open Pores

FORMULATIONS AND USES THEREOF

This application claims the benefit of U.S. Provisional Application No. 62/982,918, filed on Feb. 28, 2020, hereby incorporated by reference.

BACKGROUND OF THE INVENTION

Healthy cell membranes serve as a barrier to the environment outside of the cell. They also serve as a hub, filtering and interpreting signals from the cell's surroundings and translating external signals into a cellular response by directing changes in gene expression. Healthy cell membranes also send, receive, and coordinate signals to and from other cells, and can elicit responses in cells close by, or even in cells at the opposite end of the body.

The modern Western diet filled with processed foods rich in ω6 rather than ω3 fats (in combination with other factors of modern life such as the ubiquitous use of plastics, pesticides, synthetic food additives) may alter membrane compositions and lead to changes in many physical parameters of a cell membrane such as membrane fluidity, permeability, and may interfere with the ability of intramembrane proteins and structures to interact (Phillips R., Membranes by the Numbers arxiv.org 6 Mar. 2017). These changes may contribute to the development of many chronic diseases, especially in patients with genetic predispositions for specific illnesses.

Many disease states are driven by imbalances of lipids and phospholipids in cell membranes and impairments in cell membrane composition and functions. Disturbances in cell membrane function may manifest as dysregulated growth and proliferation (leading to diseases such as cancer, keloids, or psoriasis, among others); as a disrupted skin barrier (leading, for example, to eczema or a non-healing wound); as hormone dysregulation such as, for example, in diabetes, hyperlipidemia, and metabolic syndrome; as poor immune function; or as disrupted neuronal signaling such as, for example, in multiple sclerosis and Alzheimer's Disease.

One of the possible manifestations of impairments in cell membrane function is a decreased tolerance to pain and an increased predisposition to inflammation. Pain is defined as a sensation related to potential or actual damage in a bodily tissue (PMID 25722692). Pain is a multifaceted experience for the patient, involving both a physical response in the damaged structures or tissues (inflammation, swelling, increased muscle tension, and physical sensitization) as well as a secondary emotional response to the pain itself (anger, frustration, anxiety, insomnia, and emotional sensitization). Of note, insomnia further decreases global pain tolerance, worsens inflammation, and increases abnormal muscle tension, pain and swelling, thus perpetuating a negative feed-forward cycle of pain.

Current oral and topical solutions for the treatment of pain for the most part only temporarily address some and not all aspects and not the root cause of pain. For example, non-steroidal anti-inflammatory drugs (NSAIDs) inhibit prostaglandin synthesis by inhibiting cyclooxygenase, leading to a reduction in inflammation and swelling while leaving central pain processing unaddressed. Similarly, opioids bind to mu, delta or kappa opioid receptors, reducing neuronal excitability in the neurons carrying pain signals to the Central Nervous System (CNS) leading to less perceived pain (PMID 9202932) but do not address inflammation, local swelling, or muscle tension. In fact, none of the pain pills currently on the market address all of the multiple components or the root cause of pain.

Additionally, current oral pain medications have significant safety concerns. For example, opioids are highly addictive, requiring higher doses over time to achieve the same effect, creating a hyperalgesic state via multiple molecular mechanisms (Zhizhong Z. Pan, Mechanisms of Opioid Tolerance, Molecular Pain pp 413-422) in both central and peripheral pain systems in the body. There is a high risk of accidental death from self-administered overdose, due to the ease of addiction to this class of medications. NSAIDs are toxic to the kidneys, ears, and liver; and carry a significant risk for generalized bleeding as well as peptic ulcer formation. NSAIDs may also lead to a hyperalgesic state via multiple proposed mechanisms (PMID 25722692). Acetaminophen, the third major oral pain medication, is toxic to the liver and kidneys, and potentially increases risk of bleeding and peptic ulcers.

Current topical pain preparations also have limitations. For example, NSAID creams have a potential to significantly increase the risk for bleeding, heart attacks, high blood pressure, stroke, peptic ulcers, and bowel perforation in addition to inhibiting tissue healing. Menthol-based creams are not practical for use in cold weather, or by patients with broken skin. Capsaicin and arnica creams carry a lesser risk of bleeding, heart attack, high blood pressure and stroke than NSAID creams, but still have a potential to cause skin irritation. Additionally, none of the current topical pain medications penetrate further than the outermost layer of the epidermis, resulting in pain relief for superficial structures only, leaving the pain of underlying structures untreated. Furthermore, the effects of current topical pain medications typically wear off after a few hours, requiring repeated application.

The above listed diseases are simply a few examples of the most common chronic illnesses which plague modern humans. In reality, virtually all diseases may be affected to some degree by imbalances of cell membrane composition and/or functions.

There is a need for a formulation that can address disturbances in cell membrane composition and functions, including, e.g., the formulation that is capable of safely and effectively addressing the multiple aspects of pain. For topical formulations, it would need to penetrate into affected tissues to deliver active ingredients into the injured area. Ideally, it would have a fast onset of efficacy, have a long duration of efficacy, and hasten healing of the affected tissues such that pain or other pathological processes improve.

There is also a need for a formulation that can improve absorption of substances applied to the skin. Application of such a formulation prior to applying commercially available products ideally would facilitate, restore and/or improve delivery into the skin and would facilitate incorporation of an ingredient(s) into cell membranes or into the intracellular space depending on size, charge, or other properties.

SUMMARY OF THE INVENTION

It is an object of the invention to provide a formulation that can correct an imbalance in a cell membrane composition.

It is a further object of the present invention to provide a formulation that can correct a disturbance in a cell membrane function.

It is an additional object of the present invention to provide a formulation that can improve absorption of substances applied to the skin.

It is also an object of the present invention to provide a formulation that treats a disease by modulating cell membrane composition and/or function.

It also an object of the present invention to provide a topical formulation that is capable of inducing production of pluripotent stem cells.

It is an additional object of the invention to provide a topical formulation that can reprogram differentiated skin cells into a pluripotent stem cell state.

It is a further object of the invention to provide a topical formulation that is capable of altering gene expression without the use of a viral vector.

It is also an object of the invention to provide a topical formulation that is capable of penetrating and delivering active ingredient(s) into the injured area beyond the outermost layer of epidermis.

It is also an object of the invention to provide a topical formulation that is capable of penetrating and delivering active ingredient(s) distal from the site of injury or distal from target tissues beyond the outermost layer of the epidermis in order to purposely facilitate a delayed response.

In furtherance of the above objects and others, the present invention provides formulations capable of incorporating into existing cell membranes and restoring cell membrane composition and/or function(s) and modulating therapeutic effect(s). The formulations comprise a mixture of fatty acids in specific ratios such that the formulation may cross, integrate, modulate, regulate, or restore a function(s) of a membrane of a cell, an organelle or an exosome, and/or a function of cell and/or an organelle and/or an exosome. The formulations may, e.g., supply a component(s) to correct a deficiency in a cell membrane composition. The formulation may also be formulated to reduce transmission of signals in and between the cells, e.g., to reduce signaling for pain, inflammation, excess oxidation, etc. The formulation may also be formulated to increase healthy stem cell response to injury while limiting abnormal proliferation, division and/or other unhealthy responses of cells. The formulations may also be formulated to interfere with functions of cell membranes of microbes, viruses, fungi, insects, and parasites thereby resulting in a destruction or inactivation of microbes, viruses, fungi, insects, and parasites or an inability of microbes, viruses, fungi, insects and parasites to infect or inhabit their host(s). The fatty acids in the formulations may come from oil(s) and/or fats or may be individually incorporated into the mixture. In addition to the fatty acids, the formulations may comprise other components, as, e.g., described in detail below. The ratio of the fatty acids in the mixture and the formulations themselves (i.e., the individual components of the formulation and their amounts) are customizable, as for example, described in detail below, to address specific diseases, and/or root deficiencies, and/or restore a composition of a membrane of a cell, as well as the membrane of various organelles within a cell (e.g., a mammalian cell), and/or restore and/or improve cellular function(s). The formulations may allow, e.g., for 1) delivery of therapeutic materials directly into tissues and cells and/or 2) delivery of raw materials (e.g., proteins, minerals, vitamins, therapeutics, etc.) necessary to rebuild tissues into the inter- and intracellular space, to rebuild tissues and/or restore a cell membrane's function or the function of membranes of subcellular organelles. In certain embodiments, the incorporation of the formulation into a cell membrane may directly disrupt the lipid rafts housing clusters of pain transmembrane proteins which require being clustered together in order to signal for pain.

A formulation in accordance with the invention generally comprises: (i) a base composition, and one or more additional ingredient(s) dispersed in the base composition such that the formulation has a fatty acid composition that is substantially similar to that of a membrane of a cell, an organelle or an exosome. The fatty acid composition of the formulation renders the formulation capable of one or more of the following: crossing, integrating, modulating, regulating, or restoring the membrane's function(s) and/or a function(s) of a cell, an organelle or an exosome. The base composition may include a lipid. A lipid may, e.g., be an oil or a mixture oils or another substance comprising fatty acids. Thus, a lipid may, e.g., be an essential oil or a mixture of essential oils. The base composition may comprise from about 40% to about 99% of the formulation by volume. In some of the embodiments, the base composition comprises one or more oils. The one or more oils of the base composition may, e.g., be selected from a group consisting of emu oil, coconut oil, macadamia nut oil, high oleic sunflower seed oil, olive oil, and mixtures comprising two, three, four or five of the foregoing oils. In some embodiments, the base composition comprises a mixture of emu oil, coconut oil and macadamia nut oil. In some embodiments, the base composition comprises a mixture of high oleic sunflower seed oil, coconut oil and macadamia nut oil. Emu oil may, e.g., comprise from 0% to about 99% of the base composition by volume. Coconut oil may, e.g., comprise medium chain triglycerides derived from coconut oil, and comprise from 0% to about 95% of the base composition by volume. High oleic sunflower seed oil may, e.g., comprise from 0% to about 90% of the base composition by volume. Macadamia nut oil may, e.g., comprise from 0% to about 25% of the base composition by volume. Olive oil may, e.g., comprise from about 0% to about 80% of the base composition by volume. In some embodiments, the base composition consists of medium chain triglycerides derived from coconut oil. However, other oils and lipids can also be used in the formulations of the invention as long as they are combined in amounts that provide a base composition that has a fatty acid composition that is substantially similar as that of a membrane of a cell, an organelle or an exosome (or, in certain embodiments, a fatty acid composition that contains more oleic acid than that of a membrane of a cell, an organelle or an exosome), and renders the formulation capable of crossing, integration, modulation, regulation, or restoration of membrane's function(s) and/or a function(s) of a cell and/or organelle and/or an exosome. The formulation may further comprise a biosilicate (e.g., a Food Grade Diatomaceous Earth (FDGE) biosilicate) or a plurality of biosilicates (e.g., a plurality of FDGE biosilicates). The biosilicate(s) may, e.g., extend a duration of a desired effect(s) of the formulation. The formulation may be free from conventional drugs (i.e., substances approved by regulatory authorities (e.g., US FDA) for treatment of diseases in humans). The formulations may also be free from preservatives.

The one more additional ingredient(s) of the formulation may be selected from a group consisting of a phospholipid, a ceramide, cholesterol, a fatty acid, an oil, a vitamin, a mineral, a therapeutic agent, an exosome, or a combination of any of the foregoing. In some of the preferred embodiments, the one or more additional ingredient(s) in the formulation may be an essential oil or a mixture of essential oils or an exosome.

The base composition and the one or more additional ingredient(s) may be included in the formulation in an effective amount to reduce severity or alleviate a symptom of a disease, associated with an injury, damage or dysfunction of a cellular membrane or an organelle in a mammal. The disease associated with a dysfunction, injury of damage of a cellular membrane function may, e.g., be pain, eczema, psoriasis, erythema, a burn, a cut, a bruise, a boil, a scar, a keloid, a non-healing wound, acne, rosacea, an allergy, an arthritis, an arthralgia, cancer, a neuropathy, a metabolic syndrome, an infection, a canker sore, an ulcer, Ulcerative Colitis (UC), a mucositis, diverticulitis, celiac disease, a colitis, Crohn's Disease (CD), Irritable Bowel Syndrome (IBS), Inflammatory Bowel Disease (IBD) atherosclerosis, Alzheimer's Disease (AD), Parkinson's Disease (PD), gout, solar lentigo, senile lentigines, skin atrophy, Lichen Sclerosis (LS), Lichen Planus (LP), asthma, Chronic Obstructive Pulmonary Disease (COPD), angina, Coronary Artery Disease (CAD), hypertension (HTN), hyperlipidemia (HLD), Diabetes Mellitus (DM), metabolic syndrome, insulin resistance, a neuropathy, PMS, anxiety, depression, nightmares, insomnia, neuralgia, sciatica, mastitis, conjunctivitis, a convulsive disorder, alcohol withdrawal, abnormal muscle tension, xerosis, fibromyalgia, alopecia, Erectile Dysfunction (ED), Restless Legs Syndrome (RDS), Multiple Sclerosis (MS), abnormal sleep debt, osteopenia, osteoporosis, anemia of chronic disease, urticaria, hemorrhoids, Chronic Fatigue Syndrome (CFS), leukoplakia, vaginal atrophy, edema, heavy lymph load, sunburn, hyperpigmented skin due to aging or prior trauma, or a muscle spasm. The symptom of the disease may, e.g., be pain, inflammation, skin irritation, rash, a lesion, a wrinkle, hyperpigmentation, a keloid, a scar, pruritus, itching, indigestion, diarrhea, a cramp, cough, a bronchospasm, a discoloration, and combinations or two or more of the foregoing. The base composition and the additional ingredient(s) may also be included in the formulation in an amount that disrupts cellular membrane function (e.g., of a virus, bacteria, fungi, insect or parasite) or modulates a cellular membrane function to activate healthy response from a cell, its subcellular organelles, or a group of cells (as, e.g., in a tissue). The formulation may also be formulated to restore proper amounts of missing cell membrane components to facilitate healthy cell signaling.

A formulation may, e.g., comprise (i) a base composition comprising a lipid comprising fatty acids, and (ii) one or more additional ingredient(s) dispersed in the base composition, the additional ingredient(s) selected from a group consisting of a phospholipid, a ceramide, cholesterol, a fatty acid, an oil, a vitamin, a mineral, a therapeutic agent, a bioactive ingredient, an exosome, or a combination of two or more of any of the foregoing, wherein the fatty acids in the base composition are of a type and in amounts that render a fatty acid composition of the base composition identical or substantially similar to a fatty acid composition of a cell membrane or a cell organelle of mammalian sebum, and the base composition comprises from about 30% to about 99% of the formulation by volume. The fatty acids may, e.g., be selected from a group consisting of myristic acid (C14:0), lauric acid (C12:0), palmitic acid (C16:0), arachidonic acid (C20:4 n-6), stearic acid (C18:0), oleic acid (C18:1 n-9), linoleic acid (C18:1 n-9), linoleic acid (C18-3 n-9), crotonic acid (C4H6O2), myristoleic acid, palmitoleic (C16:1) acid, sapienic acid (C16:1 n-10), oleic acid (C18:1 n-9), elaidic acid or trans-oleic acid (C18:1 n-9), vaccenic acid (C18:1 n-7), gadoleic acid (C20:1 n-11), eicosenoic acid (C20:1 n-9), erucic acid (C22:1 n-9) nervonic acid (C24:1 n-9), or a combination of two or more of any of the foregoing. The fatty acid composition of the base composition may be identical or substantially similar to a fatty acid composition of the cell membrane of a human cell. The lipid could, e.g., be a mixture comprising coconut oil and macadamia nut oil and may further comprise emu oil and/or high oleic sunflower seed oil. The one or more additional ingredients may comprise a mixture of German chamomile oil, Roman chamomile oil, and Moroccan chamomile oil, the mixture comprising from about 5% to about 30% of the formulation by volume.

The formulation may also comprise a mixture of individual fatty acids, wherein the fatty acids are combined in the mixture such that the mixture and/or formulation has a fatty acid composition that is substantially the same (i.e., approximate) as that of non-diseased human skin and/or sebum and/or cell membranes. In some of these embodiments, the fatty acids are combined such that the fatty acid composition of the mixture is substantially the same as that of human skin and/or sebum. In some of these embodiments, the fatty acids are combined such that the composition of the mixture supplements components of a membrane of a cell, organelle or exosome which may be deficient in such components due to disease, poor diet, or another cause. The mixture may, e.g., comprise, in % by volume, from about 0% to about 40% ceramides (e.g., 13%), from about 5% to about 99% fatty acids (e.g., 47%), including, e.g., phospholipids such as phosphatidylcholine, sphingomyelin, phosphatidylethanolamine, phosphatidylserine, and phosphatidylinositol; from about 0% to about 25% cholesterol (e.g., 7%), from about 0% to about 25% cholesterol esters (e.g., 2%), from about 0% to about 25% squalene (e.g., 11%), from about 0% to about 20% triglycerides (e.g., 3%), from about 5% to about 99% proteins (e.g., 47%), and from about 0% to about 30% wax esters (e.g., 17%). The mixture may also comprise myristic acid (C14:0), lauric acid (C12:0), palmitic acid (C16:0), arachidonic acid (C20:4 n-6), stearic acid (C18:0), oleic acid (C18:1 n-9), linoleic acid (C18:1 n-9), linoleic acid (C18-3 n-9), crotonic acid ($C_4H_6O_2$), myristoleic acid, palmitoleic (C16:1) acid, sapienic acid (C16:1 n-10), oleic acid (C18:1 n-9), elaidic acid or trans-oleic acid (C18:1 n-9), vaccenic acid (C18:1 n-7), gadoleic acid (C20:1 n-11), eicosenoic acid (C20:1 n-9), erucic acid (C22:1 n-9) nervonic acid (C24:1 n-9), or a combination of two or more of any of the foregoing, such that the fatty acid composition of the mixture is substantially the same as that of healthy human skin and/or sebum. The mixture may also comprise a composition that is sufficient to correct an imbalance in a membrane of a cell or a membrane of a cell organelle, e.g., supply deficient membrane component(s). In some of the embodiments, oleic acid comprises greater than 50% (e.g., about 65%, about 70%, about 75%, about 80%, about 85%, or about 95%) of the fatty acid composition. Generally, higher concentrations of oleic acid is required to penetrate into the subcellular organelles (e.g., to directly influence cellular metabolism) than a cell membrane because the compounds must cross more than one set of cell membranes. The fatty acids may be incorporated into the formulations by themselves or in the form of oils, phospholipids or mixtures of lipids.

The present invention is specifically directed in part to a formulation comprising a composition comprising palmitic acid, stearic acid, oleic acid, and linoleic acid, wherein the palmitic acid comprises from about 20% to about 75% of the composition by weight, the stearic acid comprises from about 11% to about 13% of the composition by weight, the oleic acid comprises from about 8% to about 31% of the composition by weight, the linoleic acid comprises from about 15% to about 23% of the formulation by weight, and the formulation is capable of crossing a cell membrane and/or incorporating into a cell membrane and/or modulating a cell membrane composition and/or function. In some of the embodiments, the mixture may comprise a fatty acid composition that is similar to that of a mammalian cell membrane (e.g., a human cell membrane), except that it contains more oleic acid that the mammalian cell. In some of the embodiments, the concentration of oleic acid may be adjusted to facilitate different degrees of penetration for admixed compound(s).

In certain embodiments, the formulation may comprise (i) a base composition comprising a lipid comprising fatty acids, and (ii) a mixture comprising clove essential oil, cinnamon essential oil, rosemary essential oil, eucalyptus essential oil, lemon essential oil, ravintsara essential oil, and cinnamon essential oil dispersed in the base composition, wherein the lipid comprises a mixture of high oleic sunflower seed oil, coconut oil, and macadamia nut oil, clove essential oil comprises from about 0.1% to 30% of the formulation by volume; cinnamon essential oil comprises from about 0.1% to 30% of the formulation by volume; rosemary essential oil comprises from about 0.1% to 30% of the formulation by volume; eucalyptus essential oil comprises from about 0.1% to 30% of the formulation by volume; lemon essential oil comprises from about 0.1% to 30% of the formulation by volume; ravintsara essential oil comprises from about 0.1% to 20% of the formulation by volume; cinnamon leaf essential oil comprises from about 0.05% to about 20% of the formulation by volume; and the base composition comprises from about 50% to about 99% of the formulation by volume. The formulation may further comprise, by volume, from about 0.05% to about 20% frankincense essential oil and/or from about 1% to about 30% thyme essential oil. The formulation may also comprise, in % by volume, from about 1% to about 30% biosilicates, from about 0.04% to about 20% German chamomile essential oil, from about 1% to about 20% Moroccan chamomile essential oil, from about 0.04% to about 20% Roman chamomile essential oil, from about 0.04% to about 10% jasmine essential oil, from about 0.04% to about 10% lemongrass essential oil, from about 1% to about 10% coconut oil, from about 5% to about 4% macadamia oil, from about 10% to about 80% emu oil. The formulation may further comprise vitamin D, hyaluronic acid, vitamin E, vitamin A, glycerin, ubiquinol, myrrh essential oil, frankincense essential oil, German chamomile essential oil, Roman Chamomile essential oil, and Moroccan chamomile essential oil. The formulation may further comprise a Food Grade Diatomaceous Earth (FDGE) biosilicate(s).

The formulation may also comprise (i) a base composition comprising a lipid comprising fatty acids, and (ii) a mixture comprising German chamomile essential oil, Moroccan chamomile essential oil, Roman chamomile essential oil, frankincense essential oil, myrrh essential oil, jasmine essential oil, lemongrass essential oil, sweet orange essential oil, bitter orange essential oil, rosemary essential oil, galangal essential oil, xiang mao essential oil, palmarosa essential oil, neroli essential oil, licorice extract, lecithin, coconut oil; the mixture dispersed in the base composition, wherein the lipid comprises a mixture comprising emu oil, coconut oil and macadamia nut oil, the base composition comprises from about 50% to about 99% of the formulation by volume. The formulation may, e.g., comprise, in % by volume, from about 0.01% to about 3% German chamomile essential oil, about 0.01% to about 3% Moroccan chamomile essential oil, from about 0.01% to about 3% Roman chamomile essential oil, from about 0.01% to about 10% frankincense essential oil, from about 0.01% to about 10% myrrh essential oil, from about 0.01% to about 2% of jasmine essential oil, from about 0.01% to about 2% of lemongrass essential oil, from about 0.01% to about 3% sweet orange essential oil, from about 0.01% to about 3% bitter orange essential oil, from about 0.01% to about 3% rosemary essential oil, from about 0.01% to about 3% galangal essential oil, from about 0.01% to about 3% xiang mao essential oil, from about 0.01% to about 3% palmarosa essential oil, from about 0.01% to about 3% neroli essential oil, from about 0.01% to about 5% licorice extract, from about 2% to about 9% lecithin, from about 0.01% to about 2% coconut oil, from about 0.01% to about 5% macadamia nut oil, from about 35% to about 90% Emu oil. The formulation may further comprise a Food Grade Diatomaceous Earth (FDGE) biosilicate.

Administration of the formulations described herein may result in a modulation of the cell membrane composition and/or function. In some of the embodiments, an administration of the formulations described herein may result in an alleviation of pain. In some of the embodiments, an administration of the formulations described herein may result in improved wound healing. In some of the embodiments, an administration of the formulations described herein may result in improvement or resolution of eczema. In some of the embodiments, an administration of the formulations described herein may result in an improvement or resolution of psoriasis. In some of the embodiments, an administration of the formulations described herein may result in an improvement in the appearance of scars. In some of the embodiments, an administration of the formulations described herein may result in an improved recovery from burns. In some of the embodiments, an administration of the formulations described herein may result in an improvement in endocrine function. In some of the embodiments, an administration of the formulations described herein may result in an improvement of a serum lipid profile (e.g., an increase in HDL and/or a decrease in LDL and/or a decrease in triglycerides). In some of the embodiments, an administration of the formulations described herein may result in improved circulation and improvement in symptoms of Raynaud's phenomenon. In some of the embodiments, an administration of the formulations described herein may result in improvement in function of the nervous system. In some of the embodiments, an administration of the formulations described herein may result in improved concentration. In some of the embodiments, an administration of the formulation described herein may result in improved appearance and quantity of hair. In some of the embodiments, an administration of the formulations described herein may result in appearance of skin health. In some of the embodiments, an administration of the formulations described herein may result in alleviation of or improvement in headaches. In some of the embodiments, an administration of the formulations described herein may result in improvement of abdominal pain and diarrhea associated with Inflammatory Bowel Disease (e.g., Crohn's Disease, Ulcerative Colitis), and with Irritable Bowel Disease. In some of the embodiments, an administration of the formulation described herein may result in an improvement or alleviation of anxiety and/or depression. In some of the embodiments, an administration of the formulations described herein may result in improvement in the experience of wearing a mask. In some of the embodiments, an administration of the formulations described herein may result in reduction in nausea. In some of the embodiments, an administration of the formulations described herein may result in improved mood. In some of the embodiments, an administration of the formulations described herein may result in decreased appetite. In some of the embodiments, an administration of the formulation described herein may result in improvement in insomnia. In some of the embodiments, an administration of the formulations described herein may result in improvement or alleviation of social anxiety in patients with social anxiety. In some of the embodiments, an administration of the formulations described herein may result in improvement of an infection of the skin, nail, or body part caused by fungus, bacteria or virus.

The present invention specifically encompasses liquid formulations comprising a fatty acid composition substantially similar (i.e., approximate) to a fatty acid composition of healthy human skin and/or sebum.

In one embodiment, the invention provides a formulation comprising a mixture of oils (e.g., animal oils and/or vegetable oils). The oils included in the mixtures of the present invention may be selected, e.g., from a group comprising or consisting of emu oil, German chamomile essential oil, Moroccan chamomile essential oil, Roman chamomile essential oil, coconut oil, macadamia oil, jojoba wax, lime essential oil, grapefruit essential oil, blackberry seed oil, blueberry seed oil, raspberry seed oil, yuzu essential oil, turmeric essential oil, garlic essential oil, wolfberry seed oil, jasmine essential oil, ginger essential oil, myrrh essential oil, orange essential oil, organic extra virgin olive oil, clove essential oil, calamus essential oil, cassia essential oil, cinnamon essential oil, frankincense essential oil, rosemary essential oil, eucalyptus essential oil, flaxseed oil, lemon essential oil, lemongrass essential oil, xiang mao essential oil, galangal root essential oil, licorice extract, pomegranate seed oil, ravintsara essential oil, bergamot essential oil, cinnamon leaf essential oil, bupleurum extract, jasminum officinale essential oil, vanilla planifolia essential oil, and combinations of any of the foregoing. In some of these embodiments, the formulation comprises emu oil and at least one additional ingredient selected from the group consisting of German chamomile essential oil, Moroccan chamomile essential oil, Roman chamomile essential oil, coconut oil, macadamia oil, jojoba wax, lime essential oil, grapefruit essential oil, blackberry seed oil, blueberry seed oil, raspberry seed oil, yuzu essential oil, turmeric essential oil, garlic essential oil, wolfberry seed oil, jasmine essential oil, ginger essential oil, myrrh essential oil, orange essential oil, organic extra virgin olive oil, clove essential oil, calamus essential oil, cassia essential oil, cinnamon essential oil, frankincense essential oil, rosemary essential oil, eucalyptus essential oil, flaxseed oil, lemon essential oil, lemongrass essential oil, xiang mao essential oil, galangal root essential oil, licorice extract, pomegranate seed oil, ravintsara essential oil, bergamot essential oil, cinnamon leaf essential oil, bupleurum extract, jasminum officinale essential oil, vanilla planifolia essential oil, etc.), and combinations of any of the foregoing.

In addition to a base composition, the formulation of the invention may comprise at least one additional ingredient selected from the group consisting of an oil, a phospholipid, a ceramide, cholesterol, a fatty acid, a vitamin, a mineral, an amino acid, a hyaluronic acid, a fusogen, a biofermentation product of fruit, seaweed or other plants, a therapeutic agent (e.g., a drug approved by U.S. FDA for use in humans), an exosome, a bioactive ingredient, dead sea salt, an organic pea protein, an organic brown rice protein, N-acetyl cysteine, or a combination of two or more of the foregoing.

In addition to a base composition, the formulation may also comprise a biosilicate (e.g., Food-Grade Diatomaceous Earth (FGDE)) and/or another pharmaceutically acceptable matrix. In some of the embodiments, biosilicates and pharmaceutically acceptable matrices provide release of a component(s) of the formulation for an extended period of time. The extended release may, e.g., be provided at least for 10 hours, 12 hours, 14 hours, 16 hours, 18 hours, 20 hours, 22 hours, 24 hours, 26 hours, 28 hours, 30 hours, 36 hours, 48 hours, 60 hours, 72 hours, 96 hours, 5 days, 6 days, 7 days, 8 days, 9 days, or 10 days. The extended release may be provided up to 1 week, 2 weeks, 3 weeks, 4 weeks, 5 weeks, 6 weeks, 7 weeks, 8 weeks, 9 weeks, 10 weeks, 11 weeks, 12 weeks, or longer, after application of the formulation to an affected area.

The individual fatty acids or oils in the formulations of the invention may, e.g., act as a carrier for incorporation and/or delivery of other phospholipids, ceramides, cholesterol, essential and free fatty acids, additional oils, vitamins, minerals, bioactive ingredients, and additional therapeutic agents into and/or through cell membranes and/or (ii) as a therapeutic agent, e.g., to correct an impairment in a cell membrane composition and/or function and/or (iii) to stimulate expression of stem cell transcription factors Sox-2, Nanog, Oct4, Klf4, and c-Myc and/or (iv) downregulate expression of markers of inflammation such as COX2, NO, TNF-α, and iNOS, thromboxane B2, prostaglandin E2, leukotriene B4, IFNγ, interleukin-1 (IL-1), IL-6, IL-8, IL-12, and PPARγ (v) stimulate production of anti-inflammatory cytokines and/or (vi) stimulate production of pluripotent stem cells (e.g., capable of differentiating into skin cells, connective tissues, blood vessels, neurons, and a variety of other cell types). The mixture may comprise only vegetable oils, only animal oils or a combination of vegetable oils and animal oils, with or without at least one additional ingredient(s). In the preferred embodiments, the formulation comprises a base composition comprising a mixture of fatty acids and at least one additional ingredient. The fatty acids for the compositions may be contained in oil(s) included in the formulations.

In some of the embodiments, the formulations of the invention do not contain any conventional therapeutic agents (i.e., therapeutic agents approved by the U.S. Food and Drug Administration (U.S. FDA) for the treatment of the disease in humans) and only contains oils and/or other materials that are considered Generally Recognized as Safe (GRAS) by U.S. FDA.

In some of the embodiments, the formulations of the invention may contain conventional therapeutic agents (i.e., therapeutic agents approved by the U.S. Food and Drug Administration (U.S. FDA) for the treatment of the disease in humans).

In certain embodiments, a formulation according to the invention includes a mixture of at least two ingredients listed in Table 1 or elsewhere in this application. The ingredients for inclusion in the mixture and the amounts are selected based on the desired indication and/or needs of a particular subject (e.g., a human in need of a treatment), based on the guidelines provided herein below, and the knowledge of a person of ordinary skill in the art. It is contemplated that a mixture of any two (or more) ingredients from Table 1 could be used in the formulations of the invention.

TABLE 1

| Ingredient | Properties | Exemplary Utilities |
|---|---|---|
| Emu oil (EO) (contains oleic acid, linoleic acid, as well as antioxidants carotenoids and flavones) Range: 1%-99% by volume | Anti-inflammatory, decreases swelling, capable of delivery of ingredients into skin, for example increasing hair growth when combined with minoxidil as compared to minoxidil alone (PMID 25657781). Emu oil may exert its anti-inflammatory effects by 5 main mechanisms: 1) By reducing cellular production of inflammatory cascade members NO, TNF-α, and iNOS in macrophages (PMID 29526880) but does not impair their ability to phagocytose (engulf) debris or bacteria. 2) EO also inhibits inflammation due to its high concentration of Omega-3, which inhibits inflammatory pathways that produce thromboxane B2, prostaglandin E2, and leukotriene B4, and suppresses activators of inflammatory genes such as IFNγ (PMID 26217022) 3) EO also exerts anti-inflammatory effects because of its high concentrations of omega-9 fatty acids, which reduce the migration of white blood cells (macrophages) to sites of inflammation. 4) EO also may exert anti-inflammatory effects due to synergistic effect of the different omega fatty acids (PMID 22369065) 5) Additionally, EO reduced acute inflammation in rats more than other oils with a higher content of the above fatty acids, thus researchers conclude that this effect can't be solely attributed to its fat component, and may instead by due to the trace elements (naturally occurring antioxidants, vitamins and other organic compounds) (PMID 17638122, PMID 22369065) Emu oil may protect against cancer and aging by its antioxidant components and by its high ratio of unsaturated to saturated fats, both which reduce tissue damage by decreasing oxidative stress on tissues and stem cells (PMID 17638122, PMID 22369065). Emu oil may permeate, moisturize, and help heal the skin by the following 6 mechanisms: 1) It destabilizes the alpha-helix structure of keratin (PMID 28527394) 2) It interacts with fats in the skin (PMID 28527394) 3) It enhances permeation of drugs into the skin (PMID 28527394) 4) It promotes growth of new skin cells (epithelialization, differentiation of epidermal layers) (PMID 15837639, PMID 15567771, PMID 27069472) 5) It promotes restructuring of skin (fibrogenesis, collagen synthesis) (PMID 15837639, PMID 15567771, PMID 27069472) 6) It shifts white blood cells from the pro-inflammatory kind (M1 phenotype) to the anti-inflammatory kind (M2 phenotype) (PMID 28830252) Emu oil increases stem cell markers Sox-2, Nanog, Oct4, Klf4, and c-Myc) which converts differentiated skin cells back into a stem cell-like state (PMID 28718680). This property alone may be helpful for maintaining youthful and healthy skin, and in the treatment of cancer—in which reprogramming of cancer stem cells back into a naïve stem-cell state could mean selective apoptosis of cancer stem cells (stem cells which have sustained damage and become transformed to give rise to tumor causing cells). | Diseases involving inflammation, including, e.g., pain, cancer and aging; multiple sclerosis, rheumatoid and osteoarthritis, arthralgias induced by chemotherapy, gout, ulcerative colitis, improves skin barrier function, reduces dark spots from sun exposure, many others. |

TABLE 1-continued

| Ingredient | Properties | Exemplary Utilities |
|---|---|---|
| | However, emu oil has linoleic acid, an omega-6 polyunsaturated fat that improves skin barrier function (PMID 7373078) but when consumed in high quantities is associated with higher rates of obesity and cancer (PMID 23249760) Linoleic acid, as well as alpha-linolenic acid, both which are found in emu oil, have been shown to lighten UV-induced hyperpigmentation of the skin (PMID 9749992) Palmitic Acid is a saturated fat essential to skin health (PMID 24262790), while Stearic acid is a saturated fatty acid beneficial to skin hydration and healing (PMID 23363400) and important in wound healing of burns (PMID 10945745) and can increase the "good" cholesterol HDL while reducing the "bad" cholesterol LDL (PMID 19939984) Emu oil has been shown to decrease the joint pain induced by aromatase inhibitors taken by women with hormone receptor-positive early breast cancer (PMID 28691132) May synergize with glycyrrhizin (the main component of licorice root extract, see below) to exert a stronger anti-inflammatory effect by modulating inflammatory mediators PPARγ and TNFα in an animal model of ulcerative colitis (PMID 25560991) Taken internally, emu oil reduced disease severity in a mouse model of chronic ulcerative colitis (PMID 30907169). Applied topically when combined with curcumin, emu oil was shown to increase skin permeation of curcumin in a rodent model of rheumatoid arthritis, and reduced proinflammatory mediators such as TNFα, IL-1β and IL-6 in arthritic animals (PMID 27178879) U.S. Pat. No. 5,744,128: Use of emu oil for stimulating skin and hair growth. Google Books. 2016. A review of emu oil composition and benefits, with references can be found at https://content.selfdecode.com/emu-oil/ | |
| Oleic acid (OA) (Note: OA is a component of emu, olive, sunflower, coconut, macadamia nut, jojoba wax, and other oils) Range: 1%-97% by volume | Anti-inflammatory, decreases swelling, superior delivery of ingredients into skin. Oleic acid (OA) enhances lipophilic penetration of skin cells (PMID 21871866, PMID 2367329), able to facilitate targeted drug delivery across the skin (PMID 2514720) most likely because it reduces energy barriers to membrane fusion (PMID 21871866) and creates a temporary disruption to the cell membrane allowing for drug permeability (PMID 2235880). OA has been shown to decrease expression of a cholesterol transport-related protein (NPC1L1) in a cell model (PMID 21181463). OA has been shown to reduce blood pressure (PMID 10737284), in some cases with patients no longer needing antihypertensive medications. OA and other monounsaturated fatty acid (MUFA) intake have been positively associated with a lean body habitus (PMID 18194589). A diet high in MUFAs such as OA in diabetic patients restores sensitivity to insulin, increases transport of sugar into cells, and changes the composition of vasculature thus helping to reverse diabetes (PMID 10700478). OA has anti-inflammatory properties, but in the setting of a wound has pro-inflammatory properties which stimulate a stronger wound response with an increase in wound healing tissue mass, while decreasing the thickness of the necrotic tissue layer in the wound (PMID 17918246). OA is crucial for nerve repair, myelin production and inflammation reduction, promoting growth of new nerve cells (PMID 24058332), and unexpectedly has been shown to decrease anger | Increases delivery of other bioactive molecules past membranes of cells and organelles. Cancer, Diabetes, Obesity, Hypertension, Peripheral neuropathy, hyperlipidemia, wound healing, burns, weight loss, multiple sclerosis, pruritic rashes such as eczema, psoriasis, creating a calmer mood (decreases anger), and many others. Moisturizer. |

TABLE 1-continued

| Ingredient | Properties | Exemplary Utilities |
|---|---|---|
| | while increasing mitochondrial function (PMID 23446891), decreases intracellular oxidative stress (PMID 31802387) thus decreasing inflammation and swelling by decreasing oxidative stress within cells (PMID 10590211), thus decreasing pain as well as decreases risk of DNA damage thus decreasing the risk of cancer. Additionally, it protects against age-related cognitive decline (PMID 10331679) and directly inhibits pain and itch receptors (PMID 27721373). If taken excessively can eventually lead to heart failure (PMID 28391879) though this would be impossible to do with a topical preparation. | |
| Olive oil Range: 1%-97% by volume | Anti-inflammatory properties of olive oil, rich in oleic acid have been well-documented, useful in protecting against cancer (PMID 30583613), aging (PMID 26840281), fatty liver disease (PMID 31215262), neurodegeneration (PMID 29068387, PMID 32468462) modulates the immune system (PMID 29495598), improves metabolism/decreases cardiovascular disease (PMID 30487558) among many other benefits. | Anti-inflammatory, important in protecting against cancer, aging, fatty liver disease, neurodegeneration, cardiovascular disease. Moisturizer. |
| High oleic sunflower seed oil Range: 1%-97% by volume | Anti-inflammatory properties resulting in improved cholesterol profile (PMID 10545672), decreased atherosclerosis (PMID 15350986, PMID 9482765) | Anti-inflammatory properties, useful in improving hyperlipidemia, hypercholesterolemia, and decreasing cardiovascular disease. Moisturizer. |
| Coconut oil (including Medium Chain Triglycerides derived from coconut oil) Range: 0.0001%-97% by volume | Improves hyperlipidemia and fatty acid profile to reduce cardiovascular risk (PMID 26946252, PMID 30725578), improves liver antioxidant status (PMID 28816548), has anti-cancer properties, improves fatty liver disease, improves insulin resistance, improves antioxidant status, is anti-inflammatory, has anti-microbial properties, and useful as a moisturizer (PMID 33022082). A rich source of non-esterified fatty acids such as myristic acid and lauric acid. | Improves hyperlipidemia, hypercholesterolemia, decreases cardiovascular disease. Helpful in cancer, fatty liver disease, metabolic syndrome, diabetes, anti-aging, diseases of inflammation, and in treatment of dry skin and preventing infections. Moisturizer. |
| Fish Oil (EPA + DHA) Range: 0.0001%-97% by volume | Decreases cardiovascular risk, atherosclerosis, diabetes, cancer, arthritis, osteoporosis, autoimmune and neurological disorders, supporting healthy immune function | Improves hyperlipidemia, hypercholesterolemia, decreases cardiovascular disease. Helpful in cancer, fatty liver disease, metabolic syndrome, diabetes, anti-aging, diseases of inflammation, and in treatment of dry skin and preventing infections. |
| Flaxseed Oil Range: 0.001%-97% by volume | Decreases cardiovascular risk, atherosclerosis, diabetes, cancer, arthritis, osteoporosis, autoimmune and neurological disorders, supporting healthy immune function (PMID 25190822). Rich in healthful oleic and linolenic acid. | Improves hyperlipidemia, hypercholesterolemia, decreases cardiovascular disease. Helpful in cancer, fatty liver disease, metabolic syndrome, diabetes, anti-aging, diseases of inflammation, and in treatment of dry skin and preventing infections. Moisturizer. |

TABLE 1-continued

| Ingredient | Properties | Exemplary Utilities |
| --- | --- | --- |
| Macadamia Nut Oil Range: 0.0001%-97% by volume | Possesses a very high concentration of healthy mono-unsaturated fatty acids, and low in unhealthy omega-6 fatty acid 18:2n-6 and in saturated fatty acids (PMID 8541698) which translates into improved serum lipid profile, leading to decreased risk for atherosclerosis, cardiovascular risk, stroke and cancer risk. Relatively rich in arachidonic and oleic acids; and healthy mono-unsaturated fatty acids. | Helpful in treating hyperlipidemia, resulting in decreased risk for atherosclerosis, cardiovascular risk, stroke and cancer risk. Moisturizer. |
| Jojoba Wax Range: 0.001%-97% by volume | Has a fatty acid profile similar to that of human sebum. Useful as a moisturizer. | Moisturizer. Carrier oil. |
| Lecithin Range: 0.0001%-70% by volume | Useful as a surfactant, emulsifier, and source of glycerophospholipids found in the cell membrane (such as phosphatidylcholine, phosphatidylethanolamine, phosphatidylinositol, phosphatidylserine, and phosphatidic acid, etc.) | Surfactant, emulsifier, and source of glycerophospholipids. Moisturizer. |
| Moroccan chamomile essential oil (*Tanacetum anmuum*) Range: 0.0001%-20% by volume | Moroccan Chamomile essential oil has the highest amount of chamazulene of all the blue oils, one of the active compounds which possesses potent antioxidant (the ability to scavenge free radicals) (PMID 24980540) as well as anti-inflammatory, antihistamine, anti-pruritic and anxiolytic properties (PMID 26304764) and directly improves dry and sensitive skin. It has weak antimicrobial properties (PMID 20922989) and has been shown to possess anti-cancer activity (see below). Main constituents include sabinene, chamazulene, p-cymene, α-phellandrene, paracymene, β-pinene, β-myrcene, 3,6-dihydrochamazulene, β-eudesmol, eucalyptol, limonene, linalool, α-terpineol, viridiflorol, camphor and parthenolide (which induces apoptosis of stem and progenitor cells per El Haddar et. al. and found that *Tanacetum anmuum* essential oil worked almost as well as mitomycin C at a concentration of 100). For a full list of composite compounds, refer to El Haddar et. al. Be aware there is an essential oil of *Tanacetum vulgare* which is toxic, unlike *Tanacetum annuum*. | A disease with a component of inflammation such as cancer, hay fever, itching, rash, allergies, asthma, bronchospasms, eczema, psoriasis, pain. Anxiolytic properties help with insomnia. Muscle relaxant properties help with excess muscle tension. |
| German chamomile (GC) essential oil (*Matricaria chamomilla* or *Matricaria recutita*) Range: 0.0001%-20% by volume | GC essential oil contains 0.24%-1.9% volatile oil, which contains ~120 secondary metabolites including anti-inflammatory terpenoids, flavonoids, polyphenols, which exert multiple effects, e.g. it is a muscle relaxant, CNS relaxant (PMID 21132119 and 28231151); can attenuate migraine headaches by inhibiting iNOS expression, prohibiting NO release and synthesis (PMID 25238714), found to be significantly effective in treating pain, nausea, vomiting, photophobia and phonophobia in human subjects suffering from migraines in a randomized, double-blind, placebo-controlled crossover study (PMID 29808331) GC compounds naturally penetrate into the skin (PMID 8073060); and inhibit prostaglandin E2 release, attenuate COX-2 enzyme activity and reduces COX-2 mRNA and protein expression, without affecting COX-1 (PMID 19788894) GC terpenoids and flavonoids attenuate leukotriene expression (PMID 19788894) thus exerting effects on contraction of bronchial smooth muscles, stimulation of vascular permeability, attraction and activation of leukocytes (PMID 6311078). GC active compounds significantly lower serum IgE and histamine levels, influencing Th2 cell activation (PMID 20195063). Chamomile preparations have been found to facilitate wound healing, increase the rate of wound contraction, increase wound strength, hydroxyproline content of scar tissue, and is superior to corticosteroids for promoting faster | Insomnia, hay fever, pain, inflammation, muscle spasms, menstrual disorders, insomnia, ulcers, wounds, Diabetes, GI disorders, rheumatic pain, hemorrhoids, lupus, multiple sclerosis, arthritis, Alzheimer's disease, cancer, gout, skin irritations, bruises, burns, canker sores, neuralgia, sciatica, rheumatic pain, mastitis, diaper rash, allergies, conjunctivitis, nasal inflammation, anxiety, nightmares, digestive relaxant, flatulence, indigestion, diarrhea, anorexia, motion sickness, nausea and vomiting, croup, colic; as an emmenagogue and uterine tonic in women; back pain, bedsores, stomach cramps. |

TABLE 1-continued

| Ingredient | Properties | Exemplary Utilities |
|---|---|---|
| | wound healing (PMID 18803230) Oral preparations of chamomile have been shown to attenuate toxic effects of bleomycin on lung tissues in a rodent model of pulmonary fibrosis (PMID 31143217). Chamomile syrup was shown to have a potentially life-saving immune-building effect, as it was able to minimize chemotherapy-induced neutropenia in pediatric leukemia patients (PMID 31921608) Chamomile preparations have been found to be safe and effective for treating colic and diarrhea in infants and children ranging from 2 weeks to 5.5 years, eliminating colic in 57% of 68 infants, and ending diarrhea sooner in 85% of 79 children treated (PMID 17400821) Apigenin is a central benzodiazepine receptor ligand with anxiolytic and slight sedative effects (PMID 7617761) which additionally exerts an antitumor effect in preclinical models of skin, prostate, breast, and ovarian cancer (PMID 21132119) Quercetin, another antioxidant in GC oil with antitumor effects PMID 31880372) the ability to decrease prefrontal cortical GABAergic transmission and alleviates the hyperactivity induced by glutamatergic N-methyl-D-aspartate receptor antagonist MK-801 (PMID 30057312) and has utility for its mild antipsychotic and anti-seizure properties, and neuroprotective effects (PMID 31496698). Other key active compounds in German and Roman Chamomile include α-bisabolol, α-bisabolol oxides A&B, and matricin which is usually converted to chamazulene and other flavonoids which possess anti-inflammatory properties. Of note, chamazulene and bisabolol are very unstable and are best preserved in an alcoholic tincture (PMID 21132119) and it preserves its function even when the blue color is lost with aging. | GC Oil has GRAS status (Generally Recognized As safe), however has prescription drug interaction and may contraindicate drugs metabolized by CYP2D6, CYP1A2, CYP2C9, and CYP3A4. Dilute before using. |
| Roman chamomile (RC) essential oil (*Chamaemelum nobile*) Range: 0.0001%-20% by volume | Anti-inflammatory esters and flavonoids apigenin, luteolin, hispidulin and eupafolin exert antispasmodic effects and instant, transient, moderate relaxation of smooth muscles (PMID 29681854). Apigenin is a central benzodiazepine receptor ligand with anxiolytic and mild sedative effects (PMID 7617761), an effect that is reversible when a benzodiazepine antagonist flumazenil is administered first. Topical applications of chamomile have shown moderate effectiveness in the treatment of atopic eczema, ~60% as effective as 0.25% hydrocortisone cream and after 2 weeks of treatment showed a slight superiority over 0.5% hydrocortisone (PMID6664158) | Decrease hyperactive smooth muscle tone in the GI system, peripheral blood vessels for hypertension and migraine, eczema. |
| Orange essential oil (*Citrus sinensis*) Range: 0.0001%-10% by volume | Orange essential oil has preventative properties against cancer, and also exhibits antitumor properties. Pleasant smelling. Decreased subjective experience of pain in patients with fractures when inhaled (PMID 29123351) and decreased pain when applied topically in a double-blind, placebo-controlled study of elderly patients with knee pain (PMID 18534325). The main active component of orange essential oil is D-Limonene (cyclic monoterpene)— which has been shown to decrease pain in a murine model of neuropathic hyperalgesia/fibromyalgia, changing the expression of Fos gene (a family of transcriptions factors important in cancer and multiple cellular functions) in dorsal horn neurons (PMID 28673718). It has also been shown to be directly cytotoxic to human neuroblastoma cells (PMID 23707744). D-limonene as well as its metabolites limonene-1- | Treatment of pain; preventing cancer as well as stimulating death of tumor cells. Useful in diseases where decreasing inflammation is useful (such as cancer, multiple sclerosis) but activated T cells are beneficial (such as HIV). Useful in diseases where diuresis is beneficial, such as in relieving pain caused by localized tissue swelling or in heart or lung failure where the body is fluid overloaded. Useful in |

TABLE 1-continued

| Ingredient | Properties | Exemplary Utilities |
|---|---|---|
| | 2-diol and perillic acid has been shown to modulate/stimulate T lymphocyte activity and viability (PMID 23059811) by inhibiting production of pro-inflammatory IFN-γ, IL-2, TNF-α, IL-4 and IL-13 by CD3(+) CD4(+) T cells; as well IFN-γ, IL-2, and TNF-α, by CD3(+) CD8(+) T cells. D-limonene and metabolites stimulates activated T lymphocytes to upregulate expression of CD25, CD69 and CD40L on their cell surface, rendering them more capable. D-limonene has a mild diuretic effect that is dose-dependent but only has effect when animals were fluid overloaded, not when they were in a euvolemic state (PMID 20606379), useful in relief of localized swelling. D-limonene is the same as the R(+)-isomer. R(+)-Limonene or D-limonene also has anxiolytic properties (PMID 22995322) which is NOT reversed by flumazenil, indicating a separate pathway outside of benzodiazepine receptors for treating anxiety. D-limonene and other metabolites by yeast Yarrowia (PMID 24688495), as well as by Mortierella minutissima for maximum biotransformation (PMID 15717122). Biotransformation of limonene can occur by bacteria, fungi, yeasts and plants (PMID 12743755) taking one useful compound and creating multiple useful ones as a result. D-limonene has antimicrobial properties which can be enhanced by nano-emulsification and when dissolved in a penetrating carrier such as DMSO (PMID 30042591) thus it follows that nano-emulsification while dissolved in emu oil would also have similar enhanced antimicrobial effects, potentially precluding need for additional preservatives. | treating the anxiety that arises from being in pain. It is useful as an antimicrobial (and thus natural preservative). |
| Frankincense essential oil (*Boswellia serrata*, *Boswellia carteri*, *Boswellia sacra*, *Boswellia frereana*, *Boswellia rivae*, *Boswellia neglecta*, *Boswellia papyrifera* *Boswellia dalzielii*) Range: 0.0001%-30% by volume | Adaptogen—alleviating sleep debt, improving response to stress while limiting negative physiological consequences of prolonged stress. Pain (especially arthritic pain), fatigue, wound healing, diseases involving inflammation including cancer, ulcers; antioxidant properties useful for prevention of cancer and diminishing aging; anti-ulcer and anti-microbial properties. Increases lipid fluidity of cells to enhance absorption of co-administered bioactive products. Useful in the prevention and treatment of infections against bacteria. Useful in protecting against leishmania infestation. Traditional uses include for arthritis, rheumatic arthritis, diarrhea, dysentery ringworm, boils, fevers, skin and blood diseases, cardiovascular diseases, mouth sores, bronchitis, asthma, cough, hair loss, jaundice, hemorrhoids, syphilitic diseases, irregular menses, edema. Helps normalize blood lipids and protects the liver. (PMID 22457547). | Adaptogen—alleviating sleep debt, improving response to stress while limiting negative physiological consequences of prolonged stress. Pain (especially arthritic pain), fatigue, wound healing, diseases involving inflammation including cancer, ulcers; antioxidant properties useful for prevention of cancer and diminishing aging; anti-ulcer and anti-microbial properties. Increases lipid fluidity of cells to enhance absorption of co-administered bioactive products. Useful in the prevention and treatment of infections against bacteria. Useful in protecting against leishmania infestation. Traditional uses include for arthritis, rheumatic arthritis, diarrhea, dysentery ringworm, boils, fevers, skin and blood diseases, cardiovascular diseases, mouth sores, |

TABLE 1-continued

| Ingredient | Properties | Exemplary Utilities |
|---|---|---|
| | | bronchitis, asthma, cough, hair loss, jaundice, hemorrhoids, syphilitic diseases, irregular menses, edema. Helps normalize blood lipids and protects the liver. |
| Myrrh essential oil (*Commiphora myrrh*a, *Commiphora erythraea*, *Commiphora incisa*) Range: 0.0001%-30% by volume | When combined with frankincense, myrrh alleviated neuropathic pain in mice by modulating TRPV1 (PMID 28740739) and also work synergistically with frankincense to treat inflammation, cancer, pain, infection, blood activation (PMID 31450584), and additionally synergizes to penetrate the skin by changing the conformation of lipids and keratin in the skin, increases lipid fluidity of skin cells to allow deeper penetration and also movement of lipid rafts (PMID 31450584) as well as improving blood circulation (PMID 28959837). Helpful in reducing blood pressure (PMID 9292417), reducing inflammation, nervous disorders, hyperlipidemia, ischemia, skin disorders, cancer and relieving chest pain (PMID 26656226, PMID 22388973). Helpful in reducing neuropathic pain (PMID 24621062). Antibiotic properties (PMID 31450584). Myrrh possesses multiple potent anti-cancer properties which are enhanced and synergized with addition of Frankincense (PMID 31450584). Myrrh induces apoptosis and inhibits the proliferation and migration of gastric cancer cells by down-regulating cyclooxygenase-2 expression (PMID 32364228). Myrrh has anti-parasitic properties (PMID 32121352). Myrrh has an inhibitory effect on ICAM-1 adhesion molecule, which is one mechanism by which it has anti-inflammatory effects (PMID 33374825). | Pain, and other diseases with an inflammatory component, including cancer. Has antimicrobial properties. Helpful for acne, antiseptic, athlete's foot, bacterial infections, bedsores, boils, cracked skin, cuts, dermatitis, eczema, fungal infections (athlete's foot, ringworm), healing agent, inflammation, scars, sores, ulcers, weeping wounds, and wrinkles. Helpful in reducing blood pressure, hyperlipidemia, decreasing cardiovascular events. |
| Cinnamon essential oil (*Cinnamomum verum*) Range: 0.0001%-6% by volume | In Traditional Chinese Medicine, cinnamon is used to increase circulation to improve delivery of other medicines to the rest of the body. Additionally, it possesses diuretic effects (PMID 20606379), antioxidant and antiproliferative effects (PMID 31929818), antimicrobial properties (PMID 31926578), anti-inflammatory and anti-diabetic properties (PMID 31901246), decreases visceral/abdominal fat and regulates lipid metabolism (PMID 31869758), repels insects (PMID 31869758), improves blood circulation and transdermal penetration of other medicines admixed with it (PMID 26457698) and treats dysmenorrhea (PMID 26023601) | Treats pain, increases circulation, treats diabetes, has anticancer properties, helpful in any disease process involving inflammation. Slows aging due to antioxidant properties. Insect repellent. |
| Calamus essential oil (*Acorus calamus* or sweet flag) Range: 0.0001%-6% by volume | Wound healing: decreases epithelialization time, increases tensile strength of scar tissue, increase in collagen, hexosamine and hyaluronic acid in full thickness cutaneous wounds in rats as compared to untreated animals (PMID 24991107) anti-cancer, anti-angiogenic properties (PMID 28348970) antimicrobial and antiparasitic properties (PMID 27562598), and insect repellent properties (PMID 26600710) | Wound healing, cancer, antimicrobial properties, insect repellent. |
| Cassia essential oil (*Cinnamonum cassia*) Range: 0.0001%-6% by volume | Anti-inflammatory by regulating succinate/SUCNR1 metabolic signaling pathway, improving rheumatoid arthritis (PMID 31949465) Antimicrobial properties (PMID 31631505) Promotes lung cancer cell death by inhibiting pyruvate dehydrogenase kinase activity, (antiglycolytic pathway) (PMID 30392804). Cassia Oil also possesses analgesic, anti-diabetic, anti-obesity properties; is cardioprotective, cytoprotective, neuroprotective, has immunoregulatory properties, anti-tyrosinase activity (useful in cancer and inflammation)—All from (PMID 31557828) | Anti-cancer, stimulates apoptosis in lung cancer cells, treats diseases with an inflammatory component. |

TABLE 1-continued

| Ingredient | Properties | Exemplary Utilities |
|---|---|---|
| Vanilla Oleoresin essential oil or CO2 extraction (*Vanilla planifolia*) Range: 0.0001%-6% by volume | Vanilla is useful in treating anxiety by lowering serum catecholamine levels while leaving serotonin (feel good hormone) intact; it is useful in treating sleep disorders and nocturia (PMID 32871621). | Useful in treating anxiety, sleep, and nocturia |
| Jasmine essential oil (*Jasmine grandiflorum*) Range: 0.0001%-10% by volume | Anxiolytic and anti-epileptic effect that is comparable to diazepam at 2 mg/kg (PMID 30915314, PMID 28262620), sedative effects useful for treating insomnia, anxiety, significantly decreased heart rate, and an increase in high-frequency activity in autonomic nerves resulting in improved mood in human subjects (PMID 15976995). Improves wound closure rate, healing of open wounds, improved skin thickness over a wound, and decrease in inflammation within a wound (PMID 31916035). Useful in treating pain, digestive issues, and ulcers due to its ability to alleviate muscle spasms, antimicrobial, antiulcer, and antioxidant properties (PMID 25847780) | Anxiety, mood disorders, insomnia, convulsive disorders, epilepsy, alcohol withdrawal, wound healing, ulcers, muscle spasms, antioxidant properties, improves digestion. |
| Lemongrass essential oil and water extract (*Cymbopogon citratus* and *Cymbopogon flexuosus*) Range: 0.0001%-80% by volume | Relief from pain, depression, fever, abnormal muscle tension & spasms, insomnia. Topical antimicrobial. Antioxidant effect protects against cancer (PMID 29854620, 27894219, 22082069, 21089157) and decreases liver stress by increasing liver antioxidant activity (PMID 29389585). Water extracts of kaffir lime leaf:galangal:lemongrass in a 1:2:1 ratio have been shown to upregulate stem cell markers in hepatocytes, to stimulate resolution of steatohepatitis (fatty liver, from overindulgence of lipids and starches which leads to hypercholesterolemia), while maintaining mitochondrial function and architecture, and even correcting blood cholesterol, LDL, HDL and TG levels similar to simvastatin (PMID 31978768). | Anxiety, depression, insomnia, convulsive disorders, increased muscle tension, Has antimicrobial and antioxidant activity useful in preventing cancer. Helpful in improving metabolism, with weight loss, fat metabolism, hyperlipidemia. |
| Galangal root essential oil and water extracts (*Alpinia galanga*, and *Kaempferia galanga*) Range: 0.0001%-80% by volume | Anti-inflammatory, anti-microbial, antioxidant, anti-cancer, anti-proliferative properties, helpful in digestion, inhibits nitric oxide production leading which may lead to smooth muscle dilation or constriction depending on tissue site; useful in treating pain, especially headaches. (PMID 28503054). Water extracts of kaffir lime leaf:galangal:lemongrass in a 1:2:1 ratio have been shown to upregulate stem cell markers in hepatocytes, to stimulate resolution of steatohepatitis (fatty liver, from overindulgence of lipids and starches which leads to hypercholesterolemia), while maintaining mitochondrial function and architecture, and even correcting blood cholesterol, LDL, HDL and TG levels similar to simvastatin (PMID 31978768). Kaempferia galanga possesses anti-microbial, antioxidant, amebicidal, analgesic, anti-inflammatory, anti-tuberculosis, anti-dengue, anti-nociceptive, anti-angiogenic, anticancer, hyperlipidemic, hypopigmentary, osteolysis, larvicidal, insecticidal and mosquito repellent, nematocidal, sedative, sniffing, vasorelaxant and wound healing (PMID 32061673). Alpinia galanga improves mental alertness and sustained attention (PMID 289101196), has anti-cancer properties (PMID 31983172, PMID 33445186), possesses emmenagogue, aphrodisiac, abortifacient, carminative, antipyretic, and anti-inflammatory qualities, and is useful for treating multiple diseases including bronchitis, heart disease, chronic enteritis, renal calculus, diabetes, rheumatism, and kidney disorders (PMID 22015185). | Helpful in diseases which have an inflammatory component, in preventing infection, in reducing antioxidant burden and thus helpful in anti-aging products, helpful in treating pain and digestive issues. Helpful in improving metabolism, with weight loss, fat metabolism, hyperlipidemia, in treatment of cancer. |

TABLE 1-continued

| Ingredient | Properties | Exemplary Utilities |
|---|---|---|
| Kaffir lime leaf or rind essential oil and water extracts (*Citrus hystrix*) Range: 0.0001%-80% by volume | Helpful in improving metabolism, with weight loss, fat metabolism, hyperlipidemia. Water extracts of kaffir lime leaf:galangal:lemongrass in a 1:2:1 ratio have been shown to upregulate stem cell markers in hepatocytes, to stimulate resolution of steatohepatitis (fatty liver, from overindulgence of lipids and starches which leads to hypercholesterolemia), while maintaining mitochondrial function and architecture, and even correcting blood cholesterol, LDL, HDL and TG levels similar to simvastatin (PMID 31978768). | Helpful in improving metabolism, with weight loss, fat metabolism, hyperlipidemia. |
| Xiang mao essential oil and water extracts (*Cymbopogon citratus*) Range: 0.001%-80% by volume | Also known as West Indian Lemongrass, which possesses anti-inflammatory, neuroprotective (PMID 32736056), antibacterial, antiviral, anti-trypanosomal, antifungal (PMID 31470085), anti-proliferative/anti-cancer properties (PMID 29501481) useful for treating muscle soreness, infections, cancer (PMID 20047890), killing mites (PMID 32251453) and preventing infections (PMID 25242268) | Helpful in diseases which have an inflammatory component. Helpful in treating and preventing infections. Helpful in neurodegenerative diseases. Helpful in killing cancer |
| Clove essential oil (*Eugenia caryophyllata*, *Syzygium aromaticum*) Range: 0.001%-30% by volume | Anti-inflammatory, antimicrobial, antifungal, antiviral, antibacterial, antioxidant, anti-cancer, analgesic, facilitates wound healing and dermal fibroblast remodeling, repellent to insects, anesthetic properties (PMID 17380552, PMID 28407719) by inhibiting tissue remodelling protein molecules (collagen-I, collagen-III, M-CSF, tissue inhibitor of metalloproteinase 2 (TIMP-2); downregulates signaling pathways important for inflammation, tissue remodeling, cancer signaling (PMID 28407719). | Helpful in inflammation, preventing or treating infection, anti-aging; improves wound healing, useful in inhibiting cancer pathways, modulates immune system and tissue remodeling. |
| Yuzu essential oil (*Citrus junos*) Range: 0.001%-30% by volume | Anti-carcinogenic (PMID 15884872), neutralizes carcinogenic compounds (PMID 20492298), anti-inflammatory (PMID 25453522), anti-anxiety (PMID 27103924), helpful in treating mood disturbance, PMS, anger, hostility, fatigue (PMID 27103924, PMID 28481623), anti-cancer (PMID 29976894), hypocholesterolemic, anti-diabetic, anti-obesity, platelet aggregation inhibitor, heart failure treatment (PMID 29976894) | Cancer, diseases which involve inflammation, anxiety, mood disturbance, reduction of tension, anger, fatigue, neutralizing effect of carcinogens, helpful in normalizing hypercholesterolemia and hyperlipidemia, helpful in treating diabetes, metabolic syndrome, obesity, heart failure. Functions in inhibiting platelet aggregation (as a blood thinner). |
| Rosemary essential oil (*Rosmarinus officinalis*) Range: 0.001%-30% by volume | Possesses anti-inflammatory (PMID 30328397, PMID 28862678, PMID 30364169), antioxidant (PMID 25002023), neuroprotective properties/enhances cognitive function (PMID 30651162), hepatoprotective properties by enhancing liver detoxification, especially in its ability to metabolize fat and prevent liver steatosis (PMID 25002023), anti-depressant properties (PMID 30364169), Anti-hyperglycemic, helpful in treating diabetes, metabolic syndrome, and obesity by activating PPAR-gamma which lowers blood glucose levels, increasing serum insulin; also inhibits alpha-glucosidase to reduce sugar absorption (PMID 28862678, PMID 30651162), analgesic (PMID 25635991), anti-fungal properties (PMID 32270657), increased hair growth in patients with androgenetic alopecia (PMID 25842469) and wound healing properties (PMID 29343956, PMID 31525200). Improves vascular health by preventing clot and thrombus formation, inhibiting platelet reactivity, inhibiting angiotensin I-converting enzyme (ACE), which leads to less production of chemical which causes arterial constriction, thus enhancing vasodilation and lower blood | Helpful in the treatment of any diseases with an inflammatory component, including cancer, diabetes, metabolic syndrome, obesity, non-alcoholic fatty liver disease, neurodegeneration, eczema, colitis, depression, pain, hair loss, and wound healing. Prevents clot formation and prevents high blood pressure, cardiovascular events including stroke, heart attack. Helpful in prevention and treatment of infections against bacteria, fungi, and viruses. |

TABLE 1-continued

| Ingredient | Properties | Exemplary Utilities |
|---|---|---|
| | pressure (PMID 30651162). Anti-cancer properties by protecting human cell lines against known carcinogens, and by reducing expression of pro-inflammatory genes (PMID 30651162). Multiple phytocompounds in rosemary extract possess antibacterial, antioxidant properties, stimulate organized cell death of cancer cells, inhibit cancer metastases, limits tumor growth, protects liver and kidneys from chemical damage, protects against colitis, antiviral, protects nervous system, protects against atherosclerosis, possesses anxiolytic properties, stimulates bone production while blocking its breakdown, induces insulin sensitivity, possesses antifungal, antidiabetic, and immunomodulatory properties, protects against peptic ulcers, protection against stroke, anti-atopic dermatitis (PMID 30621719). Also prevents cardiac remodeling after myocardial infarction (PMID 30621719). | |
| Eucalyptus essential oil (extracts of leaf, bark, etc.) (*Eucalyptus globulus*, *Eucalyptus radiata*, *Eucalyptus dives*, *Eucalyptus smithii*, *Eucalyptus odorata*, *Eucalyptus bicostata*, *Eucalyptus cinerea*, *Eucalyptus maidenii*, *Eucalyptus sideroxylon*, *Eucalyptus astringens*, *Eucalyptus lahmannii*, Eucalyptus leucoxylon, etc.) Range: 0.001%-40% by volume | Improves wound healing (PMID 29343956), possess antimicrobial, antiseptic, antioxidant, chemotherapeutic, acaricidal, nematicidal properties, in addition to being useful in the treatment of respiratory and gastrointestinal disorders, repelling insects (PMID 28758221). Eucalyptus essential oil has been found to be protective against a number of bacteria, viruses and fungi (PMID 17972131, PMID 22742534, PMID 2274534, PMID 32659315, PMID 28127308) including *S. aureus*, *H. influenzae*, *S. agalactiae*, *S. pyogenes*, *S. pneumoniae*, and *Candida albicans*, *Scopulariopsis brevicaulis*, *Trichophyton rubrum*, *Trichophyton soudanense*, *Microsporum canis*. It is also effective against mycobacterium tuberculosis and methicillin-resistant *staphylococcus aureus*, viruses, and fungi (PMID 20359267). Inhalation by vapor or orally provides benefit for multiple respiratory diseases, including bronchitis, asthma, chronic obstructive pulmonary disease (COPD), increases the frequency with which respiratory tract cilium beat in order to move more secretions, possesses antioxidant properties to counteract reactive oxygen species, inhibition of arachidonic acid metabolic LTB4 and prostaglandin E2 (PGE2) with subsequent improvement in lung function in asthma patients, and also exerts immunomodulatory properties (stimulating phagocytosis by macrophages) without producing pro-inflammatory effects; the effects of eucalyptus oil was blocked by microtubule blocker, meaning that eucalyptus has its effects on the microtubules (PMID 20359267). | Wound healing, Useful in prevention and treatment of infections from bacteria, viruses and fungi, and also from parasitic infestations. Useful in treating respiratory and GI disease such as gastroenteritis, colitis, asthma, COPD. Useful in repelling insects. Useful in stimulating the immune system to clear an infection (such as stimulating macrophages to clear cellular debris). |
| Lemon essential oil (*Citrus limon*, *Citrus limon spatafora*) Range: 0.001%-30% by volume | Stress relief, cytotoxic (against cancer), chemoprotective, anti-obesity, antioxidant, neuroprotective, anti-anxiety, enhances creativity and mood, analgesic, relief from nausea and vomiting during pregnancy, anti-spasmodic, improves attention, concentration, cognitive performance, enhances mood and memory, enhances penetration of skin, antibacterial, antifungal, insect repellant properties, miticidal (PMID 29976894) | As listed on the left. |
| Ravintsara essential oil (includes roots, bark and leaves) (*Cinnamomum camphora*) Range: 0.001%-30% by volume | Alleviates allergic skin inflammatory responses in vitro and in vivo (PMID 31341557). Antimicrobial (antibacterial, antiviral, antifungal, larvicidal properties) (PMID 31562551, PMID 31640286, PMID 32035880, 33304322, PMID 31428342). Anti-inflammatory, and cell membrane stabilizing properties (PMID 33141054) by inhibiting heat-induced hemolysis as well as hypotonic solution-induced hemolysis in vitro, decreases swelling/edema, decreases expression of inflammatory markers (IL1-beta, TNF-alpha). Bronchodilation, anti-tussive, insecticidal, | Useful in reducing contact allergy skin reactions. Useful in preventing and treating infections from bacteria, coccidiomycoses, viruses, fungi as well as repelling insects and killing larvae. Useful in treating diseases with an inflammatory |

TABLE 1-continued

| Ingredient | Properties | Exemplary Utilities |
|---|---|---|
| | antimicrobial, antiviral, antibacterial, anticoccidial, anti-nociceptive, anticancer properties as well as enhances penetration of skin (PMID 23666009, PMID 30582219). Insecticidal and insect repellent properties (PMID 27827929, PMID 27043503, PMID 16230008). Antifungal properties (PMID 18322727). | component. Helps to stabilize cell membrane, thus may be useful in diseases with an abnormal cell membrane, such as spherocytosis. Improves pulmonary congestion, cough, pain, and inhibits cancer. Improves permeability of the skin to other substances. |
| Ravensara essential oil (bark, leaves, stems) (*Ravensara anisate*, *Ravensara aromatica*, *Ravensara crassifolia*, etc.) Range: 0.001%-30% by volume | Antimicrobial, antifungal properties (PMID 2633710). Improves symptoms of nasal congestion and rhinoconjunctivitis when inhaled (PMID 27034695). | Antimicrobial, Antifungal properties. Improves symptoms of nasal congestion and rhinoconjunctivitis when inhaled. |
| Cinnamon Leaf essential oil (*Cinnamomum zeylanicum*) Range: 0.001%-30% by volume | Anti-microbial and anti-parasitic activity, lowers blood glucose, blood pressure, and serum cholesterol, anti-oxidant and free-radical scavenging properties, inhibition of tau aggregation and filament formation (hallmarks of Alzheimer's disease), inhibition of osteoclastogenesis (osteoclasts are responsible for breaking down bone, leading to bone weakness and osteoporosis), protective against gastric ulcers by reducing acid secretion, reduces pain by decreasing inflammation, wound healing properties, hepatoprotective properties with minimal toxic and adverse effects (PMID 24148965). Potent effects in treating diabetes, metabolic syndrome, PCOS (PMID 28962661, PMID 22671971, PMID 31741280, PMID 27618575, PMID 30144878). Anti-cancer effects by facilitating apoptosis (PMID 31195161). Decreases inflammation and has anti-proliferative properties on skin cells by down regulating inflammatory cytokines VCAM-1, ICAM-1, MCP-1, interferon gamma induced protein 10, interferon-inducible T cell alpha chemoattractant, monokine induced by gamma interferon; as well as tissue remodeling molecules such as EGFR, MMP1, plasminogen activator inhibitor 1; and macrophage colony stimulating factor (an immunomodulatory protein molecule); in addition to modulating multiple signaling pathways important in inflammation, tissue remodeling, and cancer biology (PMID 28444928). Along with Litsea cubeba, has cytotoxic activity against the following cancer cell lines: breast adenocarcinoma MCF7, T47D, MDA-MB-231), chronic myelogenous erythroleukemia (K562) and neuroblastoma cell lines (SH-S75Y) (PMID 31713998). | Useful in prevention and treatment of infections against bacteria, viruses, or fungi. Useful in treating diabetes, high blood pressure, elevated blood cholesterol, metabolic syndrome, obesity, polycystic ovarian syndrome (PCOS), helpful in anti-aging, protecting against early dementia by inhibiting formation of the plaques which cause this disease, is protective against osteopenia and osteopenia, helpful in preventing gastric ulcers by reducing acid secretion, decreases pain by decreasing inflammation, useful in facilitating wound healing, and protects the liver from chemical damage. Anti-cancer properties. Useful in killing cancer cells (breast, chronic myelogenous erythroleukemia, neuroblastoma). |
| Thyme essential oil (*Thymus vulgaris*) Range: 0.001%-30% by volume | Antimicrobial properties (antifungal, antibacterial, antiviral) (PMID 25870697, PMID 32008964, PMID 27994215, PMID 30025373). Anticancer properties in vitro and in vivo against breast cancer (PMID 30970626) and cancer in general (PMID 29785774) due to its antioxidant, anti-inflammatory properties. Also has antispasmodic properties, can enhance healthy growth as well as has immunomodulatory properties (PMID 29785774, PMID 29744941). | Useful in prevention and treatment of infections against bacteria, viruses, or fungi. Prevention and treatment of cancer. Treatment of increased muscle tension or spasms. Supports immune function. |
| Rosalina essential oil (*Melaleuca ericifolia*) Range: 0.001%-30% by volume | Hepatoprotective against chemical damage by reducing oxidative stress, inflammation, necrosis, hemorrhage; Rosalina downregulates COX-2 and caspase-3 hepatic expression and thus is protective against liver cancer (PMID 30506741). Component triterpenes demonstrate antiproliferative activity against a | Useful when taken internally in liver and breast cancer, especially in the case of liver metastases. Useful in prevention and treatment of |

TABLE 1-continued

| Ingredient | Properties | Exemplary Utilities |
|---|---|---|
| | malignant breast cancer cell line (PMID 18826277). Antimicrobial properties—against Viruses, bacteria and fungi; has highest inhibitory effects against *Bacillus subtilis* and *aspergillus niger* (black mold) (PMID 14750197, PMID 17449084). | infections against bacteria, viruses, or fungi, especially black mold. |
| Palmarosa essential oil (including aqueous, dichloromethane and methanolic extraction) (*Cymbopogon martinii*) Range: 0.001%-30% by volume | Antimicrobial properties (antiviral, antibiotic, antifungal); treatment of pain and skin conditions; immunomodulatory properties (both pro- and anti-inflammatory) on monocytes via increased TNF-alpha and reduced IL-10 (PMID 24934659). Anti-diabetic properties by inhibition of GLUT2 transporter by geraniol from *Cymbopogon martinii*; and inhibited stress-induced (adrenaline challenge test) release of glucose from the liver; also doubled kidney glycogen content, doubling renal glucose output compared to diabetic control, and prevented post-prandial spikes, improving the lipid profile, HbA1c levels, and renal parameters; with prolonged use over 10 days, this prevented overexpression of GLUT2, resulting in improved blood sugar control (PMID 31737917). Antihelmintic activity (PMID 21820807). Useful for killing 3 main strains of acne bacteria (Type IA, IB, II) by changing structure of the cell wall resulting in cell lysis and changes in bacterial protein production when used in range of MIC 0.7 to 1.6 mg/ml and has anti-inflammatory properties via multiple mechanisms and does not influence *c. acne* population on skin (PMID 30277563). Neuroprotective in an animal model of stroke (cerebral ischemia/reperfusion-induced oxidative stress in rats) when taken 10 d prior at 50 mg/kg or 100 mg/kg—markedly reversing changes and restoring normal levels of lipid peroxidation, superoxide dismutase, catalase, total thiols and glutathione, helpful in neuralgia, epilepsy (PMID 22855942). Bronchodilator, vasodilator, and spasmolytic activities (PMID 25554990). | Useful in preventing and treating infections, pain, in treating diabetes, metabolic syndrome, obesity, stress-induced central adipose deposition, atherosclerosis, and for reducing cardiovascular events. Useful for improving renal function, improving physiologic response to stress, especially in improving glucose regulation. Useful for killing acne bacterium while decreasing inflammation. Potent protection against neurologic sequelae in animal model stroke when taken orally for 10 days |
| Niaouli essential oil (*Melaleuca quinquenervia*) Range: 0.001%-30% by volume | Inhibition of alpha-melanocyte stimulating hormone (alpha-MSH)-induced melanin production and oxidative stress in B15 melanoma cells (PMID 28899502). Mechanisms include reduced melanin content, reduced malondialdehyde, reduced tyrosinase activity, restored antioxidant levels (glutathione, glutathione peroxidase, superoxide dismutase, catalase), reduced DNA damage (PMID 28899502). Mosquito repellant (PMID 27794392, PMID 16642384). Larvicidal properties (PMID 21485381). Antifungal, anti-nematode properties (PMID 19259503). Reduces blood glucose, useful in treating diabetes. | Useful as a safe, non-toxic skin-brightening and whitening agent, as it can decrease hyperpigmentation. Antifungal and antinematode properties, useful in prevention and treatment of infection and infestation. Useful in treating diabetes due to ability to reduce serum blood glucose in a diabetic model. |
| Laurel leaf, fruit, twig, root essential oil (*Laurus nobilis*) Range: 0.001%-30% by volume | Antibacterial, antifungal properties (effective against *staphylococcus aureus*, and partially effective against *pseudomonas aeruginosa* ATCC 9027, *Escherichia coli* ATCC 8739) (PMID 30813368). Larvicidal properties (PMID 30445842) | Useful in prevention and treatment of infections. Useful in killing insect larvae. |
| Litsea leaf, bark, root, fruit essential oil (*Litsea cubeba*) Range: 0.001%-30% by volume | Antimicrobial properties (bacteria, virus, fungi) including *staph aureus* but not against Gram-negative bacteria (PMID 26411035, PMID 29266378). Decreases production of inflammatory chemokines TNF-alpha and cytokine IL-12 in LPS-stimulated dendritic cells, useful in treating contact hypersensitivity, inflammatory diseases, and autoimmune diseases (PMID 27529236). Along with | Useful in prevention and treatment of infections. Useful in treatment of contact hypersensitivity, inflammatory diseases, autoimmune diseases (multiple sclerosis, lupus). |

TABLE 1-continued

| Ingredient | Properties | Exemplary Utilities |
|---|---|---|
| | *Cinnamonum zeylanicum*, has cytotoxic activity against the following cancer cell lines: breast adenocarcinoma MCF7, T47D, MDA-MB-231), chronic myelogenous erythroleukemia (K562) and neuroblastoma cell lines (SH-S75Y) (PMID 31713998). | Useful in killing cancer cells (breast, chronic myelogenous erythroleukemia, neuroblastoma). |
| Lime essential oil (*Citrus aurantifolia*) Range: 0.001%-30% by volume | Anti-obesity, spasmolytic agent, selective acetylcholinesterase and buytrylcholinesterase inhibitor, antioxidant, anti-inflammatory, antibacterial, antifungal, insecticidal (PMID 29976894) | Obesity, muscle tension, improved acetylcholine levels leading to improved cognition in dementia, anti-aging, useful in diseases with inflammatory component, prevention and treatment of bacterial or fungal infections, as use as a natural insecticide. |
| Grapefruit essential oil (*Citrus paradisi*) Range: 0.001%-30% by volume | Anti-obesity, cravings and hunger reducer (when mixed with patchouli oil), antioxidant, anti-inflammatory, antibacterial, antifungal, insecticidal (PMID 29976894) | Obesity, appetite suppressant, anti-aging, useful in treating diseases with an inflammatory component, prevention and treatment of bacterial and fungal infections, as use as a natural insecticide. |
| Mandarin essential oil (*Citrus reticulata*) Range: 0.001%-30% by volume | Antiproliferative, chemoprotective, antioxidant, antibacterial, antifungal (PMID 29976894) | Cancer, anti-aging, prevention and treatment of infection against bacteria and fungi. |
| Kumquat essential oil (*Citrus Japonica*) Range: 0.001%-30% by volume | Antiproliferative, antioxidant, antibacterial, antifungal (PMID 29976894) | Cancer, anti-aging, prevention and treatment of infection against bacteria and fungi. |
| Bergamot essential oil (*Citrus bergamia*) Range: 0.005%-15% by volume | Note that Bergamot modifies normal and pathological synaptic plasticity of nociceptive and neuropathic pain; also modulates perception of pain, and these effects are reversed by local or systemic pretreatment with μ-opioid antagonist naloxone hydrochloride (PMID 26996621) and bergamot oil also seems to exert effects via peripheral cannabinoid and opioid systems. Melanogenic component in suntan preparations, pain relief, peripheral anti-nociceptive, antiallodynic, wound healing, cytotoxic, anti-tumor, neuroprotective, sedative, calming, soothing, anxiolytic, mood enhancer, antioxidant, antibacterial, antifungal, anti-dermatophyte, antimycoplasmal (PMID 29976894) | Peripheral neuropathy, neuropathic pain, useful in stimulating pigment production in sunless tanning preparations, pain relief, wound healing, cancer, protection from neurodegeneration, enhancing sedation, treatment of anxiety, enhancing mood, relief from depression, useful in anti-aging, prevention and treatment of infections. |
| Neroli essential oil (*Citrus aurantium*) Range: 0.001%-30% by volume | Sedative, soothing, calming, motor relaxant, anxiolytic, antidepressant, anti-seizure, anticonvulsant, central and peripheral antinociceptive effects, anti-inflammatory; improves symptoms of menopause and PMS, aphrodisiac; endothelium and smooth muscle-dependent vasodilator; hypotensive, antioxidant, anti-amnesic, antibacterial, antifungal (PMID 29976894) | Useful in treating insomnia, anxiety, increased muscle tension, depression, seizures, convulsions, pain (via both central and peripheral nervous system), improves symptoms of menopause and PMS, low libido, hypertension, hypertension-associated headaches, useful in preventing or treating infections. |

TABLE 1-continued

| Ingredient | Properties | Exemplary Utilities |
|---|---|---|
| Bitter Orange (*Citrus aurantium amara*) Range: 0.001%-30% by volume | Mild sedative, hypnotic, soothing, calming, motor relaxant, sleep inducer, anxiolytic and antidepressant, pain relief, antiseizure and anticonvulsant agent, anti-spasmodic, aphrodisiac, gastroprotective and ulcer healing, digestive disorders treatment, hepatocarcinogenesis suppressant, antioxidant nephroprotective, antibacterial, pimple and acne treatment, antifungal, fumigant and anti-cholinesterase, larvicidal (PMID 29976894) | Useful in treating insomnia, anxiety depression, pain, seizure, convulsions, muscle spasms, depressed libido, gastric ulcers, improving digestion, protection of the gastric lining, neutralizing carcinogens which target the liver, antioxidant protection of the kidneys, antibacterial, treatment of acne, antifungal, improvement of neurocognitive function by increasing acetylcholine; possesses larvicidal properties. |
| Sweet Orange (*Citrus sinensis*) Range: 0.001%-30% by volume | Anticarcinogenic, relaxant, anxiolytic, pain relief, hepatocarcinogenesis suppressant, anti-tumor, antioxidant, food preservative, acne treatment when used with sweet basil oil, antibacterial, antifungal, anti-aflatoxigenic when used at 500 ppm), larvicidal, insecticidal, anthelminthic, promotes growth of tilapia (PMID 29976894) | Useful in neutralizing carcinogens, improvement of anxiety, pain, neutralizing of carcinogens which target the liver, anti-tumor, anti-aging, acne, antibacterial, antifungal, anti-aflatoxin, useful in killing larva, insects, stimulating growth of tilapia, expelling parasitic worms. |
| Orange petitgrain essential oil (*Citrus aurantium*) Range: 0.001%-30% by volume | Antioxidant, antibacterial, antifungal properties (PMID 29976894) | Anti-aging. Useful in preventing and treating bacterial and fungal infections. |
| Peppermint essential oil or water extract (*Mentha piperita*) Range: 0.001%-80% by volume | When inhaled, found to be just as effective as 4% intranasal lidocaine in treating migraine attacks (PMID 31404204). Mild anthelmintic properties (PMID 21820807). Significant antimicrobial, antiviral, antioxidant and antitumor, and antiallergenic properties, relaxes GI tissue, has analgesic and anesthetic effects in the central and peripheral nervous system, possesses immunomodulating actions and chemopreventive potential, helpful in irritable bowel syndrome (PMID 16767798). Improves cognitive performance, attenuates fatigue, improves concentration (PMID 30087294). Possesses high antiviral activity against HSV1 and HSV2 (Herpes Simplex Virus) if applied to cells prior exposure to adsorption of the virus but has no effects after penetration into the host cell (PMID 31195752). Has antifungal properties (PMID 31195752). | Migraine. Useful in treating parasitic worm infestations. Useful in preventing or treatment of infections from bacteria, viruses and fungi. Helpful in improving ease of breathing. Useful in treating pain and cancer. Improves cognitive function and focus. Protects against herpes virus infection when applied prophylactically. |
| Spearmint essential oil (*Mentha spicata*) Range: 0.001%-80% by volume | Helpful in treatment of osteoarthritic pain, in prevention of flatulence (PMID 28107842). Possesses anti-androgenic properties, thus useful in treating polycystic ovarian syndrome (PCOS)—including reducing weight, testosterone level, ovarian cysts, atretic follicles, and increases Graafian follicles in an animal model of PCOS, by inhibiting testosterone and restoring follicular development in ovarian tissue (PMID | Treatment of pain, osteoarthritic pain, flatulence, PCOS, metabolic syndrome, diabetes. Useful in anti-aging due to antioxidant properties. |

TABLE 1-continued

| Ingredient | Properties | Exemplary Utilities |
|---|---|---|
| | 29399556). Antioxidant properties (PMID 31382468) able to scavenge free radicals and mitigate lipid peroxidation. Also enhances endogenous antioxidant function (increases endogenous glutathione production) (PMID 31382468). | |
| Wintergreen essential oil (*Gaultheria procumbens*) Range: 0.001%-5% by volume | Treatment of pain, especially osteoarthritic pain (PMID 28107842). Along with coriander and frankincense, possesses anti-leishmanial properties (parasite) (PMID 30934998), insecticide properties (PMID 29029320, larvicidal properties against mosquito larvae (PMID 26528914). Improves penetration of skin for other bioactive and medicinal compounds (PMID 29052396) by reducing skin barrier function and enhancing transdermal absorption of lipophilic and hydrophilic drugs. Oil of wintergreen (methyl salicylate) 5 ml is equivalent to 7000 mg of salicylate or 21.7 adult aspirin tablets (PMID 11335011), thus care should be used in formulating doses appropriate for pediatric, adult, and geriatric populations. | Antiparasitic properties against leishmania and larvicidal against mosquito larvae. Improves transdermal penetration of skin. Topical treatment of pain, especially osteoarthritic pain. |
| Coriander seed essential oil, Coriander seed extract (*Coriandrum sativum*) Range: 0.001%-80% by volume | Possesses antioxidant, antimicrobial and antibiofilm activity of coriander (PMID 32143314, PMID 32143314) including antifungal properties (PMID 31142010). Along with essential oil of frankincense and wintergreen, coriander seed derivatives possess anti-leishmanial properties (leishmania parasite) (PMID 30934998). Possess antimicrobial, antioxidant, antidiabetic, anxiolytic, antiepileptic, antidepressant, antimutagenic, anti-inflammatory, anti-dyslipidemic, antihypertensive, neuroprotective and diuretic properties (PMID 23281145). | Useful in prevention and treatment of infections from bacteria, viruses and fungi. Possess antiparasitic properties (leishmania). Useful in treating diabetes, anxiety, epilepsy, depression, cancer, inflammation, hyperlipidemia, hypertension, protecting neurons, and alleviating edema due to diuretic properties. |
| Gingergrass essential oil (*Cymbopogon martinii* var. *sofia*) Range: 0.001%-50% by volume | Exerts immunomodulatory and anti-inflammatory properties on human monocytes (PMID 24934659). Has antimicrobial (bacteria, fungus, virus) properties (PMID 32684097, PMID 30277563). Useful in repelling mosquitoes (PMID 15119079). | Useful in preventing and treating infections, pain. Useful for killing acne bacterium while decreasing inflammation. Repels mosquitoes. |
| Bergamot mint essential oil (from stems, leaves and flowers) (*Mentha citrata*) Range: 0.001%-50% by volume | Antioxidant properties, cytotoxic to colon cancer cells (PMID 31749482, PMID 21646282). Mild insect repellent, larvicidal, and pupicidal properties (PMID 21338379). | Useful in anti-aging, and cancer. Mild insect repellent, larvicidal and pupicidal properties. |
| Lemon balm essential oil (*Melissa officinalis*) Range: 0.001%-30% by volume | Possesses antioxidant properties (PMID 27620926 and PMID 30045422), helpful for improving serum biomarkers of oxidative stress, inflammation and lipid profile (PMID 30045422) anxiolytic properties and improves cognition and focus (PMID 25360512), improves sleep disruption in menopausal women (PMID 24199972), improves skin elasticity and reduces arterial stiffness due to decrease in protein glycation (PMID 28367927) | Anxiety, improves concentration, improves sleep disruption in menopausal women |
| Pine needle essential oil and extract (*Cedrus deodara*, *Pinus brutia*, *Pinus halepensis*, etc.) Range: 0.001%-30% by volume | Frankincense, pine needle and geranium essential oils suppress tumor progression (PMID 29115548, PMID 29434792, PMID 25293350, PMID 32523794). Possesses antioxidant (PMID 31538201), antimicrobial (PMID 22757704, PMID 32013183, PMID 332303819) and anti-inflammatory (PMID 31659812, PMID 30018892) however extracts of Ponderosa Pine has abortifacient properties and thus will be avoided (PMID 1526928), as well as neuroprotective effects (PMID 28642096). | Cancer, infection, any diseases involving inflammation |

TABLE 1-continued

| Ingredient | Properties | Exemplary Utilities |
|---|---|---|
| Geranium essential oil (*Pelargonium graveolens*) Range: 0.001%-30% by volume | Frankincense, pine needle and geranium essential oils suppress tumor progression (PMID 29115548). Geranium triggers cell cycle arrest and apoptosis in cancer cell lines (PMID 30914034), possesses antibacterial and antifungal activity, is useful in neuropathic pain (PMID 30000892), useful in treating diabetes as it reduces serum blood glucose and improved serum antioxidant status when administered orally (PMID 22734822), possesses mild sunscreen properties (PMID 30251317) to protect skin from sunburn. | Cancer, prevents infection, helpful in treating neuropathic pain, diabetes. Useful for mild sunblock properties. |
| Wang-Cho-Pi (Korean lime tree) essential oil and extract (*Zanthoxylum coreanum nakai*) Range: 0.001%-10% by volume | *Zanthoxylum coreanum nakai* essential oil and extracts have been shown to inhibit mast cell degranulation and reduce the level of IL-4, a key inflammatory factor in allergy symptoms (PMID 30618741). Mechanisms include suppressing activation of NF-kB, inhibiting NF-kB p65 translocation into the nucleus, inhibiting inflammatory markers TNF-alpha, IL-6, and NO, downregulating protein levels of iNOS and COX-2; and down-regulating phosphorylation of MAPK signaling cascade despite an inflammatory milieu. | Most useful in allergic inflammatory diseases. |
| Winged prickly ash essential oil and extract (*Zanthoxylum armatum*) Range: 0.001%-10% by volume | *Zanthoxylum armatum* possesses antimicrobial, antiviral, antioxidant, anti-inflammatory, anti-tumor, hepatoprotective, insecticidal properties (PMID 30166217, PMID 33289429) as well as lipid and serum glucose lowering properties useful in treatment of hyperlipidemia, diabetes, metabolic syndrome, obesity, stroke and cardiovascular disease (PMID 29463309, PMID 33390134). Mechanisms include inhibiting alpha-glucosidase, leading to decrease in fasting blood sugar levels (PMID 29463309). Possesses stomachic, carminative and anthelminthic properties (PMID 30166217). | Antimicrobial, antioxidant, useful in treatment of diseases of inflammation, diabetes, cardiovascular disease, metabolic syndrome, hyperlipidemia, obesity, stroke, cancer. Helpful in protecting the liver. |
| Carrot seed oil and extract (*Daucus carota*) Range: 0.001%-99% by volume | Shown to have high repellent activity against mosquitoes when applied topically (PMID 31442148). Has antifungal properties (PMID 31489671) and mild sun protection factor SPF value 6.92 PMID 29737890. | Useful in repelling mosquitoes, treating or preventing fungal infections, or in formulations as a mild sunscreen. Also useful as a skin moisturizer. |
| Blackberry seed essential oil and extract (supercritical carbon dioxide extraction, hexane, ethanol, water distillation) (*Rubus fruticosus*, *Rubus ursinus*, etc.) Range: 0.001%-99% by volume | Antioxidant properties (PMID 28098355). Moisturizer and serves as a carrier oil. | Anti-aging properties. Moisturizer and serves as carrier oil. |
| Blueberry seed essential oil and extract (*Vaccinium corymbosum*, *Vaccinium uliginosum*, *Vaccinium virgatum aiton*, *Vaccinium ashei*, *Vaccinium angustifolium*, etc.) Range: 0.001%-99% by volume | Antioxidant properties (PMID 32363872, PMID 32059466). Moisturizer and serves as carrier oil. | Anti-aging properties. Moisturizer and serves as carrier oil. |
| Raspberry seed essential oil and extract (*Rubus idaeus*) Range: 0.001%-99% by volume | Antioxidant properties. Moisturizer and serves as carrier oil. Dietary supplementation modulates liver functions, inflammatory state, and lipid metabolism in animal models (PMID 26108544) | Anti-aging properties. Improves liver antioxidant status, helps to neutralize an inflammatory state, and improves lipid metabolism. Moisturizer and serves as carrier oil. |
| Turmeric essential oil and extract (*Curcuma longa*, *Curcuma zedoaria*, | Possesses powerful anti-inflammatory properties, as well as hepatoprotective properties, antispasmodic properties, improves bile secretion (PMID 2062949). Antioxidant, | Anti-aging, improves liver function, treatment of muscle cramps, pain, cancer, |

TABLE 1-continued

| Ingredient | Properties | Exemplary Utilities |
|---|---|---|
| *Curcuma aeruginosa*, *Curcuma zanthorrhiza*, *Curcuma aromatica*, *Curcuma phaeocaulis*, *Curcuma amada*, *Curcuma caesia*, etc.) Range: 0.001%-70% by volume | anti-cancer, antimicrobial, anti-neoplastic properties (PMID 26528921, PMID 27213821). Useful in oral and topical treatment of acne, alopecia, atopic dermatitis, facial photoaging, oral lichen planus, pruritus, psoriasis, radiodermatitis, and vitiligo (PMID 27213821). Non-mutagenic, nongenotoxic, safe for use during pregnancy however may cause GI upset at high doses but is GRAS (PMID 29480523). Helpful in treating diabetes, metabolic syndrome and obesity (PMID 29624265). Helpful in treating pain (PMID 27078813), protecting the liver (PMID 30947655), preventing fungal infections (PMID 30947655), reducing blood pressure (PMID 30947655), and neuroprotective (PMID 30947655), improves wound healing, improves arthritic pain, anti-tumor properties (PMID 30947655) anti-hyperlipidemic (PMID 30200410), treatment of GI disorders (PMID 30200410). | useful in the prevention and treatment of infections, skin conditions including acne, alopecia, atopic dermatitis/eczema, photoaging, oral lichen planus, pruritic skin, psoriasis, dermatitis, vitiligo, diabetes, metabolic syndrome, obesity, cardiovascular disease, treating high blood pressure and or hypertension, protects cognitive function, improves wound healing, reduces serum lipids, and inflammatory GI diseases. |
| Black seed essential oil, Black cumin essential oil and extract (*Nigella sativa*) Range: 0.001%-60% by volume | Useful in the treatment of pain, especially that of rheumatoid arthritis (PMID 30097124), anti-inflammatory properties useful in normalizing liver enzymes, hyperlipidemia, insulin and fasting blood sugar levels (PMID 31890671, PMID 31152309), improves weight loss efforts (PMID 31152309) by limiting inflammation which causes upregulation of signaling molecules such as adiponectin which has anti-diabetic, anti-inflammatory, anti-atherogenic, and cardioprotective effects to improve energy metabolism; while also downregulating inflammatory molecules such as TNF-alpha. Mechanisms include restoring normal expression levels of DNMT3A and HDAC1, which are altered under conditions of inflammation; and limiting pro-inflammatory cytokine production (PMID 31878334). When injected intra-articularly was found to protect cartilage from degeneration in early stages of osteoarthritis (PMID 3145944). Helps to convert metabolically unhealthy white fat into beige fat (PMID 32512788) which improves metabolism and promotes weight loss, healthy lipid levels. Possesses neuroprotective properties (PMID 316388880). Applied topically can ameliorate vitiligo appearance and progression (PMID 31025474). Protects multiple organs against side effects of chemotherapy (PMID 29223554, PMID 30888204, PMID 28287318, PMID 31781612, PMID 31453801, PMID 29854586) and against gastric carcinoma (PMID 12881014), breast cancer (PMID 30678630, PMID 24098377) and limits cancer cell proliferation (PMID 31622301). Treats asthma, diarrhea (PMID 12722128). Possesses antipyretic properties, antimicrobial properties (PMID 12722128). Decreases blood pressure and enhances respiratory function (PMID 12722128). Induces increase in hemoglobin, packed cell volume, possesses cytoprotective and antioxidant properties (PMID 12722128). Possesses immunomodulatory and immunotherapeutic properties—specifically by augmenting T-cell and natural killer cell-mediated immune responses, as well as anti-microbial and anti-tumor properties (PMID 16275613) | Cancer, hypertension, diarrhea, rheumatoid arthritis, degenerative osteoarthritis, chronic pain, fibromyalgia, kidney stones, hyperlipidemia, non-alcoholic fatty liver disease (NAFLD), asthma, vitiligo, obesity, potentiates weight loss efforts. |
| Garlic essential oil and extract (*Allium sativum*) Range: 0.001%-50% by volume | Anti-inflammatory properties by inhibiting NF-kappa B activation, iNOS and COX-2, useful in treating pain, stiffness associated with osteoarthritis (PMID 30651162). Improves cardiovascular health and endothelial function by reducing atherosclerotic plaques, suppressing inflammatory cell adhesion to | Treats pain, any diseases with an inflammatory component including diabetes, cardiovascular disease, stroke, |

TABLE 1-continued

| Ingredient | Properties | Exemplary Utilities |
|---|---|---|
| | endothelial cells, increases blood flow and circulation, downregulating inflammatory markers such as CRP, plasminogen activator inhibitor-1, LDL-C, and reduced carotid intima-media thickness progression in patients with coronary artery diseases; lowers serum cholesterol, triglycerides, but not LDL or HDL; lowers blood pressure by stimulating NO and inhibiting ACE activity; while garlic-derived organic polysulfides are converted by red blood cells into hydrogen sulfide gas which leads to vasorelaxation via vascular smooth-muscle cell signaling pathway to further reduce blood pressure; can reduce systolic blood pressure by 15 points and diastolic blood pressure by 9 points; has antithrombotic and anticoagulant properties because garlic inhibits platelet aggregation by inhibiting COX-1 activity and thromboxane A1 formation; also activates fibrinolytic activity and is able to dissolve small clots only in unhealthy patients but not in healthy controls. Garlic lowers blood glucose and thus is helpful in treatment/management of diabetes, metabolic syndrome, and obesity by increasing insulin sensitivity as well as total secretion, decreasing triglyceride levels. Garlic protects against ischemic stroke and improves memory and learning by protecting neurons from A-beta-induced neurotoxicity and apoptosis and prevents cognitive decline associated with Alzheimer's Disease. Garlic possesses immunomodulatory activity by stimulating lymphocyte proliferation and release of interferon-gamma to enhance phagocytosis by macrophages and enhancing killer-T-cell activity (PMID 30651162) | hypertension/high blood pressure, improves blood flow and circulation, useful in treating hyperlipidemia, hypercholesterolemia, useful in dissolving small clots and preventing clot formation, treats metabolic syndrome, diabetes, obesity, and protects against cognitive decline. Enhances memory and learning, as well as stimulating activity and proliferation of immune cells and stimulates their function to fight infections and cancer. |
| Wolfberry (Goji berry) seed essential oil, aqueous extract of whole fruit (*Lycium barbarum, Lycium chinense*) Range: 0.001%-50% by volume | Antioxidant properties (PMID 28407975). Water extract possesses anti-tumor, antioxidant, antidiabetic, protective against radiation, antiviral, blood lipid lowering, anti-fatigue, anti-aging, anti-inflammatory, and immunomodulatory properties (PMID 31030757) | Goji berry seed oil is useful for an antioxidant rich carrier oil and or moisturizer. Helpful in treating acute liver injury, alcoholic liver injury, nonalcoholic fatty liver disease, performance impairment, brain injury, retinal degeneration, stroke and Alzheimer's Disease. |
| Alcohol (190-200 proof) | Used in preserving some of the more easily of Moroccan, German, and Roman chamomile (e.g. bisabolols) degraded compounds found in the essential oils | Preservative, improves solubility and stability of phenolic compounds |
| Pomegranate seed oil and extract (*Punica granatum*) Range: 0.0001%-6% by volume | Pomegranate seeds, fruit, skin, juice and oil all have therapeutic benefits—anti-inflammatory, anti-proliferative, anti-tumorigenic properties affecting multiple signaling pathways universally implicated in all cancers but specifically showing promise in the prevention and treatment of skin, breast, prostate, lung, and colon cancers (PMID 28125044) | Diseases with an inflammatory component, including cancer. Antioxidant properties slow the process of aging and prevent cancer. |
| Ginger essential oil, ethanolic extract, water extract (*Zingiber officinale*) Range: 0.0001%-80% by volume | In Traditional Chinese Medicine, the use of ginger in any formulary is to improve circulation in general, but also to improve circulation of medicine into the correct meridian. This latter effect is greatly enhanced with the addition of licorice root (Personal communication, Dr. Hu-Shen Wang, L.Ac. M.S., Ph.D.). At least one component of Ginger Oil, zingerone exhibited a mild diuretic effect that was observed only when at a dose of 30 mg/kg in normal mice (PMID 20606379). Possesses gastroprotective (PMID 23612703), improves metabolism and metabolic syndrome (PMID 28505392), antiviral properties (PMID 23123794), anti-inflammatory properties | Useful in improving circulation, metabolism, digestion, helps with headaches, anti-emesis, pain, male infertility, congestive heart failure (due to diuretic properties). |

TABLE 1-continued

| Ingredient | Properties | Exemplary Utilities |
|---|---|---|
| | (PMID 17950516) useful in treating pain and improving circulation (PMID 17950516), improves semen quality (concentration, viability, motility and morphology) (PMID 31012134). Ethanolic extracts of ginger are helpful in improving metabolism, treating hyperlipidemia, and useful in weight loss (PMID 32064135). Water extracts of ginger is protective against gastric cancers (PMID 31155951). | |
| Licorice extract (*Glycyrrhiza uralensis*) Range: 0.0001%-80% by volume | In Traditional Chinese Medicine, the use of ginger is to improve circulation and licorice is for helping to deliver herbal medicine into the appropriate meridians. Together, ginger and licorice serve to circulate the medicine as well as deliver medicines to tonify the meridians that need strengthening (Personal communication, Dr. Hu-Shen Wang, L.Ac. M.S., Ph.D.). The active component of licorice (glycyrrhizin) synergizes with emu oil to exert a stronger anti-inflammatory effect by modulating inflammatory markers PPARγ and TNFα in an animal model of ulcerative colitis (PMID 25560991) | Useful in treating disorders involving inflammation. |
| *Bupleurum* extract (*Bupleurum chinense*) Range: 0.0001%-80% by volume | *Radix Bupleurum* is a mainstay in Traditional Chinese Medicine, safely used for thousands of years when in the correct proportion with other herbs and in appropriate dose (Personal communication, Dr. Hu-Shen Wang, L.Ac. M.S., Ph.D.). There are over 281 components isolated from *Radix bupleuri*, including 15 flavonoids, 430 lignins, 12 phenyl propanol derivatives, 66 triterpenoid saponins, and volatile oils, which have antipyretic, antiviral, anticonvulsant, antitumor, sedative, analgesic, antitussive, hepato- and nephron-protective properties, anxiolytic as well as immunomodulatory properties (PMID 29956627) | |
| Coenzyme q10 Ubiquinol, Ubiquinone Range: 0.0001%-30% by weight | Ubiquinol = an electron-rich (reduced) form of coenzyme Q10, one of the 3 forms of coenzyme Q10 (fully oxidized (ubiquinone), partially reduced (semiquinone or ubisemiquinone) and fully reduced (ubiquinol). Ubiquinone is the most bio-available form of coenzyme Q10, which is important in cellular energy production as part of the electron transport chain in the mitochondria where the energy for the body is produced. Possesses antioxidant properties and improves renal function (PMID 20878200 and PMID 24151980). | Useful as a supplement in patients with cardiovascular compromise. Useful in improving energy profile and metabolism to address obesity, metabolic syndrome, and diabetes. Useful in improving skin cell function when applied topically. |
| Food-Grade Diatomaceous Earth (FGDE) Range: 0.0001%-90% by weight | FGDE are biocompatible, nontoxic porous biosilicates skeletal remains of unicellular diatom microalgae that are tiny (nano microns) long which can be used as micro-shuttles in drug delivery systems that have been demonstrated capable of opening intercellular tight junctions (PMID 31618958) - particularly useful in delivery of substances with poor water solubility and low oral bioavailability such as quercetin (PMID 31496698), prolonging drug delivery (PMID 316618958) and particularly useful in the treatment of metastatic cancer (PMID 31330820), which requires infiltrating the intracellular signaling pathways taken over by cancer (PMID 25239399). FGDE is safe to consume. It passes through the digestive tract unchanged and does not enter the bloodstream. Inhalation of FGDE can cause silicosis lung disease, thus workers must be appropriately masked when working with it. | |
| Dead Sea Salt Range: 0.0001%-30% by weight | Refer to (PMID 22503590) for scientific evidence of the therapeutic effects of dead sea treatments: a systematic review. Dead sea salts have a good safety profile, useful for rheumatologic diseases and psoriasis, do not increase blood pressure. The Dead Sea is the | Psoriasis, Eczema, Acne, Allergies, Hair Loss, Osteoarthritis, Rheumatoid Arthritis, Dry Skin, Stress, Muscle Soreness, |

TABLE 1-continued

| Ingredient | Properties | Exemplary Utilities |
|---|---|---|
| | world's deepest and highest salinity lake, with 9 times the minerals and salts than sea water, simply due to gravity pooling the minerals into the deepest lake thus collecting all minerals. Readily replenishes trace minerals required for human health. Readily receives and reflects light and even gamma radiation for over 336h after initial optical stimulation (PMID 28495302), thus the perfect vehicle for receiving sound and optical energy prior to dissolution into solvent. Dead sea water has been shown in in vitro and ex vivo human skin organ cultures to stimulate the expression of barrier-related proteins filaggrin, involucrin and transglutaminase, thus strengthening the structural integrity of skin; it also stimulated secretion of β-endorphin which promotes feelings of well-being, while simultaneously attenuating the expression of inflammatory and irritation-related cytokines (PMID 30903724) | Chronic Pain, Restless Leg Syndrome, Insomnia |
| Organic pea protein Range: 0.0001%-30% by weight | Provides all amino acids, including essential branched chain amino acids required for muscle growth; decreases muscle damage | Rebuilding muscle, bone, connective tissue |
| Organic brown rice protein Range: 0.0001%-30% by weight | Provides all amino acids, including essential branched chain amino acids required for muscle growth; decreases muscle damage | Rebuilding muscle, bone, connective tissue |
| Sea Kelp Bioferment (extract of fermented seaweed) (*Macrocystis pyrifera*, *Nereocystis luetkeana*, *Laminariales*, other kelp, etc.) Range: 0.01%-40% | Moisturizer, humectant, source of antioxidants, with anti-inflammatory properties, vitamins, minerals especially trace minerals such as iodine, copper, selenium, zinc which are important cofactors for cellular function, metabolism, and regeneration. | Antioxidant, anti-inflammatory properties, provides cofactors important for cellular function, metabolism and regeneration. |
| N-Acetyl Cysteine (NAC) Range: 0.0001%-50% by weight | One of 3 most abundant amino acids in pre-collagen and collagen. Antioxidant that completely blocks Reactive Oxygen Species (ROS) protecting from cancer, reducing fatigue (PMID 21715129) | Rebuilding collagen (<1% by volume). Recharging liver glutathione (<50% by volume) |
| Glycine: Range: 0.0001%-50% by weight | One of 3 most abundant amino acids in pre-collagen and collagen | Rebuilding collagen (<1% by volume). Useful for promoting restful sleep, or as an anxiolytic (<50% by weight) |
| L-proline: Range: 0.0001%-50% by weight | One of 3 most abundant amino acids in pre-collagen and collagen | Rebuilding muscle, bone, connective tissue (<1% by weight). |
| Vitamin A: Range: 0.0001%-50% by weight | Essential for amino acid utilization. Critical for wound healing (PMID 31697447), regulation of gene transcription which regulate reproduction, embryogenesis, vision, growth, differentiation and proliferation of stem cells, maintenance of skin cell integrity, immune function (PMID 26565606) | Rebuilding muscle, bone, connective tissue (<1% by weight). |
| Vitamin B3 (niacinamide): Range: 0.0001%-50% by weight | Essential for amino acid utilization. Possesses anti-pruritic, antimicrobial, vasoactive, photo-protective, sebostatic, and pigment lightening effects (PMID 24993939, PMID 29405129). | Rebuilding muscle, bone, connective tissue (<1% by weight). |
| Vitamin B6: Range: 0.0001%-50% by weight | Serves as a coenzyme catalyzing more than 150 enzymes regulating metabolism and synthesis of all macromolecules, heme and other bioactive metabolites (PMID 29477221). Possesses antioxidant properties, synthesis of neurotransmitters, protection against advanced glycation end-products and thus against aging (PMID 20110903). | Important antioxidant required for proper metabolism, preventing inflammation, cardiovascular disease, healthy aging and cancer. |
| Vitamin C: Range: 0.0001%-50% by weight | Essential for amino acid utilization and collagen formation. Powerful antioxidant, electron donor, and cofactor to many enzymatic reactions (PMID 26808119), important in metabolism, proper cognitive function (PMID 28867798), proper immune function (PMID 29099763), skin health (PMID 28805671), and prevention of coronary heart disease, stroke and cancer (PMID 29477224). | Rebuilding muscle, bone, connective tissue (<1% by weight). |

TABLE 1-continued

| Ingredient | Properties | Exemplary Utilities |
|---|---|---|
| Vitamin D:<br>Range: 0.0001%-50%<br>by weight or volume | Essential for amino acid utilization; low levels of serum 1,25(OH)2D (active vitamin D) is associated with psoriasis (PMID 31803350) and topical application of calcipotriene improves chronic plaque psoriasis (PMID 10753146). Vitamin D2 and D3 are precursors of hormones with important roles in regulating concentrations of calcium and phosphates (PMID 22716179), is important in proper immune function (PMID 25912039), optimizing strength in human muscles (PMID 27379960), preventing cardiovascular disease and hypertension (PMID 26768241). Important in proper skin barrier formation and regulation of the innate immune system which controls immunologic response to allergens and microbial pathogens (by improving innate antimicrobial peptides such as cathelicidin, LL-37 and beta-defensin) (PMID 27918470). Integral for synthesis, metabolism and activity of a healthy skin barrier, without which cellular proliferation, differentiation and apoptosis is impaired, making the skin more prone to development of psoriasis and eczema (PMID 29306952) and acne (PMID 31322523) | Rebuilding muscle, bone, connective tissue (<1% by weight). Ameliorates psoriasis (0.005% calcipotriene by v/v; or 1,25-dihydroxyvitamin D3 0.005%-5% in human mimicry oil blend); same ranges for insomnia/fatigue, cancer. Eczema, Psoriasis, acne and other diseases with a disrupted skin barrier. |
| Vitamin E:<br>Range: 0.0001%-50%<br>by weight or volume | Powerful antioxidant (PMID 20399614) anti-inflammatory (PMID 32204073), especially when coupled with Vitamin A (PMID 32204073), improves skin clarity (PMID 31975502), anti-tumorigenic, photoprotective, skin barrier stabilizing properties (PMID 17719081). Upregulates gene expression of keratinocyte differentiation markers (PMID 33070130). | Eczema, Psoriasis, diseases of the skin barrier, antioxidant, anti-inflammatory |
| Vitamin K2 (MK7):<br>Range: 0.0001%-50%<br>by weight or volume | Improves weight loss efforts in a subset of patients who respond to supplementation with Vitamin K2 MK7 with increased carboxylation of osteocalcin (PMID 28952607)—the pts had reduced body weight, abdominal and visceral fat. Prevents age-related deterioration of trabecular bone microarchitecture in postmenopausal women (PMID 27625301), reduces progression of atherosclerosis in chronic kidney disease patients (PMID 26176325), important cofactor for blood coagulation in the liver, for preventing arterial calcification, for general cellular metabolism (PMID 30609653). MK7 form is the most bioactive form as it is carboxylated and can readily promote hemostasis, useful in regulating signaling cascades important in osteoporosis, atherosclerosis, cancer and inflammatory diseases without risk of negative side effects or dosing (PMID 30791399). Only the MK7 form of Vitamin K2 can promote gamma-carboxylation of extrahepatic vitamin K-dependent proteins (VKDPs), osteocalcin, and the matrix Gla protein at a nutritional dose around the recommended daily intake. MK7 has a higher bioavailability and longer half-life than other vitamin K homologs. MK7 increases bone mineral density by facilitating signaling cascades which improve translocation of calcium from the serum into the bony matrix, and promotes the quality and strength of bone and collagen (PMID 32244313) | High vitamin K2 intake is supportive of reducing body weight, abdominal and visceral fat in patients who increase carboxylation of osteocalcin as a result of supplementation. |
| Gallic Acid (GA-3,4,5-trihydroxybenzoic acid, found in grape seeds, rose flowers, sumac, oak and witch hazel)<br>Range: 0.001%-50% by weight or volume | Plant polyphenol with strong inhibitory properties in vitro and in vivo against cancer (PMID 23501608) by inhibition of NFKB, Akt, COX, ribonucleotide reductase and GSH pathways; and also activates ATM kinase signaling to prevent carcinogenesis (PMID 23501608). Useful in preventing and treating acne (PMID 32390309, PMID 30617549). Powerful antioxidant, anti-inflammatory, anti-microbial, anti-cancer activities (PMID 30657034) | Cancer, Acne, antioxidant, anti-inflammatory, antimicrobial. |

TABLE 1-continued

| Ingredient | Properties | Exemplary Utilities |
|---|---|---|
| Grape Seed Extract (*Vitis vinifera*) Range: 0.001%-50% by weight or volume | Main component is resveratrol, and other polyphenols and proanthocyanidins. Anti-microbial properties (PMID 31760860), anti-obesity properties by converting white fat to beige fat (PMID 32114568), anti-hypertension properties by altering function of vascular endothelial cells (PMID 31757033, PMID 29683391), improves glycemic control, lowers serum lipoproteins, decreases inflammation, and body weight (PMID 31880030), decreases appetite via altering neuropeptide Y signaling (PMID 31713941), possesses powerful anti-inflammatory properties by altering NFKB signaling and alleviates arsenic-induced lung damage (PMID 30869553), increases bone callus formation and mechanical strength (PMID 31277691), Improves wound-healing (PMID 31003677), ameliorates bleomycin-induced pulmonary fibrosis in mouse model (PMID 2830065), reduces atherosclerosis (PMID 33456610), reduces oxidative damage and apoptosis in kidneys in an animal model of sodium-fluoride-induced damage (PMID 32641209); due to proanthocyanidins. | Useful in treating and prevention of infections, improving metabolism, reducing obesity, improving hyperlipidemia, fatty liver, diabetes, anti-aging, wrinkles, hypercholesterolemia, hypertriglyceridemia, reducing high blood pressure/hypertension, improving glycemic control, decreases inflammation, useful in the treatment of any disease of inflammation, decreases body weight by altering neuropeptide Y signaling, useful in treating osteoporosis, preventing chemotherapy-induced lung and tissue damage, decreases atherosclerosis. |
| Grape Skin Extract (*Vitis vinifera*) Range: 0.001%-50% by weight or volume | Main component is resveratrol, and other polyphenols and proanthocyanidins. Similar to Grape Seed Extract, see above. Improves muscle function and extends lifespan in drosophila model of Parkinson's disease through activation of mitophagy (PMID 30248358), has neuroprotective effect in Parkinson's Disease (PMID 31331731), protects skin from UVB-induced damage in mice (PMID 28697472), reduces amyloid-beta peptide aggregation, and thus helpful for treatment of Alzheimer's Disease, as it is taken up by brain endothelial cells (PMID 28208831) | Useful in treating and prevention of infections, improving metabolism, reducing obesity, improving hyperlipidemia, fatty liver, diabetes, anti-aging, wrinkles, hypercholesterolemia, hypertriglyceridemia, reducing high blood pressure/hypertension, improving glycemic control, decreases inflammation, useful in the treatment of any disease of inflammation, decreases body weight by altering neuropeptide Y signaling, useful in treating osteoporosis, preventing chemotherapy-induced lung and tissue damage, decreases atherosclerosis. Helpful in treating dementia, Parkinson's and Alzheimer's Disease. |
| Exosomes (Exosomes may be derived from stem cells, e.g., human placental mesenchymal stem cells) Range: 0.0001%-95% | Exosomes are mediators of cell-cell populations (PMID 30344611). By definition they are nanosized membrane vesicles released by fusion of an organelle of the endocytic pathway, the multivesicular body, with the plasma membrane. Once released from the cell, they facilitate communication between the cell of origin and other cells as they contain signaling molecules such as lipids, nucleic acids (PMID 28733901), ubiquitinated proteins (PMID 16203162), and micro RNAs (miRNA) specific to the cell of origin. For example communication between different cell exosomes derived from colorectal cancer cells showed distinct miRNA profiles compared to wild-type cells (PMID 26132860). Thus, | Useful in many diseases of many organs, as exosomes possess signals which may stimulate regeneration and healing in the target tissue or organ and/or, if necessary, induce apoptosis. They can be administered intravenously (IV), intramuscularly (IM) or applied topically to affected areas. With respect to this |

TABLE 1-continued

| Ingredient | Properties | Exemplary Utilities |
|---|---|---|
| | exosomes may transmit signals which may drive normal physiologic as well as pathologic processes (PMID 30344611). Ubiquitination appears to target proteins to exosomes (PMID 26246139, PMID 26574179), while the membranes of the exosomes allow them to deliver the signaling molecules past the cell membranes. Internal composition of exosomes is influenced by cellular conditions or treatments while exosome membrane composition is determined by the cell of origin (PMID 28733901). Exosome membranes are also rich in lipid rafts, which determine contents loaded into exosomes (PMID 28733901). Release of exosomes from a cell and incorporation of exosomes into a cell require overcoming multiple energy barriers, e.g., protein-lipid and protein-protein interactions occur to reduce the energy barriers and allow fusion (PMID 28733901). Oleic acid may enhance lipophilic penetration of skin cells (PMID 21871866, PMID 2367329), able to facilitate targeted drug delivery across the skin (PMID 2514720) most likely because it reduces energy barriers to membrane fusion (PMID 21871866) and creates a temporary disruption to the cell membrane allowing for drug permeability (PMID 2235880). As exosomes are released from the cell via "reverse endocytosis" they are by definition coated with a lipid membrane which allows them to fuse with other cells (PMID 28733901). The cells from which exosomes are derived determine their function, e.g., exosomes derived from cancer cells promote angiogenesis, modulate the immune system and remodel the surrounding parenchyma tissues; all which support tumor progression (PMID 27960084). For simplicity, "exosome(s)" will be taken to mean exosomes derived from stem cells, especially those from human placenta, as these possess properties which directly stimulate regeneration of existing adult tissues/organs. In injured tissues, stem cell-derived exosomes facilitate rapid healing and recovery. One of the current challenges of using stem cell-derived exosomes is that they tend to enter the systemic circulation; oftentimes away from intended target tissues if there is an area of greater injury within the body. The present invention provides a mechanism for slowly releasing the stem cell-derived exosomes in target tissues without affecting their inherent signaling capabilities. In certain embodiments, such a mechanism also enhances one or more function(s) of exosomes, as modulates their ability to penetrate the cell membrane lipid bilayer to deliver their contents to the nucleus and nucleolus (the "command center" of a cell). | application, the use of Liquid Skin or Vegan Liquid Skin as described herein may be used to enhance production of exosomes by decreasing energy barriers to exosome release, and/or to enhance delivery of exosome payload/internal components to target tissues. Biosilicates may be loaded with exosomes, and then with Liquid Skin or Vegan Liquid Skin to permit both extended release and enhanced delivery of exosomes into target cells, tissues and organs. This may permit localized, extended release of exosome contents into target tissues and limit their entry into the systemic circulation. |
| Ceramides, cholesterol, essential free fatty acids and non-essential free fatty acids in a 3:1:1:1 ratio adjusted for the final volume Range: adhere to the 3:1:1:1 ratio adjusted for final volume | Ceramides are a functional part of the human cell membrane, required for appropriate signals regulating cell differentiation, proliferation, and programmed cell death (important in both cancer and normal cell function). Ceramide levels are diminished in the epidermis of patients with eczema and psoriasis, thus restoring ceramides in this patient population will aid in restoring their skin to a normal state (PMID 16962101). Ceramides must exist in equimolar ratios with cholesterol and free fatty acids in order for proper epithelial cell membrane formation (PMID 8618046 and 16962101). In particular, a 3:1:1:1 ratio of cholesterol, ceramides, essential and nonessential free fatty acids accelerate human skin barrier recovery in aged skin (PMID 9308554) | Ceramides are useful in regeneration of skin and other cells, required for regulating cell differentiation, proliferation and apoptosis (programmed cell death; important in cancer and also normal cell function; important in cellular signaling. The correct ratio of cholesterol, ceramides, essential and non-essential free fatty acids are critical for restoring proper |

TABLE 1-continued

| Ingredient | Properties | Exemplary Utilities |
|---|---|---|
| | We will aim to restore the 9 major ceramides found in human stratum corneum (skin) (PMID 8357845): Cer 1 (EOS, or ester-linked fatty acids, omega-OH fatty acids and sphingosines) Cer 2 (NS, or non-OH fatty acids and sphingosines) Cer 3 (NP, non-OH fatty acids and phytosphingosines) Cer 4 (EOH) Cer 5 (AS, alpha-OH fatty acids and sphingosines) Cer 6 (AP, alpha-OH fatty acids and phytosphingosines) Cer 7 (AH,) Cer 8 (NH) Cer 9 (EOP) **Cer 1 (EOS, or ester-linked fatty acids, omega-OH fatty acids and sphingosines) is the main Cer fraction that is deficient in psoriasis (along with Cer 3 and Cer 6), with concurrent increase in ceramides containing sphingosine, while the total amount remained identical. Since one of the suggested pathways for phytosphingosine biosynthesis involves addition of water to the corresponding sphingosine double bond, we can speculate that the observed alteration is due to a deranged water bioavailability associated with psoriasis (PMID 8357845) Either way, adjusting the ceramide fractions in the Psoriasis Preparation would make sense. **of note, ALL ceramide fractions are decreased in eczema. Thus, increasing ceramides globally in the Eczema Preparation will be helpful. ***Ceramide signaling in stem cells and cancer cells (PMID 19050750) | skin barrier which has been lost in eczema, psoriasis, and irritant dermatitis |
| Phospholipids Range: (see list to right) Aim to recreate phospholipid composition of human skin with +/−5% if no range specified | Phospholipids form the majority of the cellular membrane and allow for a proper separation between the inside environment of the cell from the outside of the cell; they provide structure and stability to the membrane while maintaining and allowing for multiple signaling interactions to take place on both the internal and external surfaces of the cell membrane which are important for every disease process (e.g., inflammation, cancer, cell division, pain, to name a few). An aim is to recreate the phospholipid composition of the human skin, with +/−5% if no range is specified: Lecithin 68.3%-72.5% Phosphatidylcholine 36.6% Choline Plasmalogen 3.7% Phosphatidylethanolamine 3.4-10.2% Ethanolamine plasmalogen 7.6% Sphingomyelin 10.8%-18.7% Phosphatidylserine 2.1%-7.1% Lysophosphatidylcholine 7.5% Lysolecithin 4.9%-7.5% Phosphatidylinositol 3.1% Lysophosphatidylethanolamine 3.6% Phosphatidylinositol 4,5-bisphosphate 1.8% Phosphatidic acid 1.9% Phosphatidylinositol 4-phosphate 1.5% Cardiolipin 1.9% (PMID 1315902 and 6057496) | Major component of the cell membrane important in virtually every bodily function. |
| Hyaluronic Acids (mixed types) Range: 0.0001%-30% by weight | Important for hydration of the skin—holds >1000 times its weight in water, especially useful in the treatment of dry skin (xerosis), eczema and psoriasis. | Dry skin, eczema, psoriasis, burns, facilitating stem cell migration and proliferation in wound healing. |

TABLE 1-continued

| Ingredient | Properties | Exemplary Utilities |
| --- | --- | --- |
| Vegetable glycerin Range: 0.0001%-30% by weight | Important as a barrier and for hydration of the skin, used to seal in moisture. Useful as an emulsifier. | Dry skin, eczema, psoriasis, burns |
| Fusogens such as (polyethylene glycol, chitosan, dextran sulfate, n-nonyl bromide, calcium, sodium nitrate, and H-α-7) Range: 0.0001%-50% by weight | (PMID 30502271) Fusogens: Chemical Agents That Can Rapidly Restore Function After Nerve Injury. "Chitosan and Its Applications: A Review of Literature", | Potentially useful in peripheral neuropathy |
| Alpha-Lipoic Acid Range: 0.001%-10% by weight | Antioxidant which specifically protects lipids such as those found in the myelin sheath of neurons. Possesses anti-inflammatory properties by downregulating NFKB (NF kappa B) helpful in improving diabetic polyneuropathy, reducing oxidative stress, aging, cancer, improves microcirculation (PMID 160261130), improves blood flow to damaged nerves, nerve conduction velocity, and other measures of nerve function; is safe and efficacious in the treatment of diabetic neuropathy (PMID 25381809) | Peripheral neuropathy, anti-aging, diabetic peripheral neuropathy, anti-inflammatory, Raynaud's Phenomenon |
| Low Dose Naltrexone (LDN) Range: 0.5 mg-5 mg daily = Low Dose Naltrexone (LDN) <1 ug × <0.5 mg daily = Very Low Dose Naltrexone (VLDN) <1 ug daily = Ultra Low Dose Naltrexone | While not a natural compound, it was decided to include this as it is a safe drug with minimal side effects, and when used in a low dose of 1 to 5 mg daily has been found to reduce glial inflammatory response by modulating Toll-like receptor 4 signaling in addition to systemically upregulating endogenous opioid signaling by transient opioid-receptor blockade (PMID 30248938) Ranges: LDN: fibromyalgia, Crohn's disease, multiple sclerosis, complex-regional pain syndrome, Hailey-Hailey disease, and different types of cancer VLDN: boosting tolerability of opioid-weaning methadone taper ULDN: postoperative control of analgesia (reduces the need for total amount of opioids following surgery and ameliorating side-effects of opioid-related treatment) | Multiple clinical reports of LDN have demonstrated benefits in fibromyalgia, Chronic Fatigue Syndrome (CFS), Crohn's Disease (CD), Multiple Sclerosis (MS), complex-regional pain syndrome, Hailey-Hailey disease , and different types of cancer (PMID 30248938) |

In certain embodiments, a formulation comprises a mixture comprising, in % by volume, from about 3% to about 7% macadamia nut oil, from about 0.5% to about 1% coconut oil and from about 90% to about 99% emu oil. In some of these embodiments, the formulation comprises, in % by volume, about 5% macadamia nut oil, about 0.7% coconut oil and about 95% emu oil. In these embodiments, the mixture may improve cell membrane composition and function, and when admixed with other substances may impart and/or improve ability to incorporate into or penetrate past a cell membrane or a membrane of a cellular organelle.

In certain embodiments, a formulation comprises a mixture comprising, in % by volume, from about 0.03% to about 0.07% macadamia nut oil, from about 0.005% to about 0.009% coconut oil and from about 90% to about 99% Emu oil. In some of these embodiments, the formulation comprises, in % by volume, about 0.05% macadamia nut oil, about 0.007% coconut oil and about 99% emu oil. In these embodiments, the mixture may improve cell membrane composition and function, and when admixed with other substances may impart and/or improve the formulation's ability to incorporate or penetrate past a cell membrane or a membrane of a cellular organelle.

In certain embodiments, a formulation comprises a mixture comprising, in % by volume, from about 3% to about 7% macadamia nut oil, from about 0.5% to about 1% coconut oil and from about 90% to about 99% high oleic sunflower seed oil. In some of these embodiments, the formulation comprises, in % by volume, about 5% macadamia nut oil, about 0.7% coconut oil and about 95% high oleic sunflower seed oil. In these embodiments, the mixture may improve cell membrane composition and function, and when admixed with other substances may impart and/or improve the formulation's ability to incorporate into or penetrate past a cell membrane or a membrane of a cellular organelle.

In certain embodiments, a formulation comprises a mixture comprising, in % by volume, from about 0.03% to about 0.07% macadamia nut oil, from about 0.005% to about 0.009% coconut oil and from about 90% to about 99% high oleic sunflower seed oil. In some of these embodiments, the formulation comprises, in % by volume, about 0.05% macadamia nut oil, about 0.007% coconut oil and about 99% high oleic sunflower seed oil. In these embodiments, the mixture may improve cell membrane composition and function, and when admixed with other substances may impart and/or improve the formulation's ability to incorporate into or penetrate past a cell membrane or a membrane of a cellular organelle.

In certain embodiments, the invention is directed to a formulation comprising a mixture comprising, in % by volume, from about 70% to 85% olive oil, from about 2% to about 7% essential oil of clove, from about 2% to about 7% cinnamon essential oil, from about 2% to about 7% rosemary essential oil, from about 2% to about 7% eucalyptus essential oil, from about 2% to about 7% lemon essential oil, from about 0.05% to about 4% ravintsara essential oil, and from about 0.05% to about 3% cinnamon leaf essential oil. In these embodiments, the mixture may exhibit, e.g., antimicrobial, antiviral and antifungal properties as well as wound healing properties.

In certain embodiments, a formulation comprises a mixture comprising, in % by volume, from about 0.03% to about 0.07% macadamia nut oil, from about 0.005% to about 0.009% coconut oil, from about 2% to about 7% essential oil of clove, from about 2% to about 7% cinnamon essential oil, from about 2% to about 7% rosemary essential oil, from about 2% to about 7% eucalyptus essential oil, from about 2% to about 7% lemon essential oil, from about 0.05% to about 4% ravintsara essential oil, from about 0.05% to about 3% cinnamon leaf essential oil, and from about 50% to about 95% high oleic sunflower seed oil. In these embodiments, the mixture may exhibit, e.g., antimicrobial, antiviral and antifungal properties as well as wound healing properties.

In certain embodiments, a formulation comprises a mixture comprising, in % by volume, from about 0.03% to about 0.07% macadamia nut oil, from about 0.005% to about 0.009% coconut oil, from about 2% to about 7% essential oil of clove, from about 2% to about 7% cinnamon essential oil, from about 2% to about 7% rosemary essential oil, from about 2% to about 7% eucalyptus essential oil, from about 2% to about 7% lemon essential oil, from about 0.05% to about 7% ravintsara essential oil, from about 0.05% to about 7% cinnamon leaf essential oil, from about 0.05% to about 10% frankincense essential oil, from about 0.05% to about 10% myrrh essential oil, and from about 50% to about 95% high oleic sunflower seed oil. In these embodiments, the mixture may exhibit, e.g., antimicrobial, antiviral and antifungal properties as well as wound healing properties.

In certain embodiments, a formulation comprises a mixture comprising, in % by volume, from about 0.03% to about 0.07% macadamia nut oil, from about 0.005% to about 0.009% coconut oil, from about 2% to about 7% essential oil of clove, from about 2% to about 7% cinnamon essential oil, from about 2% to about 7% rosemary essential oil, from about 2% to about 7% eucalyptus essential oil, from about 2% to about 7% lemon essential oil, from about 0.05% to about 7% ravintsara essential oil, from about 0.05% to about 7% ravensara essential oil, from about 0.05% to about 7% laurel leaf, from about 0.05% to about 7% cinnamon leaf essential oil, from about 0.05% to about 7% rosalina essential oil, from about 0.05% to about 7% niaouli essential oil, from about 0.05% to about 7% frankincense essential oil, from about 0.05% to about 7% myrrh essential oil, from about 4% to about 30% peppermint essential oil, from about 0.5% to about 5% spearmint essential oil, from about 0.05% to about 3% wintergreen essential oil, and from about 40% to about 95% high oleic sunflower seed oil. In these embodiments, the mixture may exhibit, e.g., antimicrobial, antiviral and antifungal properties, may exhibit wound-healing properties, and may relieve a bronchospasm, a runny nose, cough, and/or discomfort and/or irritation from wearing a mask.

In certain embodiments, a formulation comprises a mixture comprising, in % by volume, from about 0.03% to about 0.07% macadamia nut oil, from about 0.005% to about 0.009% coconut oil, from about 2% to about 7% essential oil of clove, from about 2% to about 7% cinnamon essential oil, from about 2% to about 7% rosemary essential oil, from about 2% to about 7% eucalyptus essential oil, from about 2% to about 7% lemon essential oil, from about 0.05% to about 7% ravintsara essential oil, from about 0.05% to about 7% cinnamon leaf essential oil, from about 0.05% to about 7% frankincense essential oil, from about 0.05% to about 7% myrrh essential oil, from about 1% to about 17% white thyme essential oil, and from about 50% to about 95% high oleic sunflower seed oil. In these embodiments, the mixture may exhibit, e.g., antimicrobial, antiviral and antifungal properties.

In certain embodiments, a formulation comprises a mixture comprising, in % by volume, from about 0.2% to about 0.7% macadamia nut oil, from about 0.1% to about 0.5% coconut oil, from about 1% to about 7% essential oil of clove, from about 1% to about 7% cinnamon essential oil, from about 1% to about 7% rosemary essential oil, from about 1% to about 7% eucalyptus essential oil, from about 1% to about 7% lemon essential oil, from about 0.01% to about 7% ravintsara essential oil, from about 0.01% to about 7% cinnamon leaf essential oil, from about 0.05% to about 7% frankincense essential oil, from about 0.05% to about 7% myrrh essential oil, from about 1% to about 20% white thyme essential oil, and from about 50% to about 95% high oleic sunflower seed oil. In these embodiments, the mixture may exhibit, e.g., antimicrobial, antiviral and antifungal properties as well as wound healing properties.

In certain embodiments, a formulation comprises a mixture comprising, in % by volume, from about 0.1% to about 5% macadamia nut oil, from about 0.05% to about 2% coconut oil, from about 2% to about 7% essential oil of clove, from about 2% to about 7% cinnamon essential oil, from about 2% to about 7% rosemary essential oil, from about 2% to about 7% eucalyptus essential oil, from about 2% to about 7% lemon essential oil, from about 0.05% to about 7% ravintsara essential oil, from about 0.01% to about 7% cinnamon leaf essential oil, from about 0.01% to about 7% frankincense essential oil, from about 0.01% to about 7% myrrh essential oil, from about 1% to about 17% white thyme essential oil, from about 1% to about 17% xiang mao essential oil, from about 1% to about 17% cymbopogon citratus (lemongrass) essential oil, and from about 30% to about 95% high oleic sunflower seed oil. In these embodiments, the mixture may exhibit, e.g., antimicrobial, antiviral and antifungal properties as well as wound healing properties.

In certain embodiments, a formulation comprises a mixture comprising, in % by volume, from about 0.1% to about 5% macadamia nut oil, from about 0.01% to about 2% coconut oil, from about 2% to about 7% essential oil of clove, from about 2% to about 7% cinnamon essential oil, from about 2% to about 7% rosemary essential oil, from about 2% to about 7% eucalyptus essential oil, from about 2% to about 7% lemon essential oil, from about 0.05% to about 7% ravintsara essential oil, from about 0.01% to about 7% cinnamon leaf essential oil, from about 0.01% to about 7% frankincense essential oil, from about 0.01% to about 7% myrrh essential oil, from about 1% to about 17% white thyme essential oil, from about 1% to about 17% xiang mao essential oil, from about 1% to about 17% cymbopogon citratus (lemongrass) essential oil, from about 1% to about 17% coriander seed essential oil, and from about 30% to about 95% high oleic sunflower seed oil. In these embodiments, the mixture may exhibit, e.g., antimicrobial, antiviral and antifungal properties as well as wound healing properties.

In certain embodiments, the invention is directed to a formulation comprising a mixture comprising, in % by volume, from about 65% to 85% olive oil, from about 2% to about 7% essential oil of grapefruit, 2% to about 7% essential oil of clove, from about 2% to about 7% cinnamon essential oil, from about 2% to about 7% rosemary essential oil, from about 2% to about 7% eucalyptus essential oil, from about 2% to about 7% lemon essential oil, from about 0.05% to about 4% ravintsara essential oil, from about 0.01% to about 3% cinnamon leaf essential oil, and from about 0.01% to about 3% frankincense essential oil. In these embodiments, the mixture may exhibit, e.g., antimicrobial, antiviral and antifungal properties, wound-healing properties, and facilitate recovery from a microbial, viral or a fungal infection.

In certain embodiments, the invention is directed to a formulation comprising a mixture comprising, in % by volume, from about 0.2% to about 0.7% macadamia nut oil, from about 0.1% to about 0.5% coconut oil, from about 50% to 95% high oleic acid sunflower seed oil, from about 1% to about 12% essential oil of grapefruit, 1% to about 7% essential oil of clove, from about 1% to about 7% cinnamon essential oil, from about 1% to about 7% rosemary essential oil, from about 1% to about 12% eucalyptus essential oil, from about 1% to about 12% lemon essential oil, from about 1% to about 12% frankincense essential oil, from about 1% to about 12% myrrh essential oil, and from about 1% to about 12% xiang mao essential oil, from about 1% to about 12% essential oil of rosalina, 1% to about 12% essential oil of palmarosa, from about 1% to about 12% essential oil of ravintsara, from about 1% to about 12% essential oil of ravensara, from about 1% to about 12% essential oil of laurel leaf, from about 1% to about 12% essential oil of niaouli, from about 1% to about 12% cinnamon leaf essential oil, from about 1% to about 12% white thyme essential oil. In these embodiments, the mixture may exhibit, e.g., antimicrobial, antiviral and antifungal properties, wound-healing properties, and facilitate recovery from a microbial, viral or a fungal infection.

In certain embodiments, the invention is directed to a formulation comprising a mixture comprising, in % by volume, from about 20% to 50% olive oil, from about 40% to 55% high oleic acid sunflower seed oil, from about 0.001% to about 3% coconut oil, from about 0.01% to about 5% essential oil of macadamia nut oil, from about 1% to about 7% clove essential oil, from about 1% to about 7% cinnamon essential oil, from about 1% to about 7% rosemary essential oil, from about 1% to about 7% eucalyptus essential oil, from about 1% to about 7% lemon essential oil, from about 0.01% to about 3% ravintsara essential oil, and from about 0.001% to about 2% cinnamon leaf essential oil, from about 0.01% to about 7% essential oil of frankincense, 0.01% to about 7% essential oil of white thyme, from about 0.01% to about 7% rosalina essential oil, from about 0.01% to about 7% palmarosa essential oil, from about 0.01% to about 7% niaouli essential oil, from about 0.01% to about 7% laurel leaf essential oil, from about 0.01% to about 7% litsea essential oil. In these embodiments, the mixture may exhibit, e.g., antimicrobial, antiviral, antifungal properties, anti-trypanosomal properties, wound-healing properties, and facilitate recovery from a microbial, viral, a fungal or trypanosomal infection.

In certain embodiments, the invention is directed to a formulation comprising a mixture comprising, in % by volume, from about 20% to 50% olive oil, from about 40% to 55% high oleic acid sunflower seed oil, from about 0.001% to about 3% coconut oil, from about 0.01% to about 5% essential oil of macadamia nut oil, from about 1% to about 7% clove essential oil, from about 1% to about 7% cinnamon essential oil, from about 1% to about 7% rosemary essential oil, from about 1% to about 7% eucalyptus essential oil, from about 1% to about 7% lemon essential oil, from about 0.01% to about 7% ravintsara essential oil, and from about 0.001% to about 7% cinnamon leaf essential oil, from about 0.01% to about 7% essential oil of frankincense, from about 0.01% to about 7% essential oil of myrrh, 0.01% to about 7% essential oil of white thyme, from about 0.01% to about 7% rosalina essential oil, from about 0.01% to about 7% palmarosa essential oil, from about 0.01% to about 7% niaouli essential oil, from about 0.01% to about 7% laurel leaf essential oil, from about 0.01% to about 7% litsea essential oil, from about 0.01% to about 7% essential oil of xiang mao, from about 0.01% to about 7% essential oil of cymbopogon citratus, from about 0.01% to about 7% essential oil of coriander seed. In these embodiments, the mixture may exhibit, e.g., antimicrobial, antiviral, antifungal properties, antiparasitic and wound-healing properties, and facilitate recovery from a microbial, viral, a fungal or a parasitic infection.

In certain embodiments, the invention is directed to a formulation comprising a mixture comprising, in % by volume, from about 40% to 65% high oleic acid sunflower seed oil, from about 0.001% to about 3% coconut oil, from about 0.01% to about 7% of macadamia nut oil, from about 1% to about 10% clove oil, from about 1% to about 10% cinnamon essential oil, from about 1% to about 10% rosemary essential oil, from about 1% to about 10% eucalyptus essential oil, from about 1% to about 10% lemon essential oil, from about 1% to about 10% ravintsara essential oil, and from about 10% to about 10% cinnamon leaf essential oil, from about 1% to about 10% essential oil of frankincense, 1% to about 10% essential oil of myrrh, from about 1% to about 10% white thyme essential oil, from about 0.01% to about 10% rosalina essential oil, from about 1% to about 10% xiang mao essential oil, from about 1% to about 10% cymbopogon martinii (palmarosa) essential oil, from about 1% to about 10% cymbopogon martinii var sophia (gingergrass) essential oil, from about 1% to about 10% cymbopogon citratus (lemongrass) essential oil, from about 1% to about 10% coriander seed essential oil, from about 1% to about 10% niaouli essential oil, from about 1% to about 10% laurel leaf essential oil, from about 1% to about 10% litsea essential oil, from about 1% to about 10% neroli essential oil. In these embodiments, the mixture may exhibit, e.g., antimicrobial, antiviral, antifungal properties, antiparasitic and wound-healing properties, and facilitate recovery from a microbial, viral, a fungal or a parasitic infection.

In certain embodiments, the invention is directed to a formulation comprising a mixture comprising, in % by volume, from about 2% to about 6% German chamomile essential oil, from about 94% to about 98% emu oil. In these embodiments, the mixture may alleviate pain and inflammation.

In certain embodiments, the invention is directed to a formulation comprising a mixture comprising, in % by volume, from about 2% to about 5% German chamomile essential oil, from about 0.01% to about 1% peppermint essential oil, from about 0.01% to about 1% Bridal Garden Jerusalem anointing oil (by www.thenewjerusalem.co), and from about 80%-90% emu oil. In these embodiments, the mixture may alleviate pain and inflammation.

In certain embodiments, the invention is directed to a formulation comprising a mixture comprising, in % by volume, from about 1% to about 25% biosilicates loaded with minerals, amino acids, vitamins and other ingredients (e.g., bioactive compounds) for long-acting relief of pain and anxiety, delivery of substances required for tissue repair, from about 0.01% to about 2% German chamomile essential oil, about 0.01% to about 3% Moroccan chamomile essential oil, from about 0.01% to about 2% Roman chamomile essential oil, from about 0.01% to about 2% jasmine essential oil, from about 0.01% to about 2% lemongrass essential oil, from about 70% to about 99% emu oil. In these embodiments, the mixture may alleviate pain and inflammation.

In certain embodiments, the invention is directed to a formulation comprising a mixture comprising, in % by volume, from about 15% to about 25% biosilicates loaded with minerals, amino acids, vitamins and other bioactive compounds for long-acting relief of pain and anxiety, delivery of substances required for tissue repair, about 10% to about 15% Moroccan chamomile essential oil, from about 2% to about 15% Roman chamomile essential oil, from about 6% to about 9% jasmine essential oil, from about 6% to about 9% vanilla planifolia essential oil, from about 50% to about 99% emu oil. In these embodiments, the mixture may alleviate pain and inflammation.

In certain embodiments, the invention is directed to a formulation comprising a mixture comprising, in % by volume, from about 1% to about 25% biosilicates loaded with minerals, amino acids, vitamins and other bioactive compounds for long-acting relief of pain and anxiety, delivery of substances required for tissue repair, from about 0.01% to about 30% German chamomile essential oil, about 0.01% to about 30% Moroccan chamomile essential oil, from about 0.01% to about 30% Roman chamomile essential oil, from about 0.01% to about 2% jasmine essential oil, from about 0.01% to about 2% lemongrass essential oil, from about 2%-4% coconut oil, from about 25-29% macadamia nut oil, from about 20% to about 70% emu oil. In these embodiments, the mixture may alleviate pain and inflammation.

In certain embodiments, the invention is directed to a formulation comprising a mixture comprising, in % by volume, from about 1% to about 25% biosilicates loaded with minerals, amino acids, vitamins and other bioactive compounds for long-acting relief of pain and anxiety, delivery of substances required for tissue repair, from about 0.01% to about 30% German chamomile essential oil, about 0.01% to about 30% Moroccan chamomile essential oil, from about 0.01% to about 30% Roman chamomile essential oil, about 0.01% to about 3% frankincense essential oil, from about 0.01% to about 3% myrrh essential oil, from about 2% to about 5% of macadamia nut oil, from about 0.01% to about 2% of coconut oil, from about 1% to about 4% jasmine essential oil, from about 1% to about 4% lemongrass essential oil, from about 25% to about 85% emu oil. In these embodiments, the mixture may exhibit alleviate pain and inflammation.

In certain embodiments, the invention is directed to a formulation comprising a mixture comprising, in % by volume, from about 5% to about 18% biosilicates loaded with minerals, amino acids, vitamins and other bioactive compounds for long-acting relief of pain and anxiety, delivery of substances required for tissue repair, from about 0.01% to about 3% German chamomile essential oil, about 0.01% to about 3% Moroccan chamomile essential oil, from about 0.01% to about 3% Roman chamomile, from about 1% to about 8% frankincense oil, from about 1% to about 8% myrrh oil, from about 2% to about 27% of macadamia nut oil, from about 0.01% to about 10% of coconut oil, from about 0.01% to about 3% jasmine essential oil, from about 0.01% to about 3% lemongrass essential oil, from about 35% to about 85% emu oil. In these embodiments, the mixture may alleviate pain and inflammation.

In certain embodiments, the invention is directed to a formulation comprising a mixture comprising, in % by volume, from about 2% to about 25% biosilicates loaded with minerals, amino acids, vitamins and other bioactive compounds for long-acting relief of pain and anxiety, delivery of substances required for tissue repair, from about 0.01% to about 30% German chamomile essential oil, about 0.01% to about 30% Moroccan chamomile essential oil, from about 0.01% to about 30% Roman chamomile essential oil, from about 0.01% to about 10% frankincense essential oil, from about 0.01% to about 10% myrrh essential oil, from about 0.01% to about 2% of jasmine essential oil, from about 0.01% to about 2% of lemongrass essential oil, from about 0.01% to about 3% sweet orange essential oil, from about 0.01% to about 3% bitter orange essential oil, from about 0.01% to about 3% rosemary essential oil, from about 0.01% to about 3% galangal essential oil, from about 0.01% to about 3% xiang mao essential oil, from about 0.01% to about 3% palmarosa essential oil, from about 0.01% to about 3% neroli essential oil, from about 0.01% to about 5% licorice extract, from about 2% to about 9% lecithin, from about 0.01% to about 2% coconut oil, from about 0.01% to about 5% macadamia nut oil, from about 25% to about 90% emu oil. In these embodiments, the mixture may alleviate pain and inflammation.

In certain embodiments, the invention is directed to a formulation comprising a mixture comprising, in % by volume, from about 2% to about 25% biosilicates loaded with minerals, amino acids, vitamins and other bioactive compounds for long-acting delivery of substances required for tissue repair, from about 0.01% to about 3% gallic acid, from about 0.01% to about 30% German chamomile essential oil, about 0.01% to about 30% Moroccan chamomile essential oil, from about 0.01% to about 30% Roman chamomile essential oil, from about 0.01% to about 10% frankincense essential oil, from about 0.01% to about 10% myrrh essential oil, from about 0.01% to about 2% of jasmine essential oil, from about 0.01% to about 2% of lemongrass essential oil, from about 0.01% to about 2% of cinnamon essential oil, from about 0.01% to about 2% of cinnamon leaf essential oil, from about 0.01% to about 2% of rosemary essential oil, from about 0.01% to about 3% sweet orange essential oil, from about 0.01% to about 3% bitter orange essential oil, from about 0.01% to about 3% rosemary essential oil, from about 0.01% to about 2% of ravintsara essential oil, from about 0.01% to about 3% galangal essential oil, from about 0.01% to about 3% xiang mao essential oil, from about 0.01% to about 2% of gingergrass essential oil, from about 0.01% to about 3% palmarosa essential oil, from about 0.01% to about 2% of geranium essential oil, from about 0.01% to about 3% neroli essential oil, from about 0.01% to about 5% licorice extract, from about 0.01% to about 2% of ginger essential oil, from about 2% to about 9% lecithin, from about 0.01% to about 2% of saturated dead sea salt solution, from about 0.01% to about 2% coconut oil, from about 0.01% to about 5% macadamia nut oil, from about 35% to about 90% emu oil. In these embodiments, the mixture may alleviate pain and inflammation.

In certain embodiments, the invention is directed to a formulation comprising a mixture comprising, in % by volume, from about 2% to about 25% biosilicates loaded with minerals, amino acids, vitamins and other bioactive compounds for long-acting delivery of substances required for tissue repair, from about 0.01% to about 3% gallic acid, from about 0.01% to about 30% German chamomile essential oil, about 0.01% to about 30% Moroccan chamomile essential oil, from about 0.01% to about 30% Roman chamomile essential oil, from about 0.01% to about 10% frankincense essential oil, from about 0.01% to about 10% myrrh essential oil, from about 0.01% to about 2% of jasmine essential oil, from about 0.01% to about 2% of lemongrass essential oil, from about 0.01% to about 2% of cinnamon essential oil, from about 0.01% to about 2% of cinnamon leaf essential oil, from about 0.01% to about 2% of rosemary essential oil, from about 0.01% to about 3% sweet orange essential oil, from about 0.01% to about 3% bitter orange essential oil, from about 0.01% to about 3% rosemary essential oil, from about 0.01% to about 2% of ravintsara essential oil, from about 0.01% to about 3% galangal essential oil, from about 0.01% to about 3% xiang mao essential oil, from about 0.01% to about 2% of gingergrass essential oil, from about 0.01% to about 3% palmarosa essential oil, from about 0.01% to about 2% of geranium essential oil, from about 0.01% to about 3% neroli essential oil, from about 0.01% to about 5% licorice extract, from about 0.01% to about 2% of ginger essential oil, from about 0.01% to about 10% of peppermint essential oil, from about 0.01% to about 7% of spearmint essential oil, from about 0.01% to about 1% of wintergreen essential oil, from about 2% to about 9% lecithin, from about 0.01% to about 2% of saturated dead sea salt solution, from about 0.01% to about 2% coconut oil, from about 0.01% to about 5% macadamia nut oil, from about 35% to about 90% emu oil. In these embodiments, the mixture may alleviate pain and inflammation.

In certain embodiments, the invention is directed to a formulation comprising a mixture comprising, in % by volume, from about 2% to about 25% biosilicates loaded with minerals, amino acids, vitamins and other bioactive compounds for long-acting delivery of substances required for tissue repair, from about 0.01% to about 3% gallic acid, from about 0.01% to about 30% German chamomile essential oil, about 0.01% to about 30% Moroccan chamomile essential oil, from about 0.01% to about 30% Roman chamomile essential oil, from about 0.01% to about 10% frankincense essential oil, from about 0.01% to about 10% myrrh essential oil, from about 0.01% to about 2% of jasmine essential oil, from about 0.01% to about 2% of lemongrass essential oil, from about 0.01% to about 2% of cinnamon essential oil, from about 0.01% to about 2% of cinnamon leaf essential oil, from about 0.01% to about 2% of rosemary essential oil, from about 0.01% to about 3% sweet orange essential oil, from about 0.01% to about 3% bitter orange essential oil, from about 0.01% to about 3% rosemary essential oil, from about 0.01% to about 2% of ravintsara essential oil, from about 0.01% to about 3% galangal essential oil, from about 0.01% to about 3% xiang mao essential oil, from about 0.01% to about 2% of gingergrass essential oil, from about 0.01% to about 3% palmarosa essential oil, from about 0.01% to about 2% of geranium essential oil, from about 0.01% to about 3% neroli essential oil, from about 0.01% to about 5% licorice extract, from about 0.01% to about 2% of ginger essential oil, from about 0.01% to about 10% of turmeric essential oil, from about 0.01% to about 10% of blackseed essential oil, from about 2% to about 9% lecithin, from about 0.01% to about 2% of saturated dead sea salt solution, from about 0.01% to about 2% coconut oil, from about 0.01% to about 5% macadamia nut oil, from about 35% to about 90% emu oil. In these embodiments, the mixture may alleviate pain and inflammation.

In certain embodiments, the invention is directed to a formulation comprising a mixture comprising, in % by volume, from about 2% to about 10% biosilicates loaded with at least one ingredient selected from the group comprising minerals, amino acids, vitamins and other bioactive compounds for long-acting delivery of substances required for tissue repair. For example, the formulation may comprise from about 0.01% to about 7% ubiquinol (final concentration of about 30-50 mg/ml), from about 0.01% to about 4% vitamin A (final concentration of about 300-350 mcg/ml), from about 0.01% to about 10% vitamin D (final concentration of about 690-730 IU/ml), from about 0.01% to about 10% vitamin E (final concentration of about 5-15 mg/ml of d-alpha tocopherol, final concentration of mixed tocopherols, including d-beta, d-gamma, and d-delta tocopherol is from about 0.001 to 1 mg/ml), from about 0.01% to about 10% vitamin K2 MK7 (final concentration of about 10-40 mcg/ml), about 0.01% to about 25% vitamin C, from about 0.01% to about 4% alpha arbutin, from about 0.01% to about 3% gallic acid, from about 0.01% to about 10% frankincense essential oil, from about 0.01% to about 10% myrrh essential oil, from about 0.01% to about 5% kojic acid, from about 0.01% to about 10% licorice root extract, from about 0.01% to about 12% of niacinamide, from about 0.01% to about 6% of kaempferia galanga essential oil, from about 0.01% to about 5% niaouli essential oil, from about 0.01% to about 3% glutathione, from about 0.01% to about 12% hyaluronic acid, from about 0.01% to about 5% clove essential oil, from about 0.01% to about 5% eucalyptus essential oil, from about 0.01% to about 5% lemon essential oil, from about 0.01% to about 5% rosemary essential oil, from about 0.01% to about 5% cinnamon essential oil, from about 0.01% to about 5% cinnamon leaf essential oil, from about 0.01% to about 5% ravintsara essential oil, from about 0.01% to about 3% palmarosa essential oil, from about 0.01% to about 5% macadamia nut oil, from about 0.01% to about 3% coconut oil, from about 2% to about 9% lecithin, from about 1% to about 9% vegetable glycerin, from about 35% to about 90% emu oil. In these embodiments, the mixture may have skin whitening and age spot fading properties.

In certain embodiments, the invention is directed to a formulation comprising a mixture comprising, in % by volume, from about 2% to about 10% biosilicates loaded with at least one ingredient selected from the group comprising minerals, amino acids, vitamins and other bioactive compounds, e.g., for long-acting delivery of substances required for tissue repair. The formulation may, e.g., comprise from about 0.01% to about 7% ubiquinol (final concentration of about 30-50 mg/ml), from about 0.01% to about 4% vitamin A (final concentration of about 300-350 mcg/ml), from about 0.01% to about 10% vitamin D (final concentration of about 690-730 IU/ml), from about 0.01% to about 10% vitamin E (final concentration of about 5-15 mg/ml of d-alpha tocopherol, final concentration of mixed tocopherols, including d-beta, d-gamma, and d-delta tocopherol is from about 0.001 to 1 mg/ml), from about 0.01% to about 10% vitamin K2 MK7 (final concentration of about 10-40 mcg/ml), about 0.01% to about 25% vitamin C, from about 0.01% to about 3% gallic acid, from about 0.01% to about 3% saturated dead sea salt solution, from about 0.01% to about 3% glutathione, from about 0.01% to about 12% hyaluronic acid, from about 0.01% to about 10% licorice root extract, from about 0.05% to about 12% of niacinamide, from about 0.001% to about 1% of ginger essential oil, from about 0.01% to about 10% frankincense essential oil, from about 0.01% to about 10% myrrh essential oil, from about 0.01% to about 6% essential oil of kaempferia galanga, from about 0.01% to about 3% palmarosa essential oil, from about 0.01% to about 5% clove essential oil, from about 0.01% to about 5% eucalyptus essential oil, from about 0.01% to about 5% lemon essential oil, from about 0.01% to about 5% rosemary essential oil, from about 0.01% to about 5% cinnamon essential oil, from about 0.01% to about 5% cinnamon leaf essential oil, from about 0.01% to about 5% ravintsara essential oil, from about 0.01% to about 3% bitter orange essential oil, from about 0.01% to about 3% sweet orange essential oil, from about 0.01% to about 5% niaouli essential oil, from about 0.01% to about 3% gingergrass essential oil, from about 0.01% to about 3% turmeric essential oil, from about 0.01% to about 5% macadamia nut oil, from about 0.01% to about 5% coconut oil, from about 0.01% to about 3% lauric acid (in addition to the lauric acid in the coconut oil), from about 2% to about 9% lecithin, from about 1% to about 9% vegetable glycerin, from about 35% to about 90% emu oil. In these embodiments, the mixture may have anti-acne properties. It may also improve skin texture.

In certain embodiments, the invention is directed to a formulation comprising a mixture comprising, in % by volume, from about 2% to about 10% biosilicates loaded with at least one ingredient selected from the group comprising minerals, amino acids, vitamins and other bioactive compounds, e.g., for long-acting delivery of substances required for tissue repair. For example, the formulation may comprise from about 0.01% to about 7% ubiquinol (final concentration of about 30-50 mg/ml), from about 0.01% to about 3% retinol, from about 0.01% to about 4% vitamin A (final concentration of about 300-350 mcg/ml), from about 0.01% to about 10% vitamin D (final concentration of about 690-730 IU/ml), from about 0.01% to about 10% vitamin E (final concentration of about 5-15 mg/ml of d-alpha tocopherol, final concentration of mixed tocopherols, including d-beta, d-gamma, and d-delta tocopherol is from about 0.001 to 1 mg/ml), from about 0.01% to about 10% vitamin K2 MK7 (final concentration of about 10-40 mcg/ml), about 0.01% to about 25% vitamin C, from about 0.01% to about 3% gallic acid, from about 0.01% to about 3% saturated dead sea salt solution, from about 0.01% to about 3% glutathione, from about 0.01% to about 12% hyaluronic acid, from about 0.01% to about 10% licorice root extract, from about 0.05% to about 12% of niacinamide, from about 0.001% to about 1% of ginger essential oil, from about 0.01% to about 15% frankincense essential oil, from about 0.01% to about 15% myrrh essential oil, from about 0.01% to about 6% essential oil of kaempferia galanga, from about 0.01% to about 3% palmarosa essential oil, from about 0.01% to about 3% rosemary essential oil, from about 0.01% to about 3% bitter orange essential oil, from about 0.01% to about 3% sweet orange essential oil, from about 0.01% to about 5% clove essential oil, from about 0.01% to about 5% eucalyptus essential oil, from about 0.01% to about 5% lemon essential oil, from about 0.01% to about 5% rosemary essential oil, from about 0.01% to about 5% cinnamon essential oil, from about 0.01% to about 5% cinnamon leaf essential oil, from about 0.01% to about 5% ravintsara essential oil, from about 0.01% to about 5% niaouli essential oil, from about 0.01% to about 3% gingergrass essential oil, from about 0.01% to about 3% turmeric essential oil, from about 0.01% to about 5% macadamia nut oil, from about 0.01% to about 5% coconut oil, from about 0.01% to about 3% lauric acid (in addition to the lauric acid in the coconut oil), from about 2% to about 9% lecithin, from about 1% to about 9% vegetable glycerin, from about 35% to about 90% Emu oil. In these embodiments, the mixture may have anti-acne properties. It may also improve skin texture and improve appearance of scars and keloids.

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. For example, the formulation may comprise from about 0.01% to about 7% ubiquinol (final concentration of about 1-1000 mg/ml), from about 0.01% to about 4% vitamin A (final concentration of about 300-350 mcg/ml), from about 0.01% to about 10% vitamin D (final concentration of about 690-730 IU/ml), from about 0.01% to about 10% vitamin E (final concentration of about 5-15 mg/ml of d-alpha tocopherol, final concentration of mixed tocopherols, including d-beta, d-gamma, and d-delta tocopherol is from about 0.001 to 1 mg/ml), from about 0.01% to about 10% vitamin K2 MK7 (final concentration of about 10-40 mcg/ml), from about 0.001% to about 10% saturated dead sea salt solution, from about 0.01% to about 12% hyaluronic acid, from about 0.01% to about 12% vegetable glycerin, from about 0.01% to about 3% German chamomile essential oil, from about 0.01% to about 5% Moroccan chamomile essential oil, from about 0.01% to about 3% Roman chamomile essential oil, from about 0.01% to about 3% jasmine essential oil, from about 0.01% to about 3% lemongrass essential oil, from about 0.01% to about 5% lemon essential oil, from about 0.01% to about 5% eucalyptus essential oil, from about 0.01% to about 5% rosemary essential oil, from about 0.01% to about 5% clove essential oil, from about 0.01% to about 5% cinnamon essential oil, from about 0.01% to about 5% cinnamon leaf essential oil, from about 0.01% to about 5% ravintsara essential oil, from about 0.01% to about 30% macadamia nut oil, from about 0.01% to about 5% coconut oil, from about 15% to about 90% emu oil. In these embodiments, the mixture may be particularly useful for treatment of eczema, psoriasis, unspecified rashes and wounds of the skin.

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. For example, the formulation may comprise from about 0.01% to about 7% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), from about 0.001% to about 10% saturated dead sea salt solution, from about 0.01% to about 20% hyaluronic acid, from about 0.01% to about 20% vegetable glycerin, from about 0.01% to about 6% German chamomile essential oil, from about 0.01% to about 10% Moroccan chamomile essential oil, from about 0.01% to about 6% Roman chamomile essential oil, from about 0.01% to about 3% jasmine essential oil, from about 0.01% to about 3% lemongrass essential oil, from about 0.01% to about 5% lemon essential oil, from about 0.01% to about 5% eucalyptus essential oil, from about 0.01% to about 5% rosemary essential oil, from about 0.01% to about 5% clove essential oil, from about 0.01% to about 5% cinnamon essential oil, from about 0.01% to about 5% cinnamon leaf essential oil, from about 0.01% to about 5% ravintsara essential oil, from about 0.01% to about 20% frankincense essential oil, from about 0.01% to about 20% myrrh essential oil, from about 0.01% to about 20% lecithin, from about 0.001% to about 5% gallic acid, from about 0.001% to about 5% turmeric essential oil, from about 0.01% to about 30% macadamia nut oil, from about 0.01% to about 5% coconut oil, from about 15% to about 90% emu oil. In these embodiments, the mixture may be particularly useful for treatment of eczema, psoriasis, unspecified rashes and wounds of the skin.

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. The formulation may comprise, e.g., from about 0.01% to about 7% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), from about 0.001% to about 10% saturated dead sea salt solution, from about 0.01% to about 20% hyaluronic acid, from about 0.01% to about 20% vegetable glycerin, from about 0.01% to about 6% German chamomile essential oil, from about 0.01% to about 20% Moroccan chamomile essential oil, from about 0.01% to about 6% Roman chamomile essential oil, from about 0.01% to about 3% jasmine essential oil, from about 0.01% to about 3% lemongrass essential oil, from about 0.01% to about 5% lemon essential oil, from about 0.01% to about 5% eucalyptus essential oil, from about 0.01% to about 5% rosemary essential oil, from about 0.01% to about 5% clove essential oil, from about 0.01% to about 5% cinnamon essential oil, from about 0.01% to about 5% cinnamon leaf essential oil, from about 0.01% to about 5% ravintsara essential oil, from about 0.01% to about 20% frankincense essential oil, from about 0.01% to about 20% myrrh essential oil, from about 0.01% to about 20% lecithin, from about 0.001% to about 5% gallic acid, from about 0.001% to about 5% turmeric essential oil, from about 0.001% to about 5% zanthoxylum coreanum nakai essential oil (Wang-Cho-Pi, or Korean lime tree), from about 0.01% to about 30% macadamia nut oil, from about 0.01% to about 5% coconut oil, from about 15% to about 90% emu oil. In these embodiments, the mixture may be particularly useful for treatment of eczema, psoriasis, unspecified rashes and wounds of the skin; and may reduce biological causes of itching.

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. The formulation, may, e.g., comprise from about 0.01% to about 7% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), about 0.01% to about 25% vitamin C, from about 0.01% to about 4% alpha arbutin, from about 0.01% to about 5% kojic acid, from about 0.01% to about 10% licorice root extract, from about 0.01% to about 10% ginger root extract, from about 0.01% to about 10% ginger root essential oil, from about 0.01% to about 12% of niacinamide, from about 0.01% to about 6% of essential oil of kaempferia galanga, from about 0.01% to about 5% niaouli essential oil, from about 0.01% to about 5% palmarosa essential oil, from about 0.01% to about 3% glutathione, from about 0.001% to about 10% saturated dead sea salt solution, from about 0.01% to about 20% hyaluronic acid, from about 0.01% to about 20% vegetable glycerin, from about 0.01% to about 6% German chamomile essential oil, from about 0.01% to about 10% Moroccan chamomile essential oil, from about 0.01% to about 6% Roman chamomile essential oil, from about 0.01% to about 3% jasmine essential oil, from about 0.01% to about 3% lemongrass essential oil, from about 0.01% to about 5% lemon essential oil, from about 0.01% to about 5% eucalyptus essential oil, from about 0.01% to about 5% rosemary essential oil, from about 0.01% to about 5% clove essential oil, from about 0.01% to about 5% cinnamon essential oil, from about 0.01% to about 5% cinnamon leaf essential oil, from about 0.01% to about 5% ravintsara essential oil, from about 0.01% to about 20% frankincense essential oil, from about 0.01% to about 20% myrrh essential oil, from about 0.01% to about 20% lecithin, from about 0.001% to about 5% gallic acid, from about 0.001% to about 5% turmeric essential oil, from about 5%-20% of sea kelp bioferment (extract of fermented seaweed), from about 0.01% to about 30% macadamia nut oil, from about 0.01% to about 5% coconut oil, from about 15% to about 90% emu oil. In these embodiments, the mixture may be particularly useful for treatment of eczema, psoriasis and unspecified rashes and skin wounds. The mixture is formulated to result in anti-aging, skin-brightening, and cosmetic moisturizing properties.

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. The formulation may comprise, e.g., from about 0.01% to about 1% retinol, from about 0.01% to about 7% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), about 0.01% to about 25% vitamin C, from about 0.01% to about 4% alpha arbutin, from about 0.01% to about 5% kojic acid, from about 0.01% to about 10% licorice root extract, from about 0.01% to about 10% ginger root extract, from about 0.01% to about 10% ginger root essential oil, from about 0.01% to about 12% of niacinamide, from about 0.01% to about 6% of essential oil of kaempferia galanga, from about 0.01% to about 5% niaouli essential oil, from about 0.01% to about 5% palmarosa essential oil, from about 0.01% to about 3% glutathione, from about 0.001% to about 10% saturated dead sea salt solution, from about 0.01% to about 20% hyaluronic acid, from about 0.01% to about 20% vegetable glycerin, from about 0.01% to about 6% German chamomile essential oil, from about 0.01% to about 10% Moroccan chamomile essential oil, from about 0.01% to about 6% Roman chamomile essential oil, from about 0.01% to about 3% jasmine essential oil, from about 0.01% to about 3% lemongrass essential oil, from about 0.01% to about 5% lemon essential oil, from about 0.01% to about 5% eucalyptus essential oil, from about 0.01% to about 5% rosemary essential oil, from about 0.01% to about 5% clove essential oil, from about 0.01% to about 5% cinnamon essential oil, from about 0.01% to about 5% cinnamon leaf essential oil, from about 0.01% to about 5% ravintsara essential oil, from about 0.01% to about 20% frankincense essential oil, from about 0.01% to about 20% myrrh essential oil, from about 0.01% to about 20% lecithin, from about 0.001% to about 5% gallic acid, from about 0.001% to about 5% turmeric essential oil, from about 5%-20% of sea kelp bioferment (extract of fermented seaweed), from about 0.01% to about 30% macadamia nut oil, from about 0.01% to about 5% coconut oil, from about 15% to about 90% emu oil. In these embodiments, the mixture may be particularly useful for treatment of eczema, psoriasis and unspecified rashes and wounds of the skin. The mixture is formulated to result in anti-aging, skin-brightening, and cosmetic moisturizing properties.

In certain embodiments, the invention is directed to a formulation comprising a mixture comprising, in % by volume, from about 2% to about 70% biosilicates loaded with at least one ingredient selected from the group comprising minerals, amino acids, vitamins and other bioactive compounds, e.g., for long-acting delivery of substances required for tissue repair. For example, the formulation may comprise from about 0.01% to about 1% retinol, from about 0.01% to about 7% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), about 0.01% to about 25% vitamin C, from about 0.01% to about 4% alpha arbutin, from about 0.01% to about 5% kojic acid, from about 0.01% to about 10% licorice root extract, from about 0.01% to about 10% ginger root extract, from about 0.01% to about 10% ginger root essential oil, from about 0.01% to about 12% of niacinamide, from about 0.01% to about 6% of essential oil of kaempferia galanga, from about 0.01% to about 5% niaouli essential oil, from about 0.01% to about 5% palmarosa essential oil, from about 0.01% to about 3% glutathione, from about 0.001% to about 10% saturated dead sea salt solution, from about 0.01% to about 20% hyaluronic acid, from about 0.01% to about 20% vegetable glycerin, from about 0.01% to about 6% German chamomile essential oil, from about 0.01% to about 10% Moroccan chamomile essential oil, from about 0.01% to about 6% Roman chamomile essential oil, from about 0.01% to about 3% jasmine essential oil, from about 0.01% to about 3% lemongrass essential oil, from about 0.01% to about 5% lemon essential oil, from about 0.01% to about 5% eucalyptus essential oil, from about 0.01% to about 5% rosemary essential oil, from about 0.01% to about 5% clove essential oil, from about 0.01% to about 5% cinnamon essential oil, from about 0.01% to about 5% cinnamon leaf essential oil, from about 0.01% to about 5% ravintsara essential oil, from about 0.01% to about 20% frankincense essential oil, from about 0.01% to about 20% myrrh essential oil, from about 0.01% to about 20% lecithin, from about 0.001% to about 5% gallic acid, from about 0.001% to about 5% turmeric essential oil, from about 5%-20% of sea kelp bioferment (extract of fermented seaweed), from about 0.01% to about 30% macadamia nut oil, from about 0.01% to about 5% coconut oil, from about 15% to about 90% emu oil. This mixture may be particularly useful for its anti-aging, skin brightening, and cosmetic moisturizing properties. The formulation may, e.g., be used as a face mask.

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. For example, the formulation may comprise from about 0.01% to about 7% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), about 0.01% to about 5% vitamin C, from about 0.01% to about 10% of niacinamide, from about 0.01% to about 3% glutathione, from about 0.001% to about 10% saturated dead sea salt solution, from about 0.01% to about 30% hyaluronic acid, from about 0.01% to about 30% vegetable glycerin, from about 0.01% to about 20% lecithin, from about 5%-30% of sea kelp bioferment (extract of fermented seaweed), from about 0.01% to about 30% macadamia nut oil, from about 0.01% to about 5% coconut oil, from about 15% to about 90% emu oil. These formulations are particularly useful for treatment of burns. They are intended to be applied to the intact, non-erythematous skin near a burned area, but not within the burned area.

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. The formulation may, e.g., comprise from about 0.01% to about 7% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), about 0.01% to about 25% vitamin C, from about 0.01% to about 1% licorice root extract, from about 0.01% to about 1% ginger root extract, from about 1% to about 10% ginger root essential oil, from about 0.01% to about 5% of niacinamide, from about 0.01% to about 6% of essential oil of kaempferia galanga, from about 0.01% to about 3% glutathione, from about 0.001% to about 10% saturated dead sea salt solution, from about 0.01% to about 30% hyaluronic acid, from about 0.01% to about 30% vegetable glycerin, from about 0.01% to about 10% German chamomile essential oil, from about 0.01% to about 10% Moroccan chamomile essential oil, from about 0.01% to about 10% Roman chamomile essential oil, from about 0.01% to about 3% jasmine essential oil, from about 0.01% to about 3% calamus essential oil, from about 0.01% to about 5% lemon essential oil, from about 0.01% to about 5% eucalyptus essential oil, from about 0.01% to about 5% rosemary essential oil, from about 0.01% to about 5% clove essential oil, from about 0.01% to about 5% cinnamon essential oil, from about 0.01% to about 5% cinnamon leaf essential oil, from about 0.01% to about 5% ravintsara essential oil, from about 0.01% to about 20% frankincense essential oil, from about 0.01% to about 20% myrrh essential oil, from about 0.01% to about 20% lecithin, from about 0.001% to about 5% gallic acid, from about 0.001% to about 5% turmeric essential oil, from about 5%-20% of sea kelp bioferment (extract of fermented seaweed), from about 0.01% to about 30% macadamia nut oil, from about 0.01% to about 5% coconut oil, from about 15% to about 90% emu oil. These formulations are particularly useful for treatment of burns. They are intended to be applied to the intact, non-erythematous skin near a burned area, but not within the burned area.

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. The formulation may, e.g., comprise from about 0.01% to about 7% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), about 0.01% to about 25% vitamin C, from about 0.01% to about 1% licorice root extract, from about 0.01% to about 1% ginger root extract, from about 1% to about 10% ginger root essential oil, from about 0.01% to about 10% of niacinamide, from about 0.01% to about 1% of each of the following vitamins: B1, B2, B5, B6, B7, B9, from about 0.01% to about 6% of essential oil of kaempferia galanga, from about 0.01% to about 3% glutathione, from about 0.001% to about 10% saturated dead sea salt solution, from about 0.01% to about 30% hyaluronic acid, from about 0.01% to about 30% vegetable glycerin, from about 0.01% to about 10% German chamomile essential oil, from about 0.01% to about 10% Moroccan chamomile essential oil, from about 0.01% to about 10% Roman chamomile essential oil, from about 0.01% to about 3% jasmine essential oil, from about 0.01% to about 3% calamus essential oil, from about 0.01% to about 15% lemon essential oil, from about 0.01% to about 15% eucalyptus essential oil, from about 0.01% to about 15% rosemary essential oil, from about 0.01% to about 15% clove essential oil, from about 0.01% to about 15% cinnamon essential oil, from about 0.01% to about 15% cinnamon leaf essential oil, from about 0.01% to about 15% ravintsara essential oil, from about 0.01% to about 25% frankincense essential oil, from about 0.01% to about 25% myrrh essential oil, from about 0.01% to about 20% lecithin, from about 0.001% to about 5% gallic acid, from about 0.001% to about 5% turmeric essential oil, from about 5%-20% of sea kelp bioferment (extract of fermented seaweed), from about 0.01% to about 30% macadamia nut oil, from about 0.01% to about 5% coconut oil, from about 15% to about 90% emu oil. These formulations are particularly useful for wound healing. They are intended to be applied to the intact, non-erythematous skin near a wound but not on the wounded skin itself.

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. The formulation may, e.g., comprise from about 0.01% to about 3% alpha lipoic acid (final concentration of about 100 to about 1000 mg/ml), from about 0.01% to about 3% calcium (final concentration of about 100 to about 1000 mg/ml), from about 0.01% to about 7% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), about 0.01% to about 25% vitamin C, from about 0.01% to about 1% licorice root extract, from about 0.01% to about 1% ginger root extract, from about 1% to about 10% ginger root essential oil, from about 0.01% to about 10% of niacinamide, from about 0.01% to about 1% of each of the following vitamins: B1, B2, B5, B6, B7, B9, from about 0.01% to about 6% of kaempferia galanga essential oil, from about 0.01% to about 6% of geranium essential oil, from about 0.01% to about 3% glutathione, from about 0.001% to about 10% saturated dead sea salt solution, from about 0.01% to about 30% hyaluronic acid, from about 0.01% to about 30% vegetable glycerin, from about 0.01% to about 10% German chamomile essential oil, from about 0.01% to about 10% Moroccan chamomile essential oil, from about 0.01% to about 10% Roman chamomile essential oil, from about 0.01% to about 3% jasmine essential oil, from about 0.01% to about 3% calamus essential oil, from about 0.01% to about 15% lemon essential oil, from about 0.01% to about 15% eucalyptus essential oil, from about 0.01% to about 15% rosemary essential oil, from about 0.01% to about 15% clove essential oil, from about 0.01% to about 15% cinnamon essential oil, from about 0.01% to about 15% cinnamon leaf essential oil, from about 0.01% to about 15% ravintsara essential oil, from about 0.01% to about 25% frankincense essential oil, from about 0.01% to about 25% myrrh essential oil, from about 0.01% to about 20% lecithin, from about 0.001% to about 5% gallic acid, from about 0.001% to about 5% turmeric essential oil, from about 5%-20% of sea kelp bioferment (extract of fermented seaweed), from about 0.01% to about 30% macadamia nut oil, from about 0.01% to about 5% coconut oil, from about 15% to about 90% emu oil. These formulations are particularly useful for wound healing, especially to address pitting edema, lymphedema, and neuropathic tissue. They are intended to be applied to the intact, non-erythematous skin overlying affected areas.

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. The formulation may comprise, e.g., from about 0.01% to about 7% ubiquinol (final concentration of about 30-1000 mg/ml), from about 0.01% to about 5% vitamin A (final concentration of about 5700-10,000 mcg/ml), from about 0.01% to about 10% vitamin D (final concentration of about 3000-8,000 IU/ml), from about 0.01% to about 10% vitamin E (final concentration of about 25-500 mg/ml of d-alpha tocopherol, final concentration of mixed tocopherols, including d-beta, d-gamma, and d-delta tocopherol is from about 0.001 to about 3 mg/ml), from about 0.01% to about 10% vitamin K2 MK7 (final concentration of about 50-1000 mcg/ml), about 0.01% to about 25% vitamin C, from about 0.01% to about 1% licorice root extract, from about 0.01% to about 1% ginger root extract, from about 1% to about 10% ginger root essential oil, from about 0.01% to about 10% of niacinamide, from about 0.01% to about 1% of each of the following vitamins: B1, B2, B5, B6, B7, B9, from about 0.01% to about 6% of essential oil of kaempferia galanga, from about 0.01% to about 3% glutathione, from about 0.001% to about 10% saturated dead sea salt solution, from about 0.01% to about 30% hyaluronic acid, from about 0.01% to about 30% vegetable glycerin, from about 0.01% to about 10% German chamomile essential oil, from about 0.01% to about 10% Moroccan chamomile essential oil, from about 0.01% to about 10% Roman chamomile essential oil, from about 0.01% to about 3% jasmine essential oil, from about 0.01% to about 20% calamus essential oil, from about 0.01% to about 15% lemon essential oil, from about 0.01% to about 15% eucalyptus essential oil, from about 0.01% to about 15% rosemary essential oil, from about 0.01% to about 15% clove essential oil, from about 0.01% to about 15% cinnamon essential oil, from about 0.01% to about 15% cinnamon leaf essential oil, from about 0.01% to about 15% ravintsara essential oil, from about 0.01% to about 25% frankincense essential oil, from about 0.01% to about 25% myrrh essential oil, from about 0.01% to about 20% lecithin, from about 0.001% to about 5% gallic acid, from about 0.001% to about 5% turmeric essential oil, from about 5%-20% of sea kelp bioferment (extract of fermented seaweed), from about 0.01% to about 30% macadamia nut oil, from about 0.01% to about 5% coconut oil, from about 15% to about 90% emu oil. These formulations are particularly useful for wound healing, especially to improve appearance of keloid and scar tissue. They are intended to be applied on the intact keloid or scar tissue.

In certain embodiments, the invention is directed to a formulation comprising a mixture comprising, in % by volume, from about 15% to about 25% biosilicates loaded with at least one ingredient selected from the group comprising minerals, amino acids, vitamins and other bioactive compounds for long-acting relief of pain, and delivery of substances required, e.g., for tissue repair. The formulation may comprise, about 10% to about 30% Moroccan chamomile essential oil, from about 2% to about 30% Roman chamomile essential oil, from about 0.01% to about 3% of German chamomile essential oil, from about 6% to about 9% jasmine essential oil, from about 0.05% to about 5% cinnamon leaf essential oil, from about 5% to about 20% frankincense essential oil, from about 5% to about 20% myrrh essential oil, from about 2% to about 4% coconut oil, from about 25% to about 35% macadamia nut oil, from about 30% to about 99% emu oil. In certain embodiments, the invention is directed to a formulation that is half the strength as listed. These formulations may be particularly useful in treating leukoplakia and tongue lesions.

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. The formulation may comprise from about 0.01% to about 0.05% ubiquinol (final concentration of about 1-5 mg/ml), from about 0.01% to about 0.05% vitamin A (final concentration of about 50-100 mcg/ml), from about 0.01% to about 0.05% vitamin D (final concentration of about 100-400 IU/ml), from about 0.01% to about 0.05% vitamin E (final concentration of about 5-15 mg/ml of d-alpha tocopherol, final concentration of mixed tocopherols, including d-beta, d-gamma, and d-delta tocopherol is from about 0.001 to about 1 mg/ml), from about 0.01% to about 0.05% vitamin K2 MK7 (final concentration of about 20-50 mcg/ml), about 0.01% to about 30% Moroccan chamomile essential oil, from about 0.01% to about 30% Roman chamomile essential oil, from about 0.01% to about 20% German chamomile essential oil, from about 1% to about 9% lecithin, from about 0.05% to about 5% gallic acid, from about 1% to about 20% frankincense essential oil, from about 1% to about 20% myrrh essential oil, from about 2% to about 4% coconut oil, from about 25% to about 35% macadamia nut oil, from about 30% to about 99% emu oil. These formulations may be particularly useful for treating Ulcerative Colitis/Inflammatory Bowel Disease/Irritable Bowel Disease.

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. For example, the formulation may comprise from about 0.01% to about 20% Moroccan chamomile essential oil, from about 0.01% to about 0.05% jasmine essential oil, from about 0.01% to about 5% orange essential oil, from about 10% to about 40% saturated dead sea salt solution, from about 1% to about 9% lecithin, from about 0.05% to about 5% gallic acid, from about 1% to about 20% frankincense essential oil, from about 1% to about 20% myrrh essential oil, from about 2% to about 4% coconut oil, from about 10% to about 15% macadamia nut oil, from about 30% to about 99% emu oil. These formulations may be particularly useful for treating Restless Leg Syndrome and muscle cramps.

In certain embodiments, the invention is directed to a formulation comprising a mixture comprising, in % by volume, from about 0.01% to about 2% Moroccan chamomile essential oil, from about 1% to about 3% coconut oil, from about 4% to about 7% macadamia nut oil, from about 1% to about 3% vegetable glycerin, from about 0.01%-5% melatonin (for a final concentration of about 100 to about 160 mcg/spray), and from about 80% to about 99% emu oil. These formulations may be particularly useful for treating jetlag, insomnia, and may be administered as a nasal spray for targeted delivery to vasculature nearest the brain (e.g., one spray per nostril 30 minutes before desired bedtime).

In certain embodiments, the invention is directed to a formulation comprising a mixture comprising, in % by volume, from about 2% to about 30% biosilicates loaded with at least one ingredient selected from the group comprising minerals, amino acids, vitamins and other bioactive compounds, e.g., for long-acting delivery of substances required for tissue repair. The formulation may comprise, e.g., from about 0.01% to about 7% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), from about 0.001% to about 10% saturated dead sea salt solution, from about 0.01% to about 20% ginger essential oil, from about 0.01% to about 20% ginger extract, from about 2% to about 10% licorice root extract, from about 0.05% to about 15% polygonum multifloridum extract, from about 0.05% to about 15% cordyceps extract, from about 0.05% to about 15% bupleurum extract, from about 0.01% to about 3% kaempferia galanga essential oil, from about 0.01% to about 5% lemon essential oil, from about 0.01% to about 5% eucalyptus essential oil, from about 0.01% to about 15% rosemary essential oil, from about 0.01% to about 5% clove essential oil, from about 0.01% to about 5% cinnamon essential oil, from about 0.01% to about 5% cinnamon leaf essential oil, from about 0.01% to about 5% ravintsara essential oil, from about 0.01% to about 20% frankincense essential oil, from about 0.01% to about 20% myrrh essential oil, from about 0.01% to about 6% pine needle essential oil, from about 0.01% to about 10% lecithin, from about 0.001% to about 5% gallic acid, from about 0.001% to about 5% turmeric essential oil, from about 0.01% to about 30% macadamia nut oil, from about 0.01% to about 5% coconut oil, from about 15% to about 90% emu oil. These formulations may be particularly useful for treating alopecia.

In certain embodiments, the invention is directed to a formulation comprising a mixture comprising, in % by volume, from about 5% to about 70% biosilicates loaded with at least one ingredient selected from the group comprising minerals, amino acids, vitamins and other bioactive compounds, e.g., for long-acting delivery of substances required for tissue repair, with biosilicates loaded with a 1:1:1:1 mixture of polygonum multifloridum (from about 0.05% to about 15% by volume), cordyceps extract (from about 0.05% to about 15% by volume), bupleurum (from about 0.05% to about 15% by volume), licorice root extract (from about 2% to about 10% by volume), from about 0.01% to about 7% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), from about 0.001% to about 10% saturated dead sea salt solution, from about 0.01% to about 20% ginger essential oil, from about 0.01% to about 20% ginger extract, from about 2% to about 10% licorice root extract, from about 0.05% to about 15% polygonum multifloridum extract, from about 0.05% to about 15% cordyceps extract, from about 0.05% to about 15% bupleurum extract, from about 0.01% to about 3% kaempferia galanga essential oil, from about 0.01% to about 5% lemon essential oil, from about 0.01% to about 5% eucalyptus essential oil, from about 0.01% to about 15% rosemary essential oil, from about 0.01% to about 5% clove essential oil, from about 0.01% to about 5% cinnamon essential oil, from about 0.01% to about 5% cinnamon leaf essential oil, from about 0.01% to about 5% ravintsara essential oil, from about 0.01% to about 20% frankincense essential oil, from about 0.01% to about 20% myrrh essential oil, from about 0.01% to about 6% pine needle essential oil, from about 0.01% to about 10% lecithin, from about 0.001% to about 5% gallic acid, from about 0.001% to about 5% turmeric essential oil, from about 0.01% to about 30% macadamia nut oil, from about 0.01% to about 5% coconut oil, from about 15% to about 90% emu oil. These formulations may be particularly useful for treating alopecia. They may be incorporated into hair loss scalp mask. In some of the embodiments, they may be massaged into scalp and left on for at least 30 minutes, ideally with exposure to heat to dilate scalp blood vessels (such as, e.g., via a near-infrared lamp).

In certain embodiments, the invention is directed to a formulation comprising a mixture comprising, in % by volume, from about 5% to about 40% biosilicates loaded with at least one ingredient selected from the group comprising minerals, amino acids, vitamins and other bioactive compounds, e.g., for long-acting delivery of substances required for tissue repair, with biosilicates loaded with a 1:1:1:1 mixture of polygonum multifloridum (from about 0.05% to about 15% by volume), bupleurum (from about 0.05% to about 15% by volume), from about 0.01% to about 7% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), from about 0.001% to about 10% saturated dead sea salt solution, from about 0.01% to about 20% ginger essential oil, from about 0.01% to about 20% ginger extract, from about 2% to about 10% licorice root extract, from about 0.05% to about 15% polygonum multifloridum extract, from about 0.05% to about 15% cordyceps extract, from about 0.05% to about 15% bupleurum extract, from about 0.01% to about 3% kaempferia galanga essential oil, from about 0.01% to about 5% lemon essential oil, from about 0.01% to about 5% eucalyptus essential oil, from about 0.01% to about 15% rosemary essential oil, from about 0.01% to about 5% clove essential oil, from about 0.01% to about 5% cinnamon essential oil, from about 0.01% to about 5% cinnamon leaf essential oil, from about 0.01% to about 5% ravintsara essential oil, from about 0.01% to about 20% frankincense essential oil, from about 0.01% to about 20% myrrh essential oil, from about 0.01% to about 6% pine needle essential oil, from about 0.01% to about 10% lecithin, from about 0.001% to about 5% gallic acid, from about 0.001% to about 5% turmeric essential oil, from about 0.01% to about 30% macadamia nut oil, from about 0.01% to about 5% coconut oil, from about 15% to about 90% emu oil, from about 20% to about 90% decyl glucoside (nonionic surfactant derived from sugar and plant oil, very mild and non-irritating, good for sensitive skin), from about 20% to about 90% sodium lauroyl lactylate (nonionic surfactant derived from coconut oil and coconut milk, provides a soothing feel). These formulations are particularly useful for incorporation into shampoos and conditioners for the treatment of hair loss. In some of the embodiments, they may be massaged into scalp and left on for a sufficient amount time to allow absorption.

In certain embodiments, a formulation comprises a mixture comprising, in % by volume, from about 1% to about 3% macadamia nut oil, from about 0.01% to about 0.2% coconut oil, from about 1% to about 3% lemongrass essential oil, from about 1% to about 3% German chamomile essential oil, from about 1% to about 3% Roman chamomile essential oil, from about 1% to about 3% Moroccan chamomile essential oil, and from about 80% to about 99% emu oil. These formulations may be particularly useful as a galactagogue preparation. In some of the embodiments, they may be applied topically to axillae and upper chest (away from the nipples) to encourage milk production in breastfeeding mothers.

In certain embodiments, a formulation comprises a mixture comprising, in % by volume, from about 5% to about 12% water extract of kaffir lime leaf, from about 10% to about 24% water extract of galangal, from about 5% to about 12% water extract of lemongrass, from about 0.1% to about 2% essential oil of kaffir lime leaf, from about 0.2% to about 4% essential oil of galangal, from about 0.1% to about 2% essential oil of lemongrass, from about 0.01% to about 2% of yuzu essential oil, from about 0.01% to about 2% of rosemary essential oil, from about 2% to about 30% of blackseed essential oil, from about 2% to about 40% of fish oil, from about 0.01% to about 2% of palmarosa essential oil, from about 0.01% to about 2% of niaouli essential oil, from about 0.01% to about 2% of spearmint essential oil, from about 0.01% to about 2% of coriander seed essential oil, from about 0.01% to about 2% of geranium essential oil, from about 0.01% to about 2% of zanthoxylum armatum essential oil, from about 0.01% to about 2% of turmeric essential oil, from about 0.01% to about 2% of garlic essential oil, from about 2% to about 10% of ginger essential oil, from about 0.01% to about 2% of lemon essential oil, from about 1% to about 2% of ubiquinol, from about 0.01% to about 2% of yuzu essential oil, from about 0.01% to about 2% of cassia essential oil, from about 0.01% to about 2% of cinnamon leaf essential oil, from about 0.01% to about 2% of lime essential oil, from about 0.01% to about 2% of grapefruit essential oil, from about 2% to about 5% macadamia nut oil, from about 0.5% to about 1% coconut oil and from about 30% to about 99% emu oil. These formulations may be particularly useful for treating diabetes/hyperlipidemia/obesity/coronary artery disease/metabolic syndrome/atherosclerosis/hypertriglyceridemia. In some of the embodiments, they are administered orally (e.g., 1 gram every morning).

In certain embodiments, a formulation comprises a mixture comprising, in % by volume, from about 5% to about 75% frankincense essential oil, from about 5% to about 50% myrrh essential oil, from about 5% to about 10% vanilla essential oil, from about 0.1% to about 10% bitter orange essential oil, from about 0.2% to about 12% essential oil of lemon balm (melissa), from about 0.1% to about 20% glycine (for a final concentration of about 0.5 g/ml to about 1 g/ml), from about 0.01% to about 2% of cinnamon essential oil, from about 0.01% to about 2% of lemon essential oil, from about 0.01% to about 2% of eucalyptus essential oil, from about 0.01% to about 2% of clove essential oil, from about 0.01% to about 2% ravintsara essential oil, from about 0.01% to about 30% of FDGE biosilicates loaded with compounds for tissue repair, from about 0.01% to about 2% of German chamomile essential oil, from about 0.01% to about 2% of lecithin, from about 0.01% to about 2% of flaxseed oil, from about 0.01% to about 0.05% of alpha lipoic acid (final concentration from about 100 mg/ml to about 1000 mg/ml), from about 0.01% to about 2% of gallic acid (final concentration from about 10 mg/ml to about 70 mg/ml), from about 0.01% to about 2% of Roman chamomile essential oil, from about 0.01% to about 2% of Moroccan chamomile essential oil, from about 0.01% to about 2% of jasmine essential oil, from about 0.01% to about 2% of neroli oil, from about 10% to about 20% of grape seed extract (standardized to 95% proanthocyanidins), from about 10% to about 20% of grape skin extract (standardized to 95% proanthocyanidins), from about 5% to about 12% water extract of kaffir lime leaf, from about 10% to about 24% water extract of galangal, from about 5% to about 12% water extract of lemongrass, from about 0.1% to about 2% essential oil of kaffir lime leaf, from about 0.2% to about 4% essential oil of galangal, from about 0.1% to about 2% essential oil of lemongrass, from about 0.01% to about 2% of yuzu essential oil, from about 2% to about 40% of fish oil, from about 0.01% to about 2% of palmarosa essential oil, from about 0.01% to about 2% of niaouli essential oil, from about 0.01% to about 2% of spearmint essential oil, from about 0.01% to about 2% of coriander seed essential oil, from about 0.01% to about 2% of geranium essential oil, from about 0.01% to about 2% of zanthoxylum armatum essential oil, from about 0.01% to about 2% of turmeric essential oil, from about 0.01% to about 2% of garlic essential oil, from about 0.01% to about 2% of lemon essential oil, from about 0.01% to about 2% of yuzu essential oil, from about 0.01% to about 2% of cassia essential oil, from about 0.01% to about 2% of lime essential oil, from about 0.01% to about 2% of grapefruit essential oil, cordyceps extract (from about 0.05% to about 5% by volume), bupleurum (from about 0.05% to about 5% by volume), from about 0.01% to about 5% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 5% vitamin B3 (final concentration of about 500-4000 mg/ml), from about 0.01% to about 5% niacinamide (final concentration of about 500-4000 mg/ml), from about 0.01% to about 5% vitamin C (final concentration of about 1000-4000 mg/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), from about 0.001% to about 10% saturated dead sea salt solution, from about 0.01% to about 20% ginger essential oil, from about 0.01% to about 20% ginger extract, from about 2% to about 5% licorice root extract, from about 0.01% to about 30% of rosemary essential oil, from about 0.01% to about 20% of cinnamon leaf essential oil, from about 2% to about 30% of blackseed essential oil, from about 2% to about 5% macadamia nut oil, from about 0.5% to about 1% coconut oil and from about 30% to about 99% emu oil. These formulations may be particularly useful for treating diabetes/hyperlipidemia/obesity/metabolic syndrome/hypertriglyceridemia/insulin resistance/abnormal sleep debt/insulin resistance/osteopenia/osteoporosis/anemia of chronic disease. In some of the embodiments, they are administered orally (e.g., 1 gram every morning).

In certain embodiments, a formulation comprises a mixture comprising, in % by volume, from about 5% to about 75% frankincense essential oil, from about 5% to about 50% myrrh essential oil, from about 5% to about 10% vanilla essential oil, from about 0.1% to about 10% bitter orange essential oil, from about 0.2% to about 12% essential oil of lemon balm (melissa), from about 0.1% to about 20% glycine (for a final concentration of 1 g/ml), from about 0.01% to about 1% of rosemary essential oil, from about 0.01% to about 1% of cinnamon essential oil, from about 0.01% to about 1% of lemon essential oil, from about 0.01% to about 1% of cinnamon leaf essential oil, from about 0.01% to about 1% of eucalyptus essential oil, from about 0.01% to about 1% of clove essential oil, from about 0.01% to about 1% ravintsara essential oil, from about 2% to about 5% macadamia nut oil, from about 0.5% to about 1% coconut oil and from about 30% to about 99% emu oil. These formulations may be particularly useful for treating abnormal sleep debt. In some of these embodiments, they are administered orally (e.g., 1 gram every morning).

In certain embodiments, a formulation comprises a mixture comprising, in % by volume, cordyceps extract (from about 0.05% to about 5% by volume), bupleurum (from about 0.05% to about 5% by volume), from about 0.01% to about 5% ubiquinol (final concentration of about 30-1000 mg/ml), from about 0.01% to about 4% vitamin A (final concentration of about 5700-6500 mcg/ml), from about 0.01% to about 10% vitamin D (final concentration of about 3000-4000 IU/ml), from about 0.01% to about 5% vitamin B3 (final concentration of about 500-4000 mg/ml), from about 0.01% to about 5% niacinamide (final concentration of about 500-4000 mg/ml), from about 0.01% to about 5% vitamin C (final concentration of about 1000-4000 mg/ml), from about 0.01% to about 10% vitamin E (final concentration of about 25-35 mg/ml of d-alpha tocopherol, final concentration of mixed tocopherols, including d-beta, d-gamma, and d-delta tocopherol is from about 0.001 to about 1 mg/ml), from about 0.01% to about 10% vitamin K2 MK7 (final concentration of about 50-100 mcg/ml), from about 0.001% to about 10% saturated dead sea salt solution, from about 0.01% to about 20% ginger essential oil, from about 0.01% to about 20% ginger extract, from about 2% to about 5% licorice root extract, from about 0.01% to about 30% of rosemary essential oil, from about 0.01% to about 20% of cinnamon leaf essential oil, from about 2% to about 30% of blackseed essential oil, from about 2% to about 5% macadamia nut oil, from about 0.5% to about 1% coconut oil and from about 30% to about 99% emu oil. These formulations may be particularly useful for treating osteopenia, osteoporosis, and anemia of chronic disease. In some of the embodiments, they are administered orally (e.g., 1-4 grams every morning).

In certain embodiments, a formulation comprises a mixture comprising, in % by volume, from about 5% to about 20% of dead sea salt hydrated biosilicates, from about 10% to about 25% dead sea salt reconstituted with sterile filtered water, from about 10% to about 20% of grape seed extract (standardized to 95% proanthocyanidins), from about 10% to about 20% of grape skin extract (standardized to 95% proanthocyanidins), from about 10% to about 20% of resveratrol (standardized to at least 8% potency yield), from about 10% to about 20% of sterile filtered water, from about 5% to about 30% lecithin, from about 50% to about 90% emu oil, from about 1% to about 3% macadamia nut oil, and from about 0.01% to about 0.2% coconut oil. In certain embodiments, a formulation may be made into capsules, to be taken orally from about 1 g-4 g daily which may be particularly useful for improving neurologic function and reduce amyloid-beta peptide aggregation, prevent dementia, Alzheimer's disease, and Parkinson's disease. In certain embodiments, a formula may be as described above, but formulated with 1000 ml vegetable glycerin in place of lecithin, to be administered as a nasal spray 1 ml spray 1-4 times daily to deliver bioactive ingredients close to the brain vasculature.

In any one of the formulations listed herein, the formulation may be diluted with a base composition to half the strength of the additional ingredients in the formulation.

In any one of the formulations listed herein, the formulation may comprise one or more exosome(s). Exosomes may, e.g., be loaded onto biosilicates (e.g., FDGE biosilicates) for, e.g., localized and/or extended release.

Any of the formulations listed herein may include from about 1% to about 45% of Food Grade Diatomaceous Earth (FDGE) biosilicates or another pharmaceutically acceptable matrices. In some of the embodiments, the biosilicates may be preloaded with one or more ingredient(s) to create a fraction which provide extended release of one or more ingredient(s).

The formulation may be included into a topical preparation (e.g., a solution, an emulsion (e.g., an oil/oil emulsion), a cream, an ointment, or a balm). The formulation may also be incorporated into a shampoo, conditioner, a mask, a face wash, a body wash, a cleanser, a toner, a wrinkle cream, an age spot fading cream, a serum, a dental preparation, a gum, floss, nasal spray, sunblock, self-tan product, a galactagogue preparation, a needle-free vaccine, a needle-free medicine (e.g., transdermal insulin), a henna preparation, a moisturizer, a keloid and scar preparation, an eyelash and eyebrow growth stimulating serum, a hair gloss, a hair spray, a hair mousse, a hair mask, a topical cream for erectile dysfunction, e.g. when admixed with PDE5 inhibitors, an oral preparation to be taken internally to heal the gut lining in Ulcerative Colitis/Crohn's Disease, Irritable Bowel Disease, or a preparation for HIV mucositis, aphthous ulcers, diverticulitis, colitis, and other mucosal irritations, an oral preparation to treat abnormal sleep debt, an oral preparation to treat osteoporosis, osteopenia, and anemia of chronic disease, an oral preparation to be taken internally to prevent or slow progression of a prediabetic patient from developing or progression of diabetes/obesity/hyperlipidemia/hypertriglyceridemia/metabolic syndrome/atherosclerosis/coronary artery disease, an oral preparation to improve insulin sensitivity, an oral preparation to be taken internally to prevent or slow progression of Alzheimer's Disease, Parkinson's Disease or Multiple Sclerosis, an oral preparation to prevent or slow development or progression of cancer, an inhaled nebulized preparation, e.g., to treat asthma and Chronic Obstructive Pulmonary Disease (COPD), a topical preparation for treatment of Lichen Sclerosis (LS), a topical preparation for treatment of Lichen Planus (LP), a topical preparation to alleviate Raynaud's Phenomena, a topical preparation to alleviate edema and lymphedema, a topical preparation to deliver natural antimicrobials into wounds to promote rapid wound healing, a set of antibiotic drops for treating infections of the ears or eyes, a topical gel that can quickly alleviate chest pain when applied over the left chest, a topical preparation that can quickly alleviate hypertension when applied over the great vessels to prevent a stroke, a topical preparation to be applied over the head and neck to alleviate headache, etc. This preparation, or modifications thereof, can be admixed with existing pharmaceuticals to enhance delivery. The "pharmaceuticals" as used herein include vitamins, minerals and drugs approved by US FDA for use in humans and/or animals.

The formulation may also be an oral formulation. In some of these embodiments, the formulation is administered orally and incorporates into membranes of gastrointestinal tract but is not absorbed into the systemic circulation. In other embodiments, the formulation is absorbed into the systemic formulation in an amount to provide an intended effect (e.g., a therapeutically beneficial effect). In some embodiments, the formulation may also be coated over a substrate. A substrate may e.g., a nanoparticle, a Food-Grade Diatomaceous Earth (FGDE) or a pharmaceutically acceptable matrix. The substrate may comprise a phospholipid, a ceramide, cholesterol, a fatty acid, an oil, a vitamin, a mineral, an amino acid, a hyaluronic acid, a fusogen, a biofermentation product of a fruit or plants, an additional therapeutic agent (e.g., a drug approved by U.S. FDA for use in humans), or a combination of two or more of the foregoing. The formulation may be, e.g., in the form of an ointment or another topical preparation, tor formulated to be administered orally, intranasally, intravenously, intramuscularly, during open surgery, as a suppository or via other routes.

The fatty acid composition of the formulation may be adjusted using the base compositions and additional ingredients disclosed herein to render the formulation capable of crossing, integrating, modulating, regulating, or restoring cell membranes of the following cells: skin cells, brain cells, fibroblast cells, endothelial cells (cells lining the blood vessels), macrophages, immune cells, red blood cells, white blood cells, lymphocytes, leukocytes, hepatocytes, neurons, astrocytes, microglia, oligodendrocytes, bronchial endothelial cells, respiratory interstitial cells, sustentacular cells, olfactory bulb neurons, adipocytes, dermal fibroblasts, muscle cells, cardiomyocytes, pancreatic islet cells, Brunner's gland cell in the duodenum (secrete enzymes and alkaline mucus), all glandular cells, goblet cells of the respiratory mucosa (secrete mucus), goblet cells of the digestive tract (secrete mucus), foveolar cells (secrete mucus), chief cells (secrete pepsinogen), parietal cells (secrete HCL), pancreatic acinar cells (secrete bicarbonate and digestive enzymes), Paneth cells of the small intestine (secrete lysozyme), type II pneumocytes of the lungs (secrete surfactant), club cells of the lung, type I pneumocytes, epithelial cells of every organ, centroacinar cells of the pancreas, intercalated duct cell of the pancreas, intestinal brush border cells with microvilli, enteroendocrine cells, K cells (secrete gastric inhibitory peptide), L cells (secrete glucagon-like peptide-1, peptide YY3-36, oxyntomodulin, and glucagon-like peptide-2), I cells (secrete cholecystokinin), G cells (secrete gastrin), enterochromaffin cells (secrete serotonin), enterochromaffin-like cells (secrete histamine), N cells (secrete neurotensin), S cells (secrete secretin), D cells (secrete somatostatin), Mo cell or M cell (secrete motilin), megakaryocytes, bone marrow cells, bone cells, osteoclasts, osteoblasts, mast cells, thyroid epithelial cells, parafollicular cells of the thyroid, parathyroid chief cells, oxyphil cells, alpha cells of the pancreas (secrete glucagon), beta cells of the pancreas (secrete insulin and amylin), delta cells of the pancreas, secrete somatostatin), epsilon cells of the pancreas (secrete ghrelin), PP cells, a.k.a. gamma cells of the pancreas (secrete pancreatic polypeptide), salivary gland mucous cells, salivary gland serous cells, Von Ebner's gland cells in the tongue, mammary gland cells (secrete milk), lacrimal gland cells (secrete tear), ceruminous gland cells in ear (secrete earwax), eccrine sweat gland dark cells (secrete glycoprotein), eccrine sweat gland clear cells (secrete small molecule), apocrine sweat gland cells (secrete odoriferous secretions; are sex-hormone sensitive), gland of Moll cells in eyelid (specialized sweat glands), sebaceous gland cells (secrete lipid-rich sebum), Bowman's gland cells in nose, olfactory epithelial cells, hair cells, hair follicle cells, endogenous stem cells of each organ, corticotropes, gonadotropes, lactotropes, melanotropes, somatotropes, thyrotropes, magnocellular neurosecretory cells (secrete oxytocin and vasopressin), parvocellular neurosecretory cells (secrete thyrotropin-releasing hormone, corticotropin-releasing hormone, vasopressin, oxytocin, neurotensin, and prolactin), chromaffin cells of the adrenal glands, keratinocytes, epidermal basal cells, melanocytes, trichocytes (give rise to hair and nail cells), medullary hair shaft cells, cortical hair shaft cells, cuticular hair shaft cells, Huxley's layer hair root sheath cells, Henle's layer hair root sheath cells, outer root sheath hair cells, surface epithelial cells of the cornea, tongue, mouth, nasal cavity, distal anal canal, distal urethra, distal vagina; basal cells (stem cells of the cornea, tongue, mouth, nasal cavity, distal anal canal, distal urethra and distal vagina), intercalated duct cells of the salivary glands, striated duct cells of the salivary glands, lactiferous duct cells of the mammary glands, ameloblasts (secrete and deposit tooth enamel), odontoblasts (secrete and form tooth dentin), cementoblasts (secrete and form tooth cementum), auditory inner hair cells of the organ of Corti, auditory outer hair cells of the organ of Corti, basal cells of olfactory epithelium (stem cells for olfactory neurons), cold-sensitive primary sensory neurons, heat-sensitive primary sensory neurons, Merkel cells of the epidermis, olfactory receptor neurons, pain-sensitive primary sensory neurons, photoreceptor rod cells, photoreceptor blue-sensitive cone cells of the eye, photoreceptor green-sensitive cone cells of the eye, photoreceptor red-sensitive cone cells of the eye, proprioceptive primary sensory neurons, chemoreceptor glomus cells of the carotid body cell (blood pH sensors), outer hair cells of vestibular system of ear (acceleration and gravity sensors), taste receptor cells of the taste buds, cholinergic neurons, adrenergic neurons, peptidergic neurons, inner pillar cells of the organ of Corti, outer pillar cells of the organ of Corti, inner phalangeal cells of the organ of Corti, outer phalangeal cells of the organ of Corti, border cells of the organ of Corti, vestibular apparatus supporting cells, taste bud supporting cells, olfactory epithelium supporting cells, olfactory ensheathing cells, Schwann cells, satellite glial cells, enteric glial cells, interneurons, basket cells, cartwheel cells, stellate cells, Golgi cells, granule cells, Lugaro cells, unipolar brush cells, Martinotti cells, chandelier cells, Cajal-Retzius cells, double-bouquet cells, neurogliaform cells, retina horizontal cells, amacrine cells, starburst amacrine cells, spinal interneurons, Renshaw cells, principal cells, spindle neurons, fork neurons, pyramidal cells, place cells, grid cells, speed cells, head direction cells, Betz cells, stellate cells, boundary cells, bushy cells, Purkinje cells, medium spiny neurons, ependymal cells, tanycytes, pituicytes, lens cells, anterior lens epithelial cells, corneal epithelial cells, crystallin-containing lens fiber cells, white fat cells, brown fat cells, beige fat cells, other adipocytes, liver adipocytes, cells of the adrenal cortex, cells of the zona glomerulosa (secrete mineralocorticoid), cells of the zona fasciculata (secrete glucocorticoid), cells of the zona reticularis (secrete androgen), theca interna cells of the ovarian follicle (secrete estrogen), corpus luteum cells of the ruptured ovarian follicle (secrete progesterone), granulosa lutein cells, theca lutein cells, Leydig cells of the testes (secrete testosterone), seminal vesicle cells (secrete seminal fluid), prostate gland cells (secrete seminal fluid components), bulbourethral gland cells (secrete mucus), Bartholin's gland cell (secrete vaginal lubricants), gland of Littre cells (secrete mucus), uterus endometrial cells (secrete carbohydrate), juxtaglomerular cells (secrete renin), myometrial cells, macula densa cells of the kidney, peripolar cells of the kidney, mesangial cells of the kidney, parietal epithelial cells, podocytes, proximal tubule brush border cells, loop of Henle thin segment cells, kidney distal tubule cells, kidney collecting duct cells, principal cells, intercalated cells, transitional epithelial cells (lining urinary bladder), duct cells of seminal vesicles, duct cells of prostate gland, etc., efferent duct cells, epididymal principal cells, epididymal basal cells, planum semilunatum epithelial cells of the vestibular system of the ear (secrete proteoglycan), organ of Corti interdental epithelial cells (secrete tectorial membrane covering the hair cells), loose connective tissue fibroblasts, cells of the fascia, corneal fibroblasts (corneal keratocytes), tendon fibroblasts, bone marrow reticular tissue fibroblasts, nonepithelial fibroblasts, pericytes, hepatic stellate cells (Ito cells), nucleus pulposus cells of the intervertebral disc, hyaline cartilage chondrocytes, fibrocartilage chondrocytes, elastic cartilage chondrocytes, osteoblasts/osteocytes, osteoprogenitor cells (stem cells of the osteoblast), hyalocytes of the vitreous body of the eye, stellate cells of the perilymphatic space of the ear, pancreatic stellate cells, red skeletal muscle cells (slow twitch), white skeletal muscle cells (fast twitch), intermediate skeletal muscle cells, nuclear bag cells of the muscle spindle, nuclear chain cells of muscle spindles, myosatellite cells (stem cells of the muscle), cardiac muscle cells, SA node cells, Purkinje fiber cells, smooth muscle cells, myoepithelial cells of the iris, myoepithelial cells of the exocrine glands, monocytes, connective tissue macrophages associated with each type of tissue or organ, epidermal Langerhans cells, dendritic cells in lymphoid tissue, neutrophil granulocytes and precursors (myeloblasts, promyelocytes, myelocytes, metamyelocytes), eosinophils, granulocytes and precursors (basophil granulocytes and precursors), helper T cells, regulatory T cells, cytotoxic T cells, natural killer T cells, B cells, plasma cells, natural killer cells, hematopoietic stem cells and committed progenitors for the blood and immune system, oogonium cells, oocytes, spermatids, spermatocytes, spermatogonium cells (stem cells for spermatocytes), spennatozoon cells, nurse cells, granulosa cells (in ovaries), Sertoli cells (in testis), epithelial reticular cells (in thymus), and interstitial kidney cells.

The invention is further directed in part to a method of treating a disorder comprising administering a formulation comprising a mixture of fatty acids to a patient in need thereof in an amount and for a duration sufficient to alleviate one or more symptoms of the disorder in a patient. In one embodiment, the mixture has a fatty acid composition that is substantially the same (i.e., approximate) as that of human skin and sebum.

The invention is further directed to a method of treating a symptom of a disease associated with an injury, damage or dysfunction of a cellular membrane function in a mammal.

The disease associated with a dysfunction, injury of damage of a cellular membrane function may, e.g., be pain, eczema, psoriasis, erythema, a burn, a cut, a bruise, a boil, a scar, a keloid, a non-healing wound, acne, rosacea, an allergy, an arthritis, an arthralgia, cancer, a neuropathy, a metabolic syndrome, an infection, a canker sore, an ulcer, Ulcerative Colitis (UC), a mucositis, diverticulitis, celiac disease, a colitis, Crohn's Disease (CD), Irritable Bowel Syndrome (IBS), Inflammatory Bowel Disease (IBD) atherosclerosis, Alzheimer's Disease (AD), Parkinson's Disease (PD), gout, solar lentigo, senile lentigines, skin atrophy, Lichen Sclerosis (LS), Lichen Planus (LP), asthma, Chronic Obstructive Pulmonary Disease (COPD), angina, Coronary Artery Disease (CAD), hypertension (HTN), hyperlipidemia (HLD), Diabetes Mellitus (DM), insulin resistance, metabolic syndrome, a neuropathy, PMS, anxiety, depression, nightmares, insomnia, abnormal sleep debt, neuralgia, sciatica, mastitis, conjunctivitis, a convulsive disorder, alcohol withdrawal, abnormal muscle tension, xerosis, osteoporosis, osteopenia, anemia of chronic disease, fibromyalgia, alopecia, Erectile Dysfunction (ED), Restless Legs Syndrome (RDS), Multiple Sclerosis (MS), urticaria, hemorrhoids, Chronic Fatigue Syndrome (CFS), leukoplakia, edema, heavy lymph load, sunburn, vaginal atrophy, hyperpigmented skin due to aging or prior trauma, or a muscle spasm. The symptom may, e.g., be selected from the group consisting of pain, inflammation, skin irritation, rash, a lesion, a wrinkle, hyperpigmentation, a keloid, a scar, pruritus, itching, indigestion, diarrhea, a cramp, cough, a bronchospasm, a discoloration, and combinations or two or more of the foregoing.

The invention is also directed in part to a method of treating a disorder comprising administering a formulation comprising a mixture of oils, including animal oils and vegetable oils, to a patient in need thereof in an amount and for a duration sufficient to alleviate one or more symptoms of the disorder in a patient. In one embodiment, the mixture has a fatty acid composition that is substantially the same (i.e., approximate) as that of human skin and sebum. In certain embodiments, the formulation is administered topically. In other embodiments, the formulation may be administered orally, intranasally, intravenously, intramuscularly, during open surgery, as a suppository or via other routes of administration.

The invention is also directed in part to a method of treating a disorder comprising administering a formulation comprising a mixture of naturally occurring compounds found in vegetable oils, animal oils, plant matter, mineral matter, exosomes, or other organic materials which have been subjected to fermentation (via bacteria, fungi, or other micro-organisms), e.g., in order to diversify and improve chemical activity of bioactive compounds, which have then been admixed or modified with a mixture of oils to improve delivery of such compounds to treat, improve or ameliorate a disease. A combination of therapeutics designed to address multiple aspects of a disease may be administered in conjunction via topical, oral, intranasal, intravenous, intramuscular, suppository or other routes such as, e.g., applied during open surgery.

The disorders that may be treated with the formulations of the present invention include but are not limited to the following: e.g., abnormal muscle tension, abnormal sleep debt, acne, alcohol withdrawal, allergies, alopecia, Alzheimer's Disease (AD), angina/chest pain, aphthous ulcers, arthritis (e.g., rheumatoid arthritis, osteoarthritis, psoriatic arthritis, etc.), arthralgias induced by chemotherapy, arthralgias caused by autoimmune disease, arthralgias caused by trauma, asthma, atherosclerosis, anxiety, boils, bronchospasm, bruises, burns, canker sores, cancer, celiac disease, Chronic Fatigue Syndrome (CFS), Chronic Obstructive Pulmonary Disease (COPD), colitis, conjunctivitis, Coronary Artery Disease (CAD), cough, cramps/muscle spasms, Crohn's Disease (CD), cuts in skin, depression, dermatitis, Diabetes Mellitus (DM), diaper rash, diverticulitis, eczema, edema, epilepsy and other convulsive disorders, epistaxis due to persistent nasal dryness, Erectile Dysfunction (ED), erythema, fibromyalgia, gingivitis, gout, hair loss, healing of tattoos or other skin wounds, hemorrhoids, HIV mucositis, hypercholesterolemia, hyperlipidemia (HLD), hyperpigmentation, hypertension (HTN), hypertriglyceridemia, increased muscle tension, indigestion, infection, Inflammatory Bowel Disease (IBD), insomnia, Irritable Bowel Syndrome (IBS), itching, keloids, leukoplakia, Lichen Planus (LP), Lichen Sclerosis (LS), lymphedema, mastitis, metabolic syndrome, mucositis, insulin resistance, Multiple Sclerosis (MS), nasal inflammation, neuralgia, neuropathic pain, neuropathy (numbness/paresthesias), nightmares, non-healing wounds, obesity, otitis externa, otitis media, osteopenia, osteoporosis, anemia of chronic disease, pain, Parkinson's Disease (PD), peripheral neuropathy, pharyngitis, poor immune function, pre-menstrual syndrome (PMS), pruritic rashes, psoriasis, rash, Restless Leg Syndrome (RLS), rosacea, scars (including, e.g., keloid and atrophic), sciatica, senile lentigines, skin atrophy from overuse of topical corticosteroids, skin lesions, social anxiety, solar lentigines, strokes, sunburn, topical infections (impetigo, staphylococcal, streptococcal and fungal infections), ulcers, Ulcerative Colitis (UC), unspecified skin irritations, urticaria, vaginal atrophy, wounds, wrinkles, xerosis (dry skin), among others. Formulations can also be formulated to address or improve surfactant production (such as would be useful in reducing atelectasis in patients who have recently undergone surgery); to facilitate lung maturity in neonates, to address acetylcholine deficiency, to improve nutrient absorption, slow down aging by decreasing free radical production and inflammation, decrease risk for or progression of cancer by decreasing free radical production and inflammation, and decrease risk of acute infarctions of the brain and myocardium (e.g. stroke and heart attacks) by improving atherosclerosis.

In certain embodiments, the formulation is administered topically. In other embodiments, the formulation may be administered, intranasally, intravenously, intramuscularly, during open surgery, or a suppository, or via a spray.

DEFINITIONS

Figure 1:
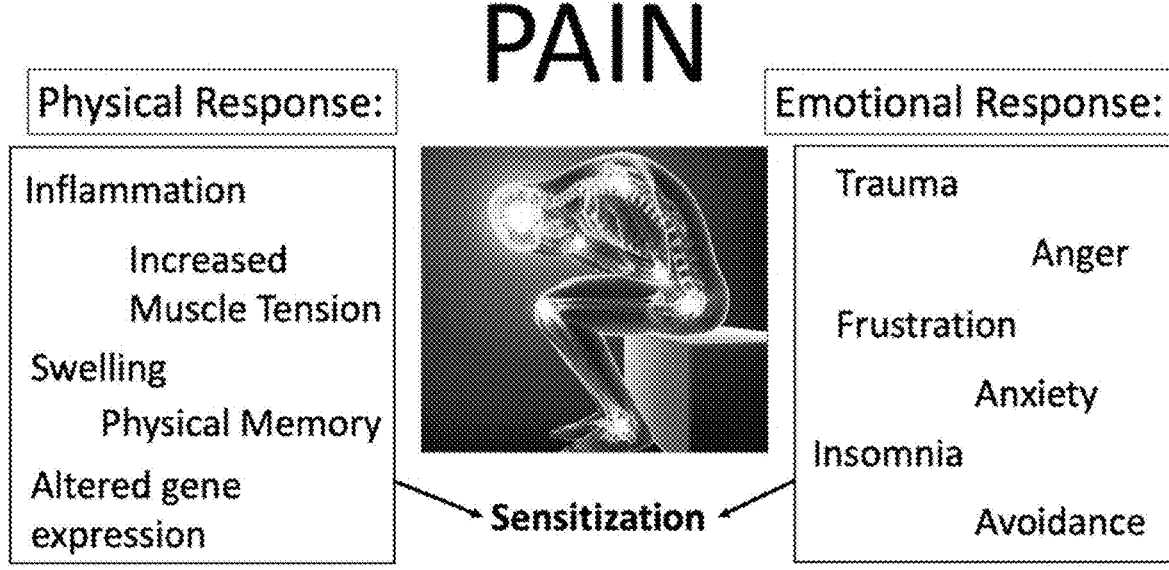
FIG. 1. Pain is a Multifactorial Problem. (image obtained from https://st.depositphotos.com/1812149/2267/i/450/depositphotos_22674323-stock-photo-full-body-pain.jpg)

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely for illustration and does not pose a limitation on the scope of the invention unless otherwise claimed. No language in the specification should be construed as indicating any non-claimed element as essential to the practice of the invention.

The terms "a" and "an" do not denote a limitation of quantity, but rather denote the presence of at least one of the referenced item(s).

The term "about" in the present specification means a value within 20% (±20%) of the value recited immediately after the term "about," including the value equal to the upper limit (i.e., +20%) and the value equal to the lower limit (i.e., −20%) of this range. For example, the phrase "about 100" encompasses any numeric value that is between 80 and 120, including 80 and 120.

The terms "substantially similar" and "substantially identical" and "substantially the same" with reference to a fatty acid composition of a formulation as used herein means that the formulation contains fatty acids of the type and in the amounts that allow the formulation to cross and/or integrate into a membrane or organelle of a cell or modulate a function of an exosome. The terms "substantially similar" and "substantially identical" and "substantially the same" encompass fatty acid compositions that are identical to that of a membrane of a cell or an organelle; and the fatty acid compositions that are not identical to that of a membrane of a cell or an organelle but still allow the formulation to cross and/or integrate into a membrane of a cell or an organelle and/or modulate a function of an exosome. A fatty acid composition that is "substantially similar" or "substantially identical" or "substantially identical" to that of a membrane of a cell or organelle as used in the present specification is different from and does not encompass the fatty acid composition of emu oil, as it, e.g., comprises a higher amount of oleic acid times than emu oil (e.g., at least 1.5 to 2 times higher) than the emu oil.

The term "an organelle" refers to a lipid-bilayer enclosed subcellular differentiated structure within a cell which performs a specific function. An organelle is usually visible under the microscope as a distinct structure or object. Examples would include ribosomes, mitochondria, vacuoles, etc.

The term "exosome" as used in the present specification means a membrane bound extracellular vesicle.

The term "an essential oil" as used in the present specification means a volatile oil or mixture of volatile oils and other substances obtained by chemical extraction from a plant which typically has a characteristic odor or flavor of the plant from which it is obtained. Essential oils may be obtained from just one part of the plant (for example, essential oil of ginger root, vs essential oil of bay leaves). Essential oils may be different depending on the solvent used to extract the bioactive compounds—for example, CO2 extraction vs aqueous extraction vs alcohol extraction may yield different mixtures or proportions of bioactive compounds from the same plant.

The term "short chain fatty acid" or "short chain triglyceride" as used in the present specification means that the fatty acid or triglyceride contains less than 6 carbons.

The term "medium chain fatty acid" or "medium chain triglyceride" as used in the present specification means that the fatty acid or triglyceride comprises between 6 and 12 carbons.

The term "long-chain fatty acid" or "long chain triglyceride" means that the fatty acid or triglyceride contains more than 12 carbons.

The term "medium chain triglycerides" or "MCT oil" as used in the present specification means that the fraction of coconut oil comprised only of fatty acids within which have between 6-12 carbons, including caproic acid (C6), caprylic acid (C8), capric acid (C10), and lauric acid (C12). These MCTs are liquid at room temperature, do not require a carrier molecule to be metabolized, and when used in accordance with the present invention, can readily cross both the cellular membrane as well as that of the mitochondria where it can be directly metabolized. Some of these fatty acids have other properties and provide an additional benefit(s) (for example, lauric acid has antibacterial properties, and could, e.g., be used in the acne formulation according to the invention, to inhibit p. acne bacterium).

The term "liquid skin" as used in the present specification refers to an embodiment of a base composition in an inventive formulation.

The term "vegan liquid skin" as used in the present formulation refers to an embodiment of a base composition in an inventive formulation.

The term "high oleic acid sunflower seed oil" as used in the present specification means sunflower oil comprising at minimum 80% oleic acid.

The term "sunflower seed oil" means sunflower oil comprising about 20% oleic acid.

DETAILED DESCRIPTION

Delivery System:

In one aspect, the invention is directed in part to a delivery system comprising a mixture of fatty acids. In certain embodiments, the mixture comprises emu oil. Emu oil possesses a high concentration (up to 47%) of oleic acid in addition to other naturally occurring substances which result in anti-inflammatory properties useful in the treatment of pain and other inflammatory illnesses. The composition by percentage of fatty acids from Emu shows that it is quite comparable to that of human skin (See Table 2A and Table 2B), with the exception of a slightly higher percentage of oleic acid (47%) vs 31% for human skin. This similarity in composition to human skin renders it capable of serving as a carrier for other lipid as well as aqueous ingredients. For example, in certain embodiments emu oil may be combined with a selected mixture of vegetable oils composed to mimic the fatty acid profile of human skin and sebum (hereinafter, "Liquid Skin") that can be admixed with medicinally active compounds such that they incorporate into existing skin cells or may be used as raw material for creating new cells. Similarly, it is possible to create a "Vegan Liquid Skin" by using a mixture of vegetable oils to approximate the fatty acid profile of human skin and sebum. For ease of reference, "Liquid Skin" in the present disclosure encompasses both types of mixtures.

Additionally, the integration of additional phospholipids, ceramides, cholesterol, essential and free fatty acids into existing cell membranes create distance between receptors for pain and inflammation within the cell membrane, which require proximity in order to function in signal transduction (See FIGS. 8-14). This culminates in an increased pain threshold, since it would decrease the chance of transmembrane receptors interacting to signal for pain.

Many disease states such as diabetes (PMID 23878791, PMID 30216387) and cancer (PMID 30413053, PMID 31379986) are driven by and result in imbalances of lipids and phospholipids of the cell membrane (PMID 29410529). Dietary intake of fatty acids changes the fatty acid profile of human cell membranes, which in turn affect transmembrane proteins such as mechanosensitive ion channels which change cell function (PMID 30867417). Additionally, lipid profiles in the human forebrain are closely maintained throughout the healthy adult life span but are shown to decay at advanced ages (PMID 28958038). Dietary intake of other macro and micronutrients affect the overall fatty acid profile of the cell membrane. Therefore, it is of utmost importance to take the nutritional composition of our foods, as well as our medicines, into consideration if the desire is to restore and maintain health.

Thus, in one aspect, the invention is directed in part to a mixture of various oils to mimic or restore or modulate the fatty acid profile of healthy human skin and sebum, which can be customized to deliver medicinally active compounds for the treatment of multiple diseases.

To further illustrate these concepts and to emphasize the significance of the oil blend that is identical or substantially similar or can modulate the composition of healthy human skin/oil in the treatment of diseases, and can modify it, basic cellular biology of the following information is provided.

Figure 2:
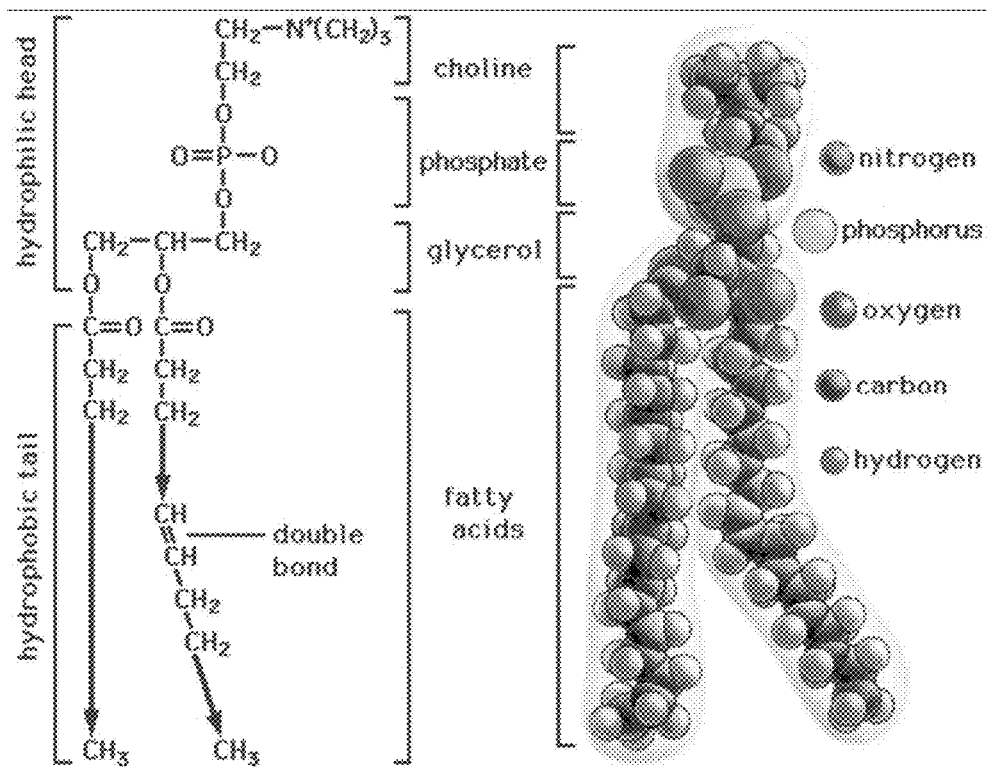
FIG. 2. Chemical Structure and 3-D Modeling of a Phospholipid. (obtained from https://classconnection.s3.amazonaws.com/624/flashcards/3771624/gif/1164999854bc1-143EF30B3E26DF055A4.gif)

Phospholipids are phosphorus-containing lipids composed of a fatty acid, a phosphate group, a glycerol, and a simple organic molecule such as choline; they are the basic building block of cell membranes, as seen in FIG. 2.

Figure 3:
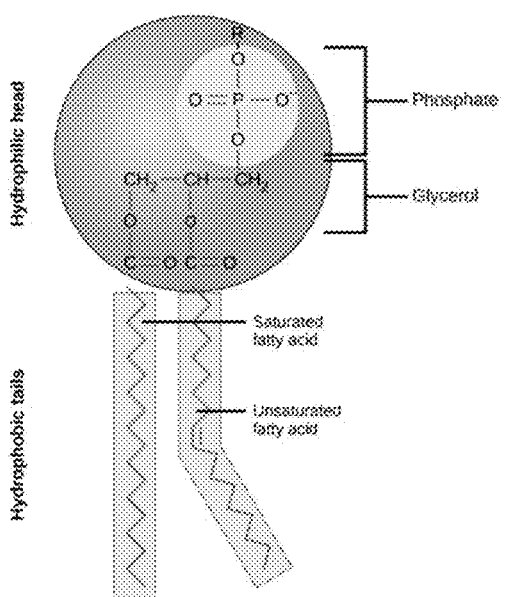
FIG. 3. Schematic Representation of a Phospholipid. (obtained from https://s3-us-west-2.amazonaws.com/courses-images/wp-content/uploads/sites/1842/2017/05/26154139/figure-05-01-03a.jpeg)
Figure 4:
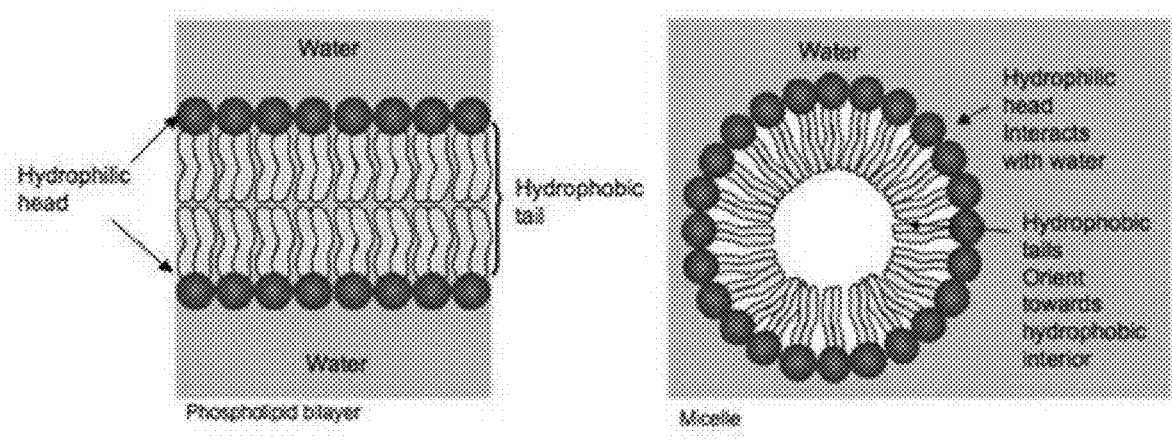
FIG. 4. Phospholipids self-assemble into bilayer structures or micelles. (obtained from https://qph.fs.quoracdn.net/main-qimg-2417fafb8e6c3b90319bc5675c5a32c3-c)
Figure 5:
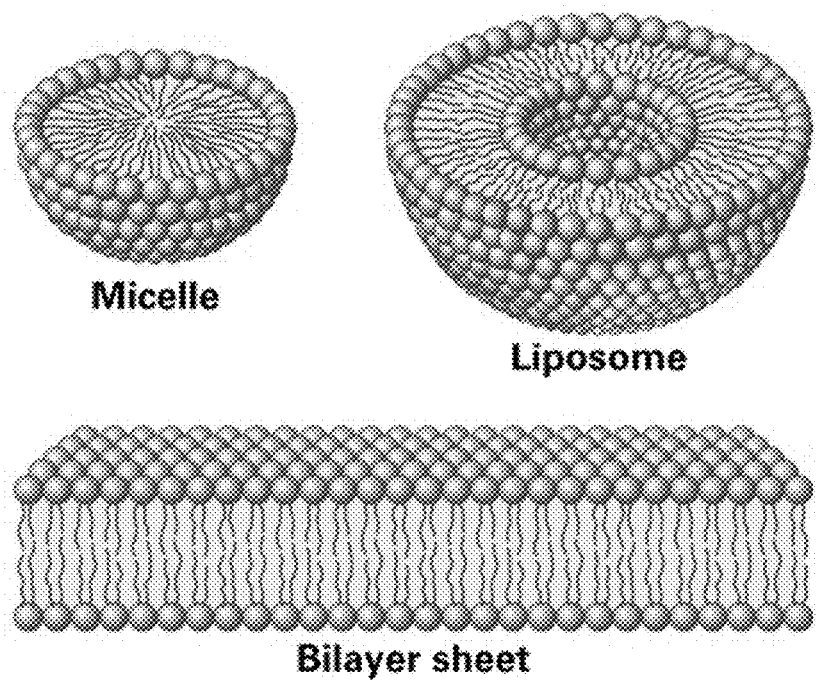
FIG. 5. Phospholipids can form micelles and liposomes (which can serve as carriers of therapeutic molecules, including transmembrane proteins) as well as bilayer sheets which form the cell membrane. (obtained from https://3.bp.blogspot.com/-8TKWDN8jY5g/UDhU0b3NbEI/AAAAAAAABR4/fkcPx9Tj0ss/s1600/F02-20.JPG)

Due to the complexity of the chemical structure, phospholipids are typically represented as a ball-like structure with two tails in most diagrams, as seen in FIG. 3.

Of note, phospholipids can self-assemble in water into organized bilayer structures or even micelles (spheres).

Figure 6:
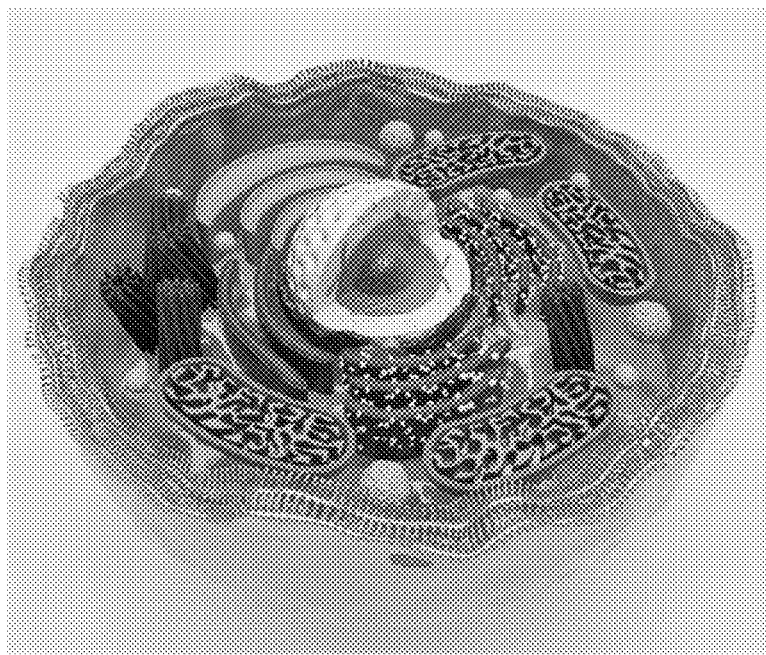
FIG. 6. 3D model of a human cell, cut in half to reveal cell contents. Note the phospholipid bilayer forming the cell surface/cell membrane (peach-color). (obtained from https://static.turbosquid.com/Preview/2014/05/19_18_04_31/human1/20cell1/20max1/202.jpgd9d481ff-258d-4a3b-8b31-fd0373c15409HD.jpg)

The cell is essentially a giant double-layered liposome (See FIG. 6), which houses many smaller organelles "mini organs" which are the machinery of the cell (akin to lifting up the hood of a car to see the parts that make up an engine) including the cell nucleus (seen in yellow in FIG. 6) which is the command center of the cell housing the deoxyribonucleic acid or DNA (think of the nucleus as the hub that directs the organelles how to function, what proteins to make, etc.). Any cell can individually activate specific DNA sequences to make proteins that cause the cell to signal to other cells. If the DNA sequences become activated out of sequence or lose their system of checks and balances, then cancer or other diseases may result. Similarly, if cells lose their function, or the healthy ability to recognize that it is damaged and fail to auto-destruct in an orderly fashion (apoptose), this also leads to disease. Thus, the cell surface is critical for how signals from outside the cell make its way into the cell nucleus to change the activity and function of the cell. A healthy cell membrane is required for signals from within the cell to be sent appropriately into the environment outside of the cell. One cell's signaling has the ability to alter the activity of other cells locally or in remote locations.

Figure 7:
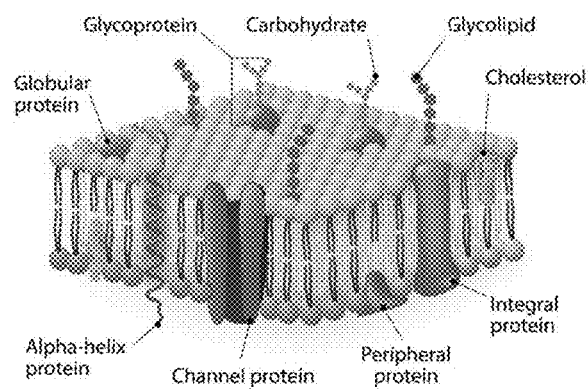
FIG. 7. Section of Human Cell Membrane Showing Transmembrane Proteins. (obtained from https://pixfeeds.com/images/21/511840/1200-86007545-cell-membrane.jpg)

If one were to snip out a small square from the surface of the human cell membrane, one would discover that there are many proteins, lipids, signaling proteins, ceramides, cholesterol, receptors and other biologically active molecules spanning the cell surface; as well as some that are only on the outer or inner leaflet of the cell membrane, each which are important in signaling for different cell pathways (such as ones for cell division, cell death, inflammation, cancer, diabetes, etc.) (FIG. 7).

Figure 8:
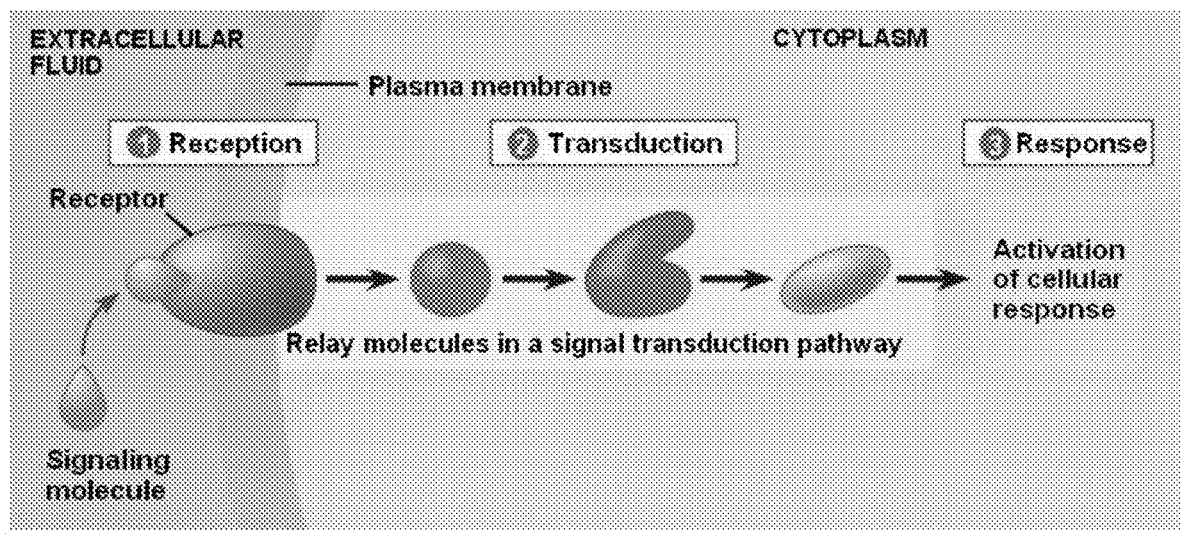
FIG. 8. Extracellular Signals Result in Intracellular Changes in Cell Behavior. (obtained from https://croteau-bio.files.wordpress.com/2011/12/cell-to-cell-communication-9-7281.jpg)

Information from outside of the cell is transmitted via reactions at the outer cell membrane leaflet, resulting in changes in membrane-embedded cell receptors that leads to changes inside the cell, resulting in gene expression and protein production within the cell (FIG. 8).

Figure 9:
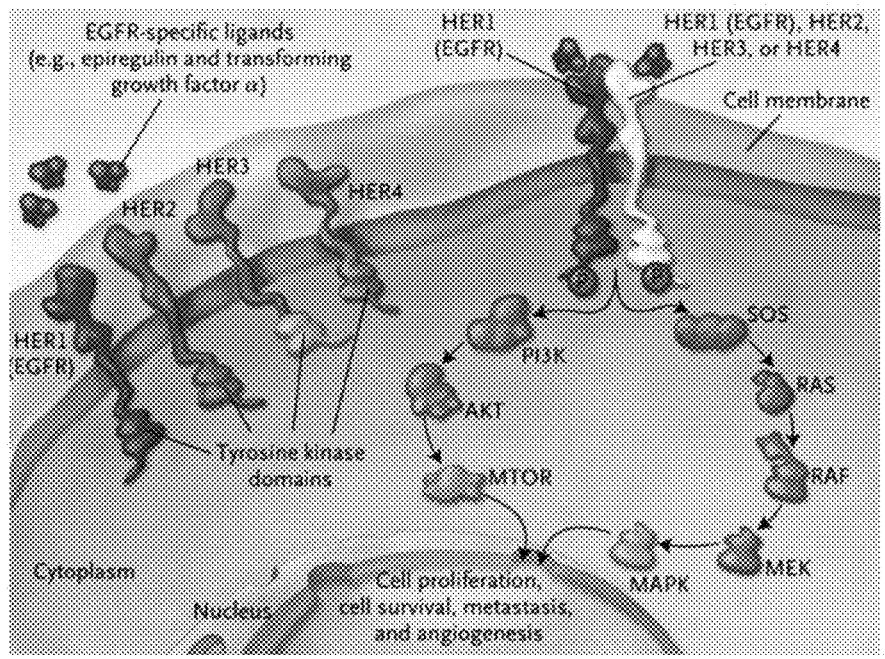
FIG. 9. Epidermal Growth Factor Receptors Heterodimerize Triggering Proliferation. (obtained from http://biochemistry.utoronto.ca/wp-content/uploads/2014/10/Cell-Signaling-Stagljar-670×504.jpg)
Figure 10:
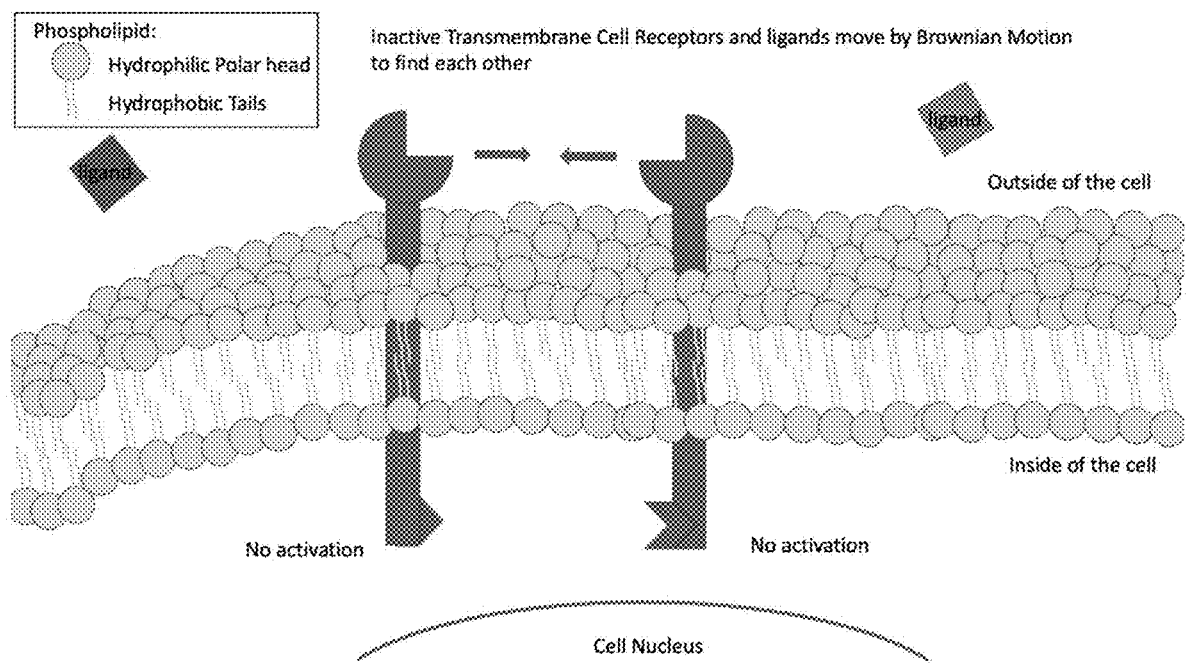
FIG. 10. Simplified Schematic of Cell Signaling with Transmembrane Receptors.
Figure 11:
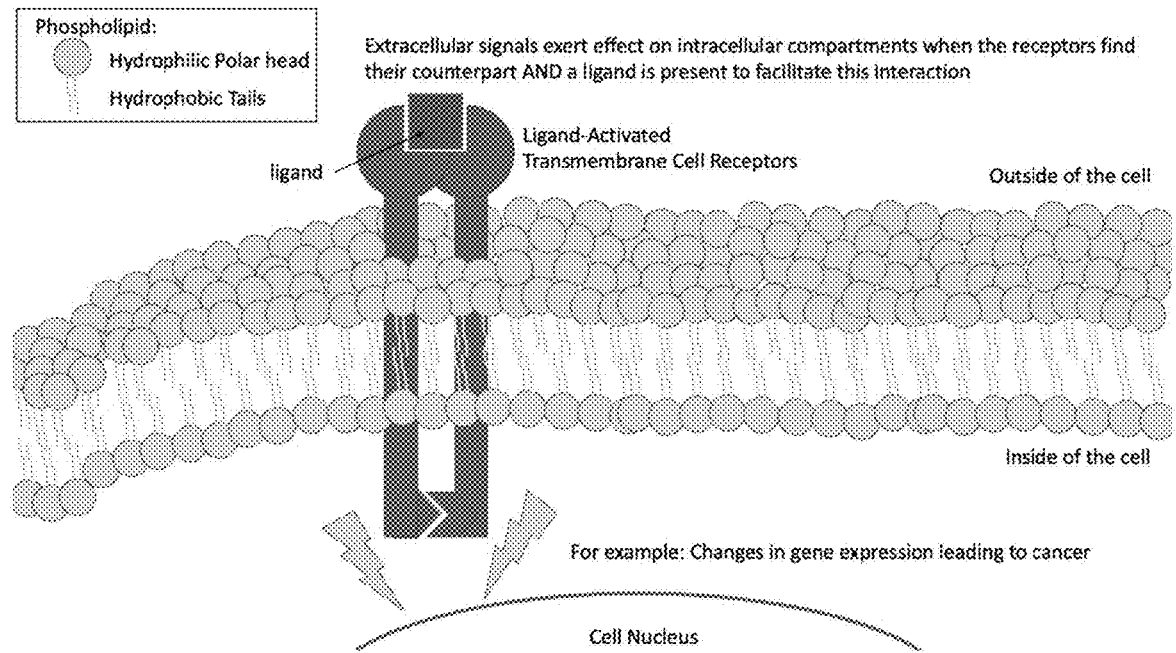
FIG. 11. A ligand (a chemical messenger from outside of the cell) binds when receptors find their counterpart, generating signals that reach into the cell to direct the cell's command center, the nucleus to act (for example, directing the cell to grow out of control).
Figure 12:
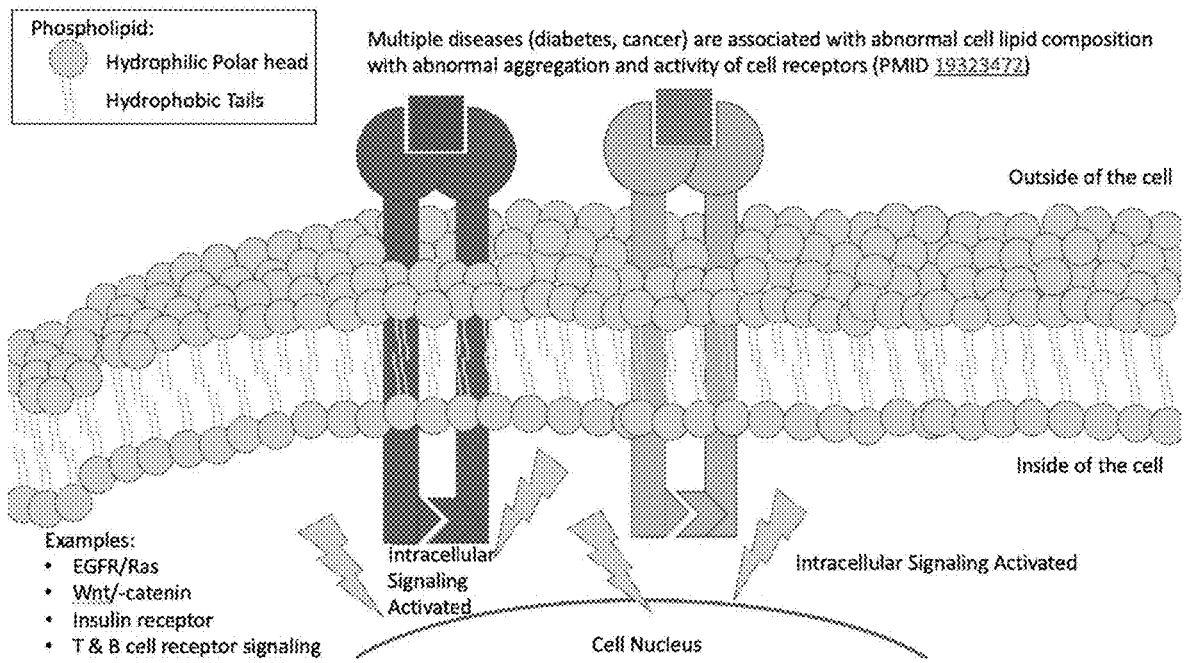
FIG. 12. Multiple chronic diseases are associated with abnormal cell lipid composition.
Figure 13:
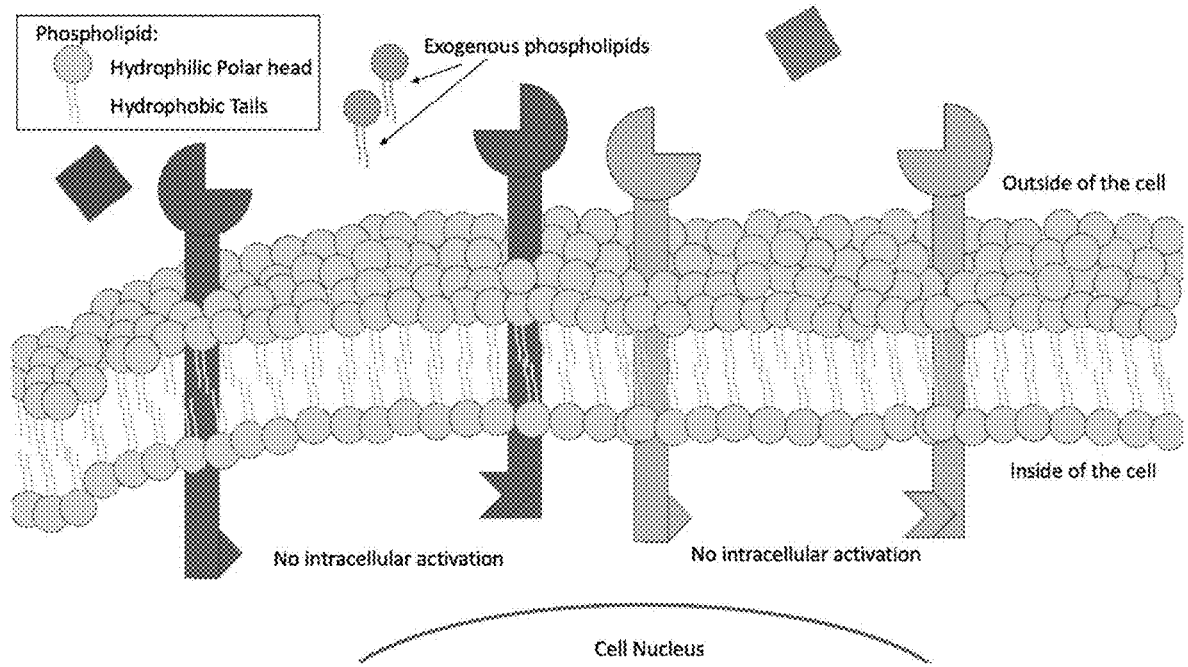
FIG. 13. Exogenously supplied phospholipids, sphingolipids, and fatty acids can incorporate into existing cell membranes, and be used to create new cells.
Figure 14:
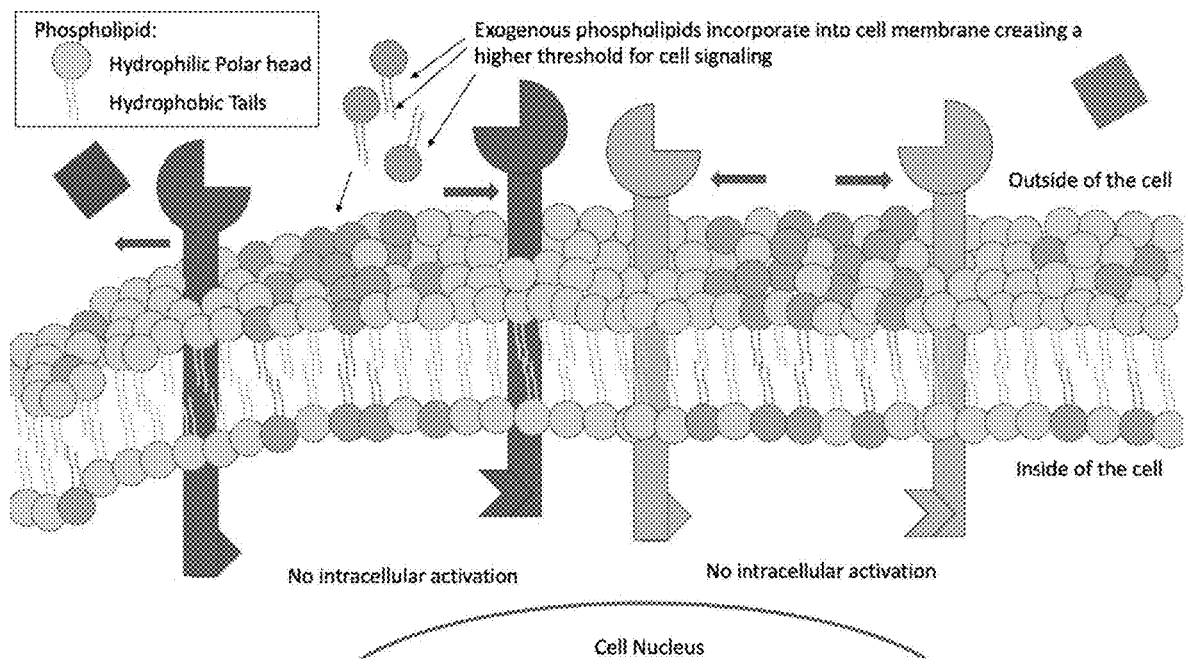
FIG. 14. Exogenously supplied phospholipids, sphingolipids, and fatty acids incorporate into cell membranes, raising the threshold required for cell signaling.

For example, this cross section of a cell shows the EGFR (Epidermal Growth Factor Receptor) embedded in the cell membrane (FIG. 9). EGFR is important in cell proliferation. Dysregulated EGFR signaling leads to unregulated cell growth, cancer, and metastases.

In FIG. 9, note that the EGFR receptors must move together closely in the cell membrane (displacing phospholipids in order to do so) in order for the extracellular signals (the EGFR-specific ligands) outside of the cell to exert their effects (delivering the "order" for the cell to start dividing) to the cell nucleus (the command center of the cell). Similar receptors exist for pain, and other biological processes in a mammal The cell membrane is the site where signals from the outside environment are interpreted and translated into directions that drive that cell's behavior. A healthy cell membrane is composed of a mixture of lipids, proteins, and sugars, (See FIG. 7) organized into regional domains (commonly called "lipid rafts") that serve to signal for multiple aspects of cell behavior such as growth, cell division, pain, cell differentiation, or cell death (PMID 31052427). Specific sub-compartments of the cell possess different lipid compositions (PMID 31052427), which when altered due to diet or genetic defects lead to alterations in cell function, metabolism, and ultimately to chronic disease such as cancer (PMID 30518103), diabetes (PMID 29462590, 28742512), Alzheimer's Disease (PMID 31379503), neuroinflammation (PMID 31862695) and altered pain processing (PMID 31862695, PMID 29459435) as just a few examples.

Fatty acids and other plant-derived compounds have an ability to insert into the human cell membrane. For example, n-3 polyunsaturated fatty acids such as eicosapentaenoic acid (EPA) and docosahexaenoic acid (DHA); as well as plant-derived polyphenolic and terpenoid phytochemicals such as curcumin (diferuloylmethane) possess the ability to span the cell membrane and disrupt cell signaling. When EPA, DHA and curcumin were used separately or together in one study, they reduced the number of atypical/precancerous stem cells in an animal model of colorectal cancer (PMID 16475686, 29860560). The proposed mechanism was the disruption of the lipid rafts (regions of the cell surface enriched in signaling proteins) necessary for transmembrane signaling.

Similarly, a possible mechanism by which "Liquid Skin" (a blend of oils to approximate the fatty acid composition of human cell membranes and sebum) may treat a medical condition (e.g., pain) is by disrupting the signaling that occurs at the cell surface by inserting into the cell membrane, decreasing the likelihood of the paired or multimeric receptors interacting with each other (See FIGS. 10-14).

Transmembrane receptors migrate along the surface of the cell in multiple directions according to Brownian Motion (a random movement of microscopic particles suspended in liquids or gases resulting from the impact of molecules of the surrounding medium), but in this case restricted to the plane of the cell membrane surface until they encounter an appropriate counterpart. Once dimerized (see the transmembrane protein-protein interaction in FIG. 11) or multimerized (formation of a multi-protein cluster) new signaling receptor docking sites may form (See FIG. 12).

Pain Mechanism Involves Multimerization of 2 or 4 Transmembrane Proteins

For example, transient receptor potential (TRP) channels are a superfamily of transmembrane ion channels that become activated in response to chemical or physical stimuli which ultimately signal for pain. These channels are made up of four subunits which are embedded on the cell surface in the cell membrane. The four individual subunits must find each other to lock into formation, resulting in a clover-leaf-like pattern before the channel can form in the cell surface to allow ions to flow through, signaling pain. If there are more phospholipids exogenously incorporated into the cell surface, then the chances that the four submits find each other and bind to form the channel decreases (See FIGS. 13-14 for an example of exogenous phospholipids decreasing changes of transmembrane protein interaction and reduced intracellular signaling). In essence, the net effect is to increase the pain threshold for a patient, as it would require a longer time for chance encounter of pain receptors to multimerize and allow for docking. Of note, unlike opioid pain medications, the mechanism targeted by this invention does not activate the mu opioid receptors, which are associated with the unwanted side effects of respiratory depression (which frequently can lead to unintentional death), as well as decreased heart rate, nausea, and constipation.

Multiple disease processes (e.g., cancer, psoriasis, eczema, etc.) show a deficit or imbalance in cell surface lipids, ceramides, and phospholipids (PMID 29410529). The derangement in fatty acid profile is due to a combination of susceptible genetics combined with a modern diet of processed foods with unhealthy excess of ω6 polyunsaturated fatty acids that predispose to inflammation, and a concomitant deficit in ω3 polyunsaturated fatty acids that result in an anti-inflammatory response when ingested (PMID 29860560). Directly restoring cell surface lipids and other cell membrane components which incorporate into cell membranes may serve to limit and prevent these disease processes by preventing abnormal cell signaling.

Figure 15:
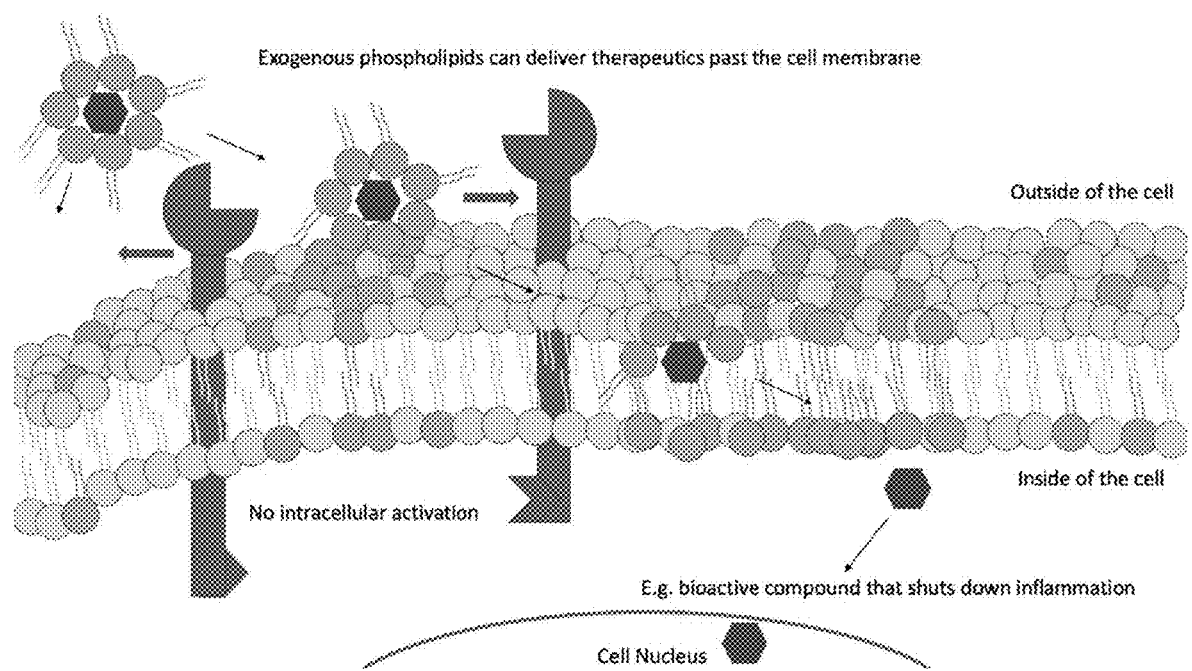
FIG. 15. Exogenously supplied phospholipids, sphingolipids, and fatty acids confer therapeutic compounds with the ability to cross the normally hydrophobic cell membranes. Once inside the cell they can direct the command center of the cell (the nucleus) to calm inflammation, to shut down cancer genes, etc.

Significantly, this could mean that patients with chronic illnesses such as diabetes, cancer, psoriasis, eczema, chronic pain, fibromyalgia (to name a few) would benefit from topical application of "Liquid Skin" and potentially by ingestion of "Liquid Skin" especially when customized for each specific disease state to deliver disease-specific therapeutics into affected tissues (See FIG. 15). Any disease involving subunit transmembrane receptors could potentially be targeted with this invention. As of 2019 there are over 4333 known transmembrane proteins (PMID 31874615) with more being discovered by Deep Learning methods (computerized protein structural modeling, PMID 33336200). Consequently, there exists an untold number of illnesses caused by dysregulation in cell membrane composition, resulting in altered protein-protein interaction and signaling. These diseases could potentially be helped by restoring a healthy fatty acid profile to the cell membrane.

Figure 16:
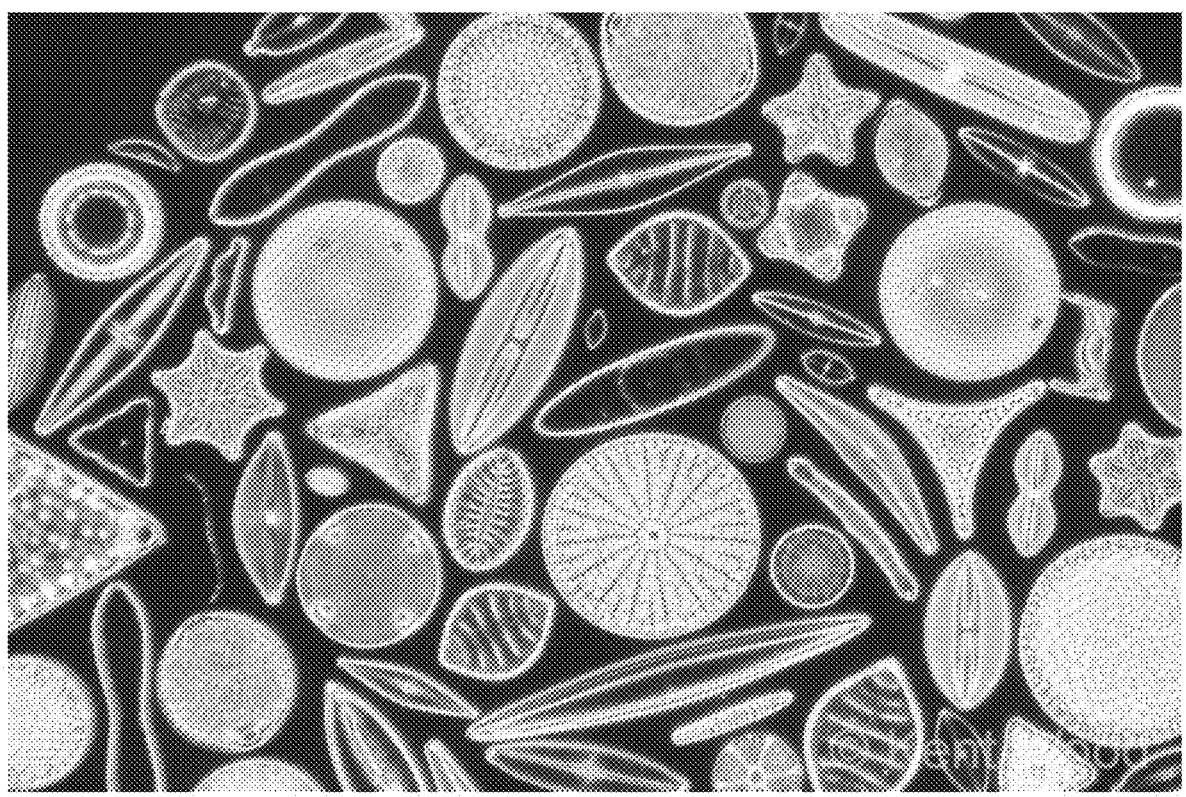
FIG. 16. Many types and shapes of diatoms. Photo Reference Credit to Kent Wood, Photographer. (obtained from http://www.illinoisscience.org/wp-content/uploads/2017/11/diatom-007-2400-copy.jpg)

Additionally, exogenous phospholipids and other lipid mixtures like Liquid Skin can be used to confer penetrability to nanoparticles such as naturally occurring biosilicates such as Food Grade Diatomaceous Earth (FGDE). FGDE are biocompatible, nontoxic porous biosilicate skeletal remains of unicellular diatom microalgae that measure between 1.9 μm to 180 μm. They have many complex shapes and surfaces (See FIG. 16) which renders them useful as micro drug delivery systems (PMID 31618958)—particularly useful in the delivery of substances with poor water solubility and low oral bioavailability such as quercetin (PMID 31496698), useful for prolonging drug delivery (PMID 316618958) and useful in the treatment of metastatic cancer (PMID 31330820), which requires the sustained ability to regain control of intracellular signaling pathways appropriated by cancer (PMID 25239399).

Figure 17:
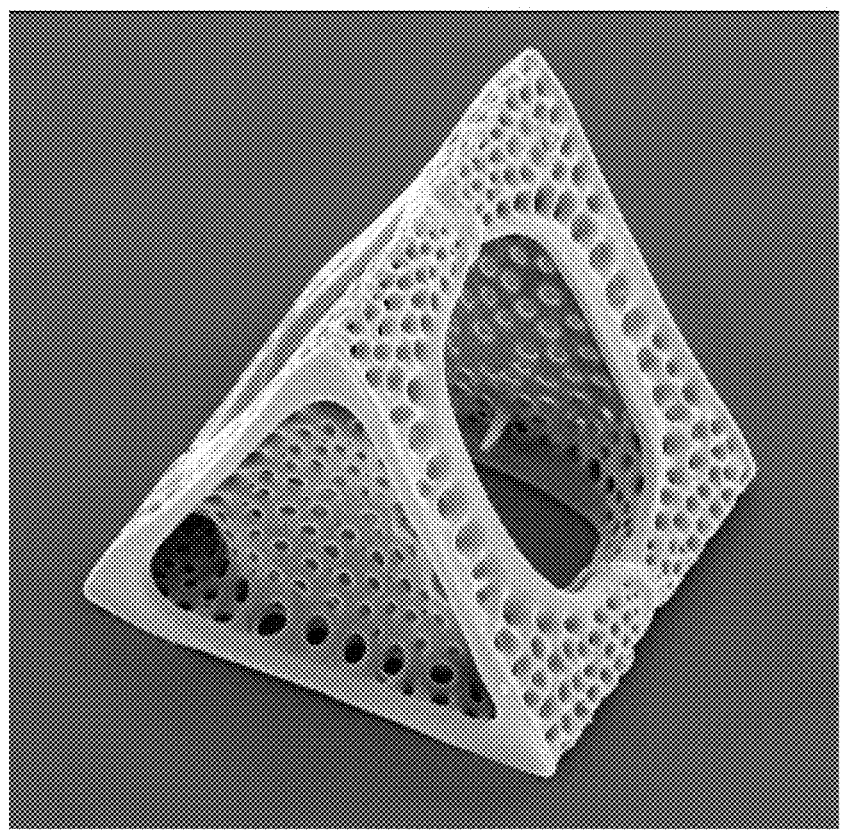
FIG. 17. Example of a diatom with intricate 3-dimensional structure and pores useful for complexing multiple compounds. Photo Reference Credit to Steve G. Schmeissner, photographer. (obtained from http://3.bp.blogspot.com/-qAQfLhi8Ty8/Ubs7sgBjXDI/AAAAAAAAAeo/ANMfoJ2FHQw/s320/26-diatom-sem-steve-gschmeissner.jpg)

FGDE is safe to consume but hazardous to work with when dry. Thus, in certain embodiments, an N95 mask must be worn to cover the nose and mouth when handling it in a well-ventilated space to prevent interstitial lung disease from silicosis. When taken orally after it has been coated, FGDE will pass through the digestive tract unchanged and does not enter the bloodstream. Diatoms do not penetrate the skin when applied to the skin as a clay paste, unless coated with substances that confer penetrative properties. The diatoms are possessed of many pores and have complex 3-dimensional architecture, ideal for loading multiple bioactive compounds (FIG. 17).

Figure 18:
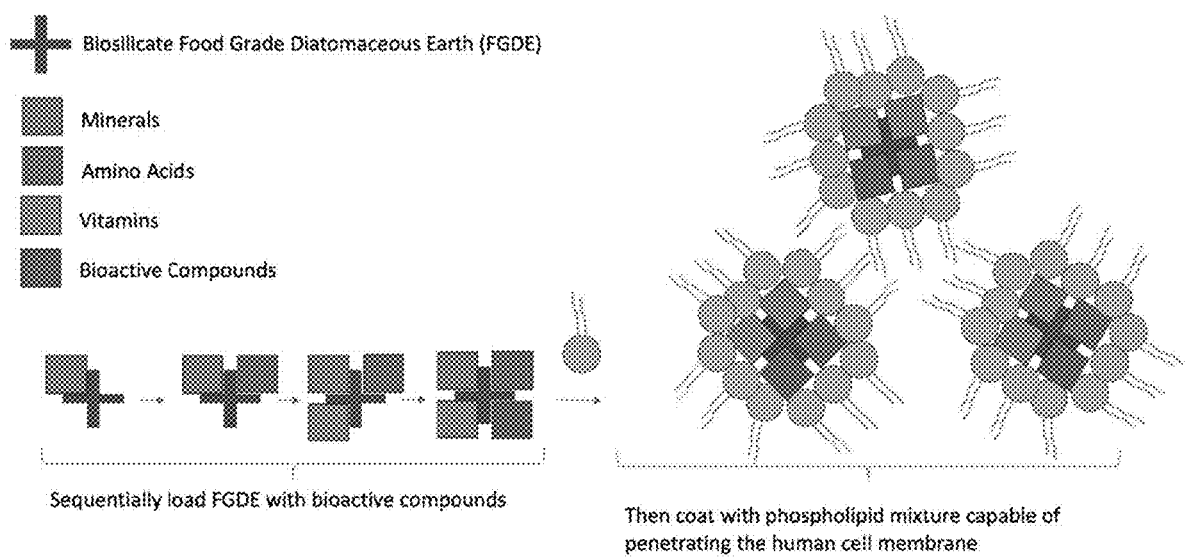
FIG. 18. Loading of diatoms with minerals, amino acids, vitamins, and bioactive compounds, then coating them with substances that confer penetrability of human skin as well as cell membranes.
Figure 19:
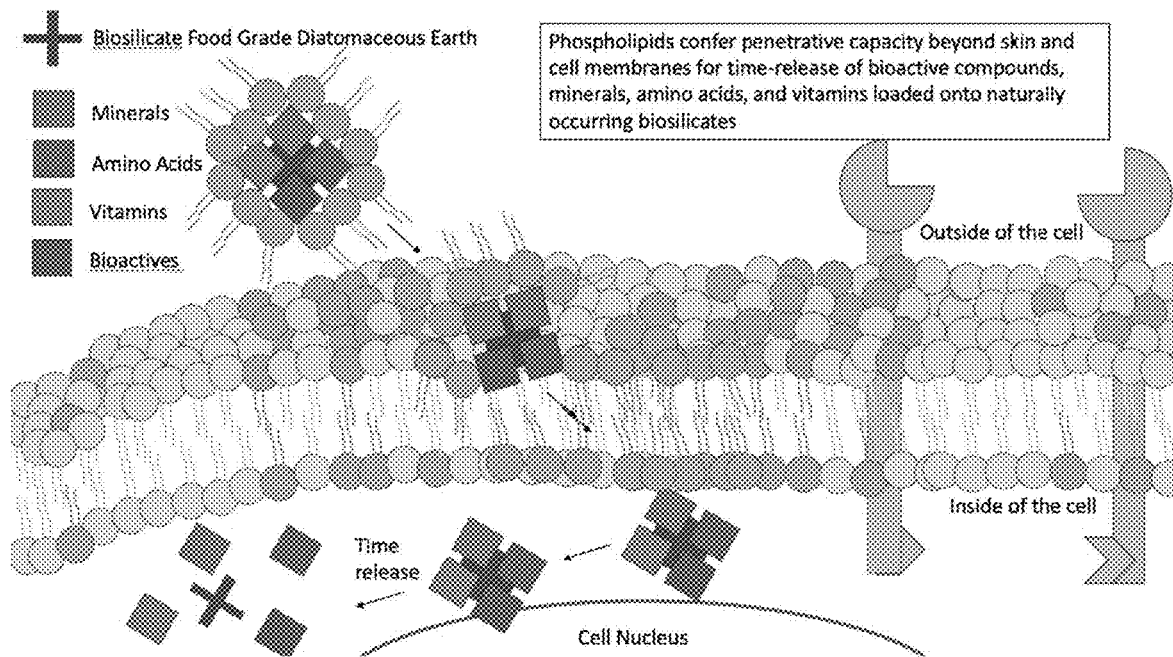
FIG. 19. Time release of therapeutic substances into the skin, as well as past the cell membrane. Delivery of these raw materials facilitate cellular and tissue repair.
Figure 23:
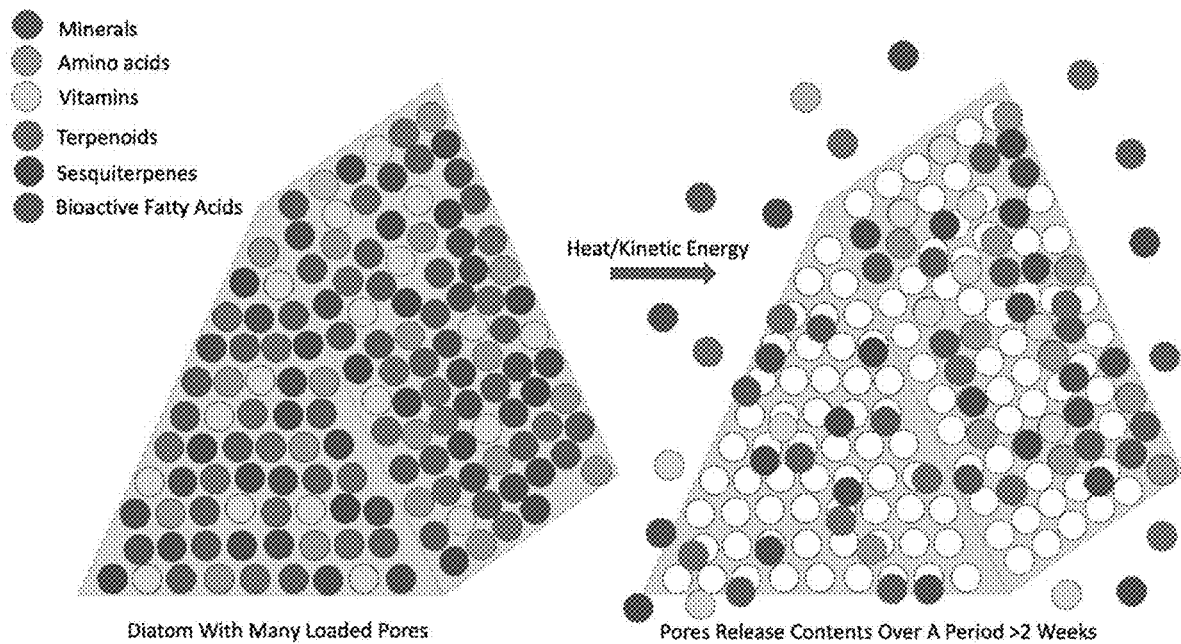
FIG. 23. Schematic of A Diatom Releasing Multiple Active Ingredients Over >2 Weeks.
Figure 24:
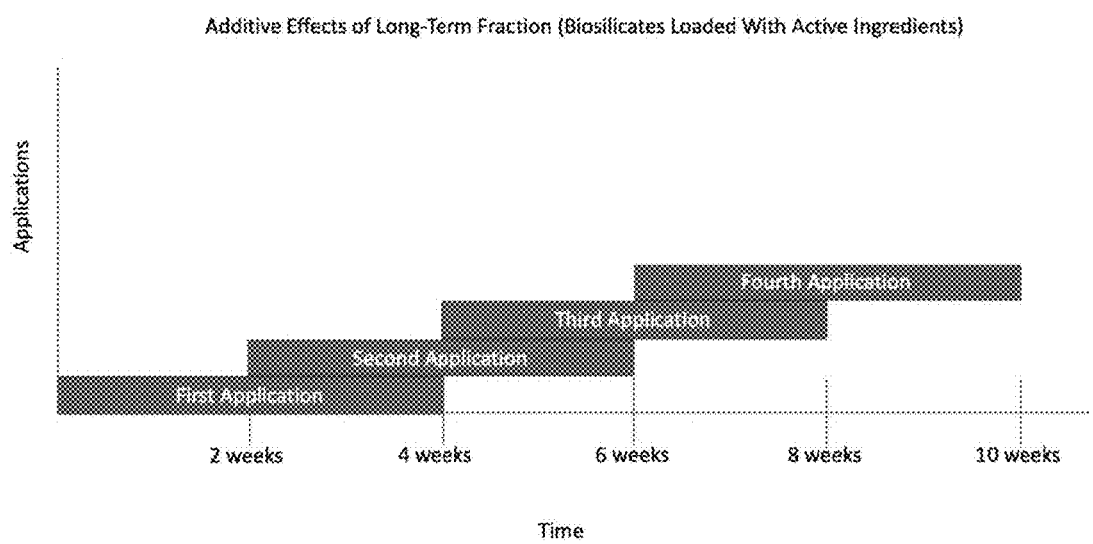
FIG. 24. Additive Effects of Long-Term Fraction (Biosilicates Loaded with Active Ingredients).

In certain embodiments, the invention is directed in part to diatoms hydrated in a dead sea saltwater solution to render the surface of the diatoms able to form bonds and to load minerals. In some of these embodiments, the hydrated diatoms are sequentially loaded with amino acids, vitamins, and other bioactive compounds (See FIGS. 18-19, and 20-22) and then coated with a mixture of oils which will confer ability to penetrate the skin and the cell membrane (FIG. 18-19). Alternatively, hydrated diatoms may be loaded with one bioactive ingredient; mixtures of these individually loaded diatoms may be combined to provide benefit in the target disease. In some of these embodiments, the hydrated, coated and loaded diatoms release the loaded compound(s) and provide a therapeutic effect, e.g., for a duration from about 5 seconds to 8, or more, weeks (See FIG. 23). In some embodiments, it takes about 2 to 4, 2 to 6 or 2 to 8 weeks or longer for the loaded components to dissociate from the nanoparticle (See FIGS. 23-24).

Thus, the invention is also directed in part to the use of natural biosilicate nanoparticles (Food Grade Diatomaceous Earth, or FGDE) as a delayed-release delivery system for multiple bioactive compounds, and then coating these loaded particles with Liquid Skin to confer the ability to penetrate the skin as well as the cell membranes for the purpose of delivering compounds that alter cell function and/or alleviate and reduce severity of one or more symptom(s) of a medical condition (See FIGS. 18-19).

It shall be noted that some of the coated nanoparticles may penetrate the skin into the intercellular space while other coated nanoparticles may penetrate past the cell membrane into the cell. Both sets of nanoparticles will slowly deliver vital nutrients such as minerals, amino acids, vitamins important for tissue regeneration and repair, coupled with bioactive compounds that facilitate healing and stem cell regeneration over, e.g., at least 2-4 weeks (See FIGS. 18-19).

It shall also be noted that in the recipe provided below that the diatoms are added in a proportion that makes them the rate-limiting component to ensure that every diatom will be coated, and that a large proportion of the preparation will be immediate-acting (e.g. an active compound surrounded by lipid mixture conferring penetration into the skin and the cell membrane, See FIG. 15).

Lastly, the lipid coating which permits tissue penetration may play an additional role: that of adding into the cell membrane surface to raise the threshold for signaling for pain (FIG. 15 and FIG. 19). With time, and with the kinetic energy provided by being placed on warm human skin, the loaded components held by reversible bonds may be released gradually for, e.g., a duration from about 1 minute to 8, or more, weeks (e.g., for at least 2-8 weeks); while the components coated with lipid coating may confer immediate action. Each application of the preparations may have an additive effect due to long duration of action (See FIGS. 23-24). Thus, for example, the goals of immediate relief from pain and inflammation are achieved, while providing long-term release of active elements required for tissue regeneration and repair over a number of weeks. With each application the patient will build more nutrients only in the area that needs restoration and healing (See FIG. 24). Side effects, if any, will be limited due to the local, non-systemic application.

Figure 20:
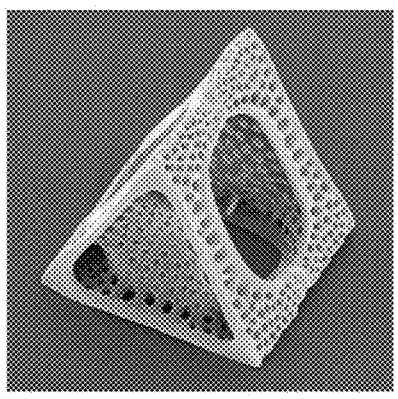
FIG. 20. Scanning Electron Microscopy Image of Unloaded Diatom with Schematic. Photo Reference Credit to Steve G. Schmeissner, photographer. (obtained from http://3.bp.blogspot.com/-qAQfLhi8Ty8/Ubs7sgBjXDI/AAAAAAAAAeo/ANMfoJ2FHQw/s320/26-diatom-sem-steve-gschmeissner.jpg)
Figure 20:
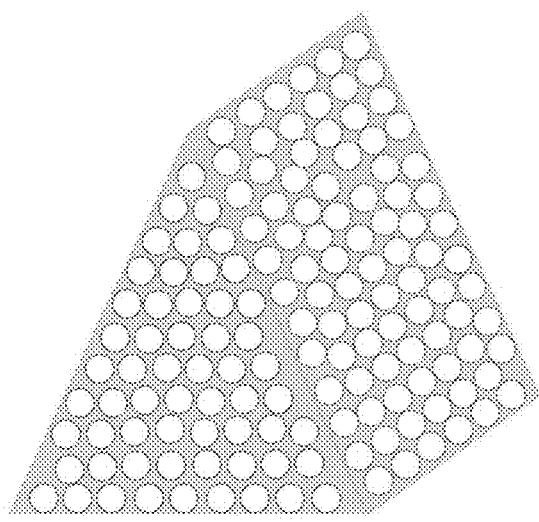
Figure 21:
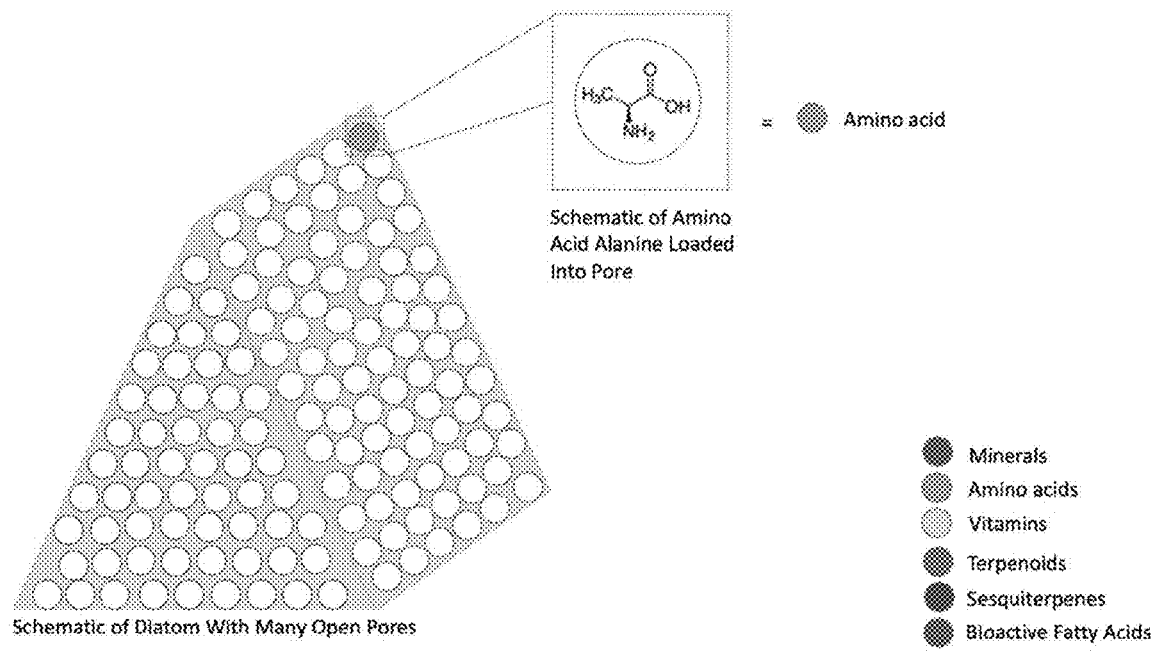
FIG. 21. Schematic of Diatom, With Many Open Pores. Demonstration of an amino acid nestling inside a pore.
Figure 22:
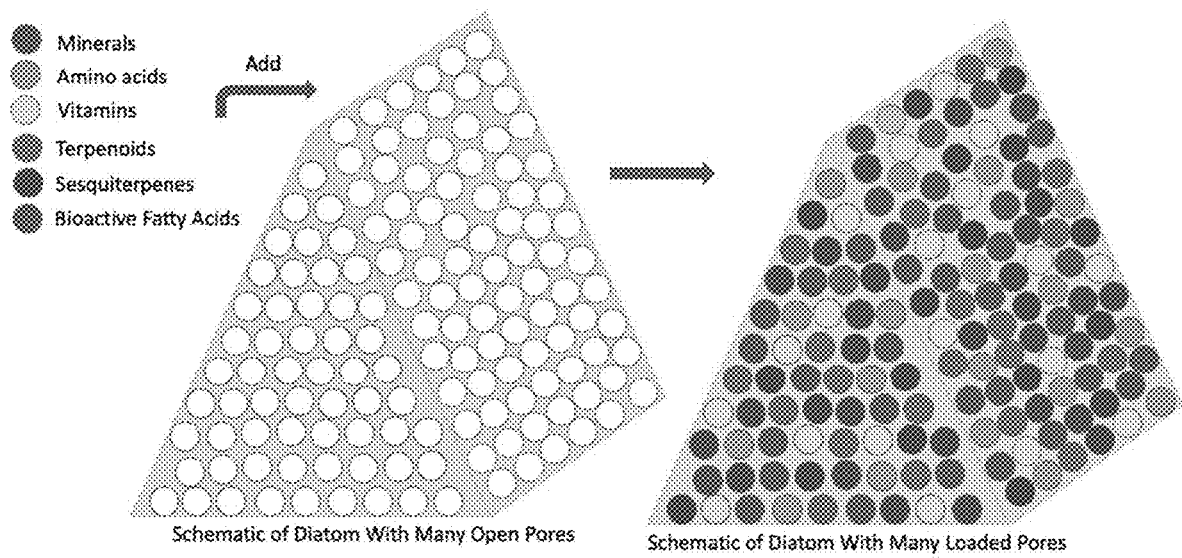
FIG. 22. Schematic of A Diatom Being Loaded with Multiple Active Ingredients.

One diatom, while tiny, is capable of loading a multitude of bioactive compounds, minerals, amino acids, and vitamins due to a multitude of open pores in which compounds may nestle into and form temporary bonds (See FIG. 20).

The percent lipid composition of pooled human sebum analyzed by thin-layer chromatography was as follows: ceramides (13%), fatty acid (47%), cholesterol (7%), cholesterol esters (2%), squalene (11%), triglycerides (3%), and wax esters (17%) (PMID 12677098) with approximately 50% as phospholipids. In certain embodiments, the preparations of the invention follow these ratios, with adjustments to components made depending on the disease being targeted.

In certain embodiments, the fatty acid composition of the invention mimics the fatty acid composition of healthy human sebum and/or subcutaneous fat. The composition of healthy human sebum and subcutaneous fat, along with composition of some oils, is provided in Table 2A and 2B.

TABLE 2A

Fatty Acid Composition of Human Sebum and Human Cells

| | Fatty Acid | Human Sebum (PMID 2940302) | Human Cell (PMID 238788791) | Human Diabetic Cell (PMID 23878791) |
|---|---|---|---|---|
| Non-Esterified Fatty Acid Fraction | Myristic Acid (C14:0) | 1.8%-2.1% | 2.48% | 2.68% |
| | Lauric Acid (C12:0) | 0.9% | 0.68% +/− 0.10 | 0.44% +/− 0.09 |
| | Palmitic Acid (C16:0) | 20.2%-75.1% | 28.50% +/− 3.15 | 24.12% +/− 1.22 |
| | Arachidonic Acid (C20:4 n-6) | * | 0.64% +/− 0.19 | 0.39% +/− 0.07 |
| Phospholipid Fraction | Palmitic Acid (C16:0) | 20.2%-75.1% | 27.84% +/− 1.82 | 25.01% +/− 1.58 |
| | Stearic Acid (C18:0) | 11.2%-13.3% | 13.15% +/− 1.24 | 14.62% +/− 1.18 |
| | Oleic Acid (C18:1 n-9) | 30.8% | 8.13% +/− 1.24 | 8.96% +/− 1.08 |
| | Linoleic Acid (C18:2 n-6) | 15.1% | 22.95% +/− 2.64 | 20.25% +/− 2.45 |
| | Linolenic Acid (C18:3 n-9) | 0.3% | 0.16% +/− 0.04 | 0.11% +/− 0.05 |
| Other Mono-Unsaturated Fatty Acid (MUFA) Fraction | Combined MUFAS | * | 11.64% +/− 1.36 | 9.45% +/− 1.32 |
| | Crotonic Acid (C4H602) | * | * | * |
| | Myristoleic Acid (C14:1 n-5) | 1.8% | * | * |
| | Palmitoleic Acid (C16:1) | 3.8%-15% | 1.41% | 1.45% |
| | Sapienic Acid (C16:1 n-10) | 3.8%-15% | * | * |

TABLE 2A-continued

Fatty Acid Composition of Human Sebum and Human Cells

| Fatty Acid | Human Sebum (PMID 2940302) | Human Cell (PMID 238788791) | Human Diabetic Cell (PMID 23878791) |
|---|---|---|---|
| Oleic Acid (C18:1 n-9) | 30.8% | 8.13% +/− 1.24 | 8.96% +/− 1.08 |
| Elaidic Acid (C18:1 n-9) | 30.8% | 8.13% +/− 1.24 | 8.96% +/− 1.08 |
| Vaccenic Acid (C18:1 n-7) | 30.8% | 8.13% +/− 1.24 | 8.96% +/− 1.08 |
| Gadoleic Acid (C20:1 n-11) | 0.9% | * | * |
| Eicosenoic Acid (C20:1 n-9) | 0.9% | * | * |
| Erucic Acid (C22:1 n-9) | 1.4% | * | * |
| Nervonic Acid (C24:1 n-9) | * | * | * |

*insignificant amounts. If no range is specified, the range is +/−3% of the listed value.

TABLE 2B

Fatty Acid Composition of Various Oils

| | Fatty Acid | Emu Oil[1] | High Oleic Sunflower Seed Oil (PMID 23610599) | Macadamia Nut Oil (PMID 23610599) | Coconut Oil[2] | Olive Oil[3] | Flaxseed Oil (PMID 31623168) |
|---|---|---|---|---|---|---|---|
| Non-Esterified Fatty Acid Fraction | Myristic Acid (C14:0) | 0.4% | 0.1% | 0.4%-1.6% | 13.1%-18.5% | 0.1%-2% | 0.08% |
| | Lauric Acid (C12:0) | * | * | 0.1% | 44%-52% | * | * |
| | Palmitic Acid (C16:0) | 20%-22% | 2%-6.5% | 7%-10% | 8%-11% | 7%-16% | 4.9% |
| | Arachidonic Acid (C20:4 n-6) | * | * | 1.5%-3% | * | * | * |
| Phospholipid Fraction | Palmitic Acid (C16:0) | 20%-22% | 2%-6.5% | 8.3% | 7.5%-10.5% | 7.5%-20% | 5% |
| | Stearic Acid (C18:0) | 9.6%-18% | 3.57%-3.94% | 3.9% | 1%-3.2% | 0.5%-5% | 4%-4.8% |
| | Oleic Acid (C18:1 n-9) | 40%-47.4% | 75%-90.7% | 54%-63% | 5%-8.2% | 55%-83% | 18.3%-20.2% |
| | Linoleic Acid (C18:2 n-6) | 15.2%-20% | 2.1%-69.8%% | 1.6% | 0%-2.6% | 2.5%-21% | 16% |
| | Linolenic Acid (C18:3 n-9) | 0.9% | 0.1% | 0.1% | * | <1% | 57% |
| Other Mono-Unsaturated Fatty Acid (MUFA) Fraction | Combined MUFAs | * | 19.2% | 81.3% | * | * | * |
| | Crotonic Acid ($C_4H_6O_2$) | * | * | * | * | * | * |
| | Myristoleic Acid (C14:1 n-5) | * | * | * | * | * | * |
| | Palmitoleic Acid (C16:1) | 3.5%-5% | 0.1% | 16%-23% | 2.5%-10.5% | 0.3%-3.5% | 0.06% |
| | Sapienic Acid (C16:1 n-10) | * | 0.1% | 16%-23% | * | * | * |

TABLE 2B-continued

Fatty Acid Composition of Various Oils

| Fatty Acid | Emu Oil[1] | High Oleic Sunflower Seed Oil (PMID 23610599) | Macadamia Nut Oil (PMID 23610599) | Coconut Oil[2] | Olive Oil[3] | Flaxseed Oil (PMID 31623168) |
|---|---|---|---|---|---|---|
| Oleic Acid (C18:1 n-9) | 40%-47.4% | 75%-90.7% | 60.9% | 5%-8% | 55%-83% | 18.3%-20.2% |
| Elaidic Acid (C18:1 n-9) | 40%-47.4% | 18.9% | 60.9% | 5%-8% | 55%-83% | 18.3%-20.2% |
| Vaccenic Acid (C18:1 n-7) | 40%-47.4% | 18.9% | 60.9% | 5%-8% | 55%-83% | * |
| Gadoleic Acid (C20:1 n-11) | * | 0.2% | 1%-3% | | * | 0.4% |
| Eicosenoic Acid (C20:1 n-9) | * | 0.2% | 1%-3% | 0%-0.5% | 0.1%-0.3% | * |
| Erucic Acid (C22:1 n-9) | * | * | * | * | * | * |
| Nervonic Acid (C24:1 n-9) | * | * | * | * | * | * |

[1] https://www.bluespringwellness.com/blogs/scientific-studies/fatty-acid-analysis-of-emu-oil
[2] https://www.chempro.in/fattyacid.htm
[3] https://www.chempro.in/fattyacid.htm
*insignificant amounts. If no range is specified, the range is +/−3% of the listed value.

In certain embodiments, the formulation comprises a mixture of oils to match a fatty acid composition of human sebum, human cell or human diabetic cell as provided in Table 2A. The oils for inclusion in the mixture may be selected from the oils listed in Table 2B, or other oils. The oils are combined in specific amounts to provide a fatty acid composition that is different from a fatty acid composition of the individual oils used and is better suited for an intended purpose.

For example, in certain embodiments, the formulation may comprise a mixture of (i) macadamia nut and coconut oil and (ii) emu oil or high oleic sunflower seed oil. The addition of macadamia nut and coconut oils to either emu oil or to high oleic sunflower seed oil results in a fatty acid composition comprising oleic acid concentration that is substantially identical to (or higher) than the concentration of oleic acid in human cell membranes, and may therefore facilitate and/or improve permeability of the formulation and its components into cell membranes and/or into the subcellular spaces and/or into the subcellular organelles of a mammalian cell. In some of these embodiments, the addition of macadamia nut and coconut oils to either emu oil (as in liquid skin) or to high oleic sunflower seed oil (as in vegan liquid skin) increases the oleic acid at minimum 5-fold that of human cell membranes, resulting in greater penetrability of admixed therapeutic substances into the cell membrane, into the subcellular space, or into the subcellular organelles of a mammalian cell (e.g., a mammalian cell). Higher concentrations of oleic acid may be required to penetrate into the subcellular organelles (e.g., to directly influence cellular metabolism) because the compounds must cross more than one set of cell membranes.

In view of the information provided herein, including Table 1, Tables 2A and 2B, one of ordinary skill in the art would be able to tailor a fatty acid composition of the mixture by using various oils and in specific amounts and provide a desired fatty acid composition and/or formulation without undue experimentation.

In certain embodiments, the composition comprises emu oil. Emu oil may comprise, in % by volume, from about 1% to about 99%, from about 2% to about 99%, from about 5% to about 98%, from about 10% to about 96%, from about 15% to about 96%, from about 20% to about 95%, from about 25% to about 95%, from about 30% to about 95%, from about 40% to about 95%, from about 45% to about 95%, from about 60% to about 95%.

In consideration of patients who may object to the animal origin of emu oil, in certain embodiments, the invention is directed in part to the use of a blend of organic vegetable oils to achieve a profile similar to that of the composition seen in healthy human skin and human subcutaneous adipose (PMID 23878791). In shall be noted that the fatty acid profile of the formulation may be optimized for specific diseases intended to be treated by the formulation and route of administration. For example, in certain embodiments the formulation may comprise organic high-oleic sunflower seed oil, with a high oleic acid content of 75-91% and used as a topical preparation useful in stimulating peripheral neuronal growth, since oleic acid is a necessary component of myelin sheath formation for neuronogenesis (the formation of new neurons in an adult human). Some of the vegetable oils that can be used in the formulation of the invention are listed in Table 2B, above, and include olive oil, due to the additional benefits of polyphenols (antioxidants), vitamins, and essential fatty acids present in this healthful oil, as well as flax seed oil and coconut oil.

Oleic acid is postulated to be the fatty acid most responsible for the superior penetration properties of emu oil, which confer its penetration properties upon substances intermixed in it. Emu oil has been demonstrated to penetrate and to carry active ingredients (PIMD 27178879, PMID 28527394) around 3 mm into human skin, by destabilizing the alpha-helix structure of keratin (PMID 28527392), interacting with fats in the skin (PMID 28527394), and promoting restructuring of skin (PMID 15837639, PMID 15567771, PMID 27069472). Application of pure emu oil alone has been found to have anti-inflammatory, and thus analgesic effects. This effect may be improved, in the present invention, upon modifying the fatty acid composition of emu oil, e.g., by blending emu oil with one or more additional oil(s) (e.g., vegetable oils) to make the profile to more closely resemble that of a human or mammalian cell membrane, a cell, an organelle, or an exosome, depending on the intended target.

In certain embodiments such as in the treatment of diseases of inflammation (such as cancer, Multiple Sclerosis, Diabetes, atherosclerosis, Coronary Artery Disease, and obesity, to name a few) emu oil in combination with one or more additional oil(s) in accordance with the present invention may be used to shift white blood cells from a pro-inflammatory M1 phenotype to an anti-inflammatory M2 phenotype.

In certain embodiments, emu oil in combination with one ore additional oil(s) may be used to upregulate stem cell markers Sox-2, Nanog, Oct4, Klf4, and c-Myc, which possess the ability to reprogram differentiated skin cells back into a stem cell-like progenitor state. This property alone may be useful in hastening recovery times for injured skin or for maintaining youthful and healthy skin. It could also be useful in the treatment of cancer (in which reprogramming of cancer stem cells into a naïve stem cell-like state could result in selective apoptosis of cancer stem cells (normal stem cells which have sustained damage and become transformed to give rise to tumor-forming cells).

In certain embodiments, every ingredient of the formulation is considered an active ingredient, as it benefits the body by addressing, e.g., specific aspects of pain.

For example, while oleic acid plays a significant role in allowing superior delivery of substances into the human body, it also decreases anger (treating one of the emotional aspects of pain) while increasing mitochondrial function (PMID 23446891), decreases intracellular oxidative stress (PMID 31802387) thus decreasing inflammation and swelling, thus decreasing pain.

Additional Applications:

There are multiple applications that can utilize the technology outlined above using pain as an example. A non-limited list of ingredients and their potential utility was listed in Table 1 above. Both Liquid Skin and Vegan Liquid Skin were designed to mimic the fatty acid profile of human skin and cell membranes in order to facilitate the transport of admixed compounds into the epidermis and into cells. High and low concentration versions of Liquid Skin and Vegan Liquid Skin were designed to generally address cell membranes severely deficient vs. moderately deficient in membrane fatty acids and other components, respectively. Food Grade Diatomaceous Earth (FGDE) loading technology as described above may be used to create loaded nanoparticles that facilitate delayed release of active compounds to injured or affected tissues. FGDE loading technology in accordance with the present invention, however, is not limited to pain but may be modified as needed for the specific disease being treated. Addition of instant-acting active compounds rounds out the design to permit immediate relief from pain, in addition to delayed release for prolonged relief from pain for example.

Potential Applications/Examples encompass the following (for each of these, a long-acting and/or a short-acting component may be formulated as described herein).

Pain Preparation:

The invention encompasses various formulation which pay be used for treatment of pain, including vegan, non-vegan, prescription strength, and over-the-counter preparations.

In certain embodiments, the present invention provides a formulation for treatment of pain. The formulation may, e.g., comprise
  i. (Any of the Pain Formulations described herein +ULDN)—in certain embodiments, this will be prescription strength which incorporates ultra-low dose naltrexone. By definition, ULDN=<1 ug daily per dose. See Table 1 for low dose naltrexone.
  ii. (Any of the Pain Formulations described herein)—in certain embodiments this will be available over the counter without ultra-low dose naltrexone The formulations may be used for different types of pain, including, for example, osteoarthritic pain, pain from rheumatoid arthritis, neuropathic pain, superficial pain, muscle aches, headaches, etc.

In certain embodiments, the formulation may be used to treat superficial muscular pain and tension by an application of the formulation to an affected area.

In certain embodiments, the formulation may be used to treat deep muscle, joint or ligament pain and tension by an application of the formulation to an affective area. The application of the formulation may be preceded and/or accompanied and/or followed by an exposure to a Red/Near Infrared Lamp. The exposure may, e.g., be from 600 nm to 1100 nm, or from 600 nm to 2500 nm. Exposure to light within this range of wavelengths may stimulate stem cells, improve metabolism by activating chromophores within the cell, stimulate increases in electron transport, in mitochondrial membrane potential and ATP production, in dilation of blood vessels >400% to facilitate influx of immune cells, all which improve cell survival, increase proliferation and migration of stem cells, leading to expedited wound healing, decreased pain, decreased oxidative stress and inflammation (PMID 28748217). Use of a Red/Near Infrared Lamp from approximately 10 inches away from target tissues for approximately 30 minutes or longer, as tolerated, will further augment the effect of a formulation which contains Liquid Skin by increasing absorption and bioactivity via the mechanisms outlined above (PMID 28748217).

In certain embodiments, the invention provides a massage oil comprising a diluted version of any of the pain formulations listed above. In some of the embodiments, the concentration of the diluted formulation is from about 5% to about 90% of the pain formulation listed above (e.g., 10% of any of the pain formulations listed above (e.g., the formulations described above for infants)). In certain embodiments, the massage oil may be used during lymphatic drainage and/or acupressure massages.

In certain embodiments, the formulation may further comprise palmitoylethanolamide (5%-30% by volume) with alpha lipoic acid (0.05%-15% by volume) as these both synergize with myrrh (0.0005%-1% by volume) for analgesia (PMID 30696240). In some embodiments, a natural source of palmitoylethanolamide and alpha lipoic acid may be used.

Neuropathy Preparations

In certain embodiments, the invention provides a formulation for treating neuropathy as described above. The formulation comprises the basic composition and one or more additional ingredients as described above.

Hair Loss Preparation

In certain embodiments, the invention provides a formulation for treating hair loss as described above. The formulation comprises the basic composition and one or more additional ingredients as described above. This may be applied to the scalp, with effects potentiated by application of near infrared light from approximately 10 inches away from the scalp, for approximately 30 minutes or longer, as tolerated.

Scalp Mask

In certain embodiments, the invention provides a mask formulation for treating hair loss as described above. The formulation comprises the basic composition and one or more additional ingredients as described above. This may be applied to the scalp, with effects potentiated by application of near infrared light from approximately 10 inches away from the scalp, for approximately 30 minutes or longer, as tolerated.

Shampoo

In certain embodiments, the invention provides a shampoo formulation for treating hair loss as described above. The formulation comprises the basic composition and one or more additional ingredients as described above. The shampoo can also be used as a hair mask—lathering up but then allowing it sit on the scalp to let the long-acting fraction soak into the scalp.

Scalp Serum:

In certain embodiments, the invention provides a scalp serum for treating hair loss as described above, which may be applied directly to the scalp, and further augmented by application of a near infrared light from approximately 10 inches away from the scalp, for approximately 30 minutes or longer, as tolerated. In certain embodiments, after the serum is applied, the hair could be washed with a shampoo, e.g., in accordance with the invention, and treated with a conditioner, e.g., in accordance with the invention.

Beauty Preparation:

In certain embodiments, the invention provides a formulation for improving skin texture, health, and cellular regeneration as described above. The formulation comprises the basic composition and one or more additional ingredients as described above.

Anti-Aging Cosmetic Moisturizing Creams

In certain embodiments, the invention provides a formulation for moisturizing the skin, and with ingredients to improving skin texture, health and cellular regeneration as described above. The formulation comprises the basic composition and one or more additional ingredients as described above.

Wrinkle Serum

In certain embodiments, the invention provides a formulation for moisturizing the skin, and with ingredients to improving skin texture, health and cellular regeneration as described above. The formulation comprises the basic composition and one or more additional ingredients as described above.

Toner

In certain embodiments, the invention provides a formulation for moisturizing the skin, and with ingredients to improving skin texture, health and cellular regeneration as described above. The formulation comprises the basic composition and one or more additional ingredients as described above. The formulation may be diluted 10% in Rosewater and sprayed onto the face as a toner.

Face Wash

In certain embodiments, the invention provides a formulation for moisturizing the skin, and with ingredients to improving skin texture, health and cellular regeneration as described above. The formulation comprises the basic composition and one or more additional ingredients as described above. The formulation may be diluted 10% and include plant-based surfactants.

Age Spot Fading cream

In certain embodiments, the invention provides a formulation for fading hyperpigmented spots as described above. The formulation comprises the basic composition and one or more additional ingredients as described above.

Face/Neck Serum

In certain embodiments, the invention provides a formulation for moisturizing the skin, and with ingredients to improving skin texture, health and cellular regeneration as described above. The formulation comprises the basic composition and one or more additional ingredients as described above. The formulation may be diluted to 20% in sea kelp bioferment and used as a night serum.

Mask

In certain embodiments, the invention provides a formulation for providing a higher concentration of ingredients in a higher concentration of FDGE to allow extended release of ingredients for improving skin texture, health and cellular regeneration as described above. The formulation comprises the basic composition and one or more additional ingredients as described above. This mask can be applied to the face, body, or scalp, with or without heat and may be rinsed off after absorption for about 20-30 minutes.

Bath Mud

A bath mud formulation is the same as the mask formulation. A thin coat of the formulation may be applied over exfoliated skin of the body and face and allowed to dry in a hot sauna or with heater in the bathroom. After mud has entirely dried the formulation is rinsed off, and, in certain embodiments, may reveal rejuvenated skin.

Burns/Wound Healing

In certain embodiments, the invention provides a formulation for locally providing nutrients important for regeneration of burned or wounded skin when applied to intact skin adjacent to injured or burned skin as described above. The formulation comprises the basic composition and one or more additional ingredients as described above. These formulations may be used in conjunction with exosomes and medical honey to facilitate regeneration and to prevent infection. The burn/wound formulation may be loaded onto porous bandages to be placed on intact skin surrounding a wound area but for safety precautions will not be applied directly to the wounded skin.

Acne Preparation

In certain embodiments, the invention provides a formulation for preventing and treating acne. The formulation comprises the basic composition and one or more additional ingredients as described above. These formulations may include ingredients which suppress p. acne without inducing antibiotic resistance, as described above.

Rash Preparation

In certain embodiments, the invention provides a formulation for treating rashes, including eczema, psoriasis, and nonspecific dermatitis or skin eruptions as described above. The formulation comprises the basic composition and one or more additional ingredients as described above.

Allergy/Itch Preparation

In certain embodiments, the invention provides a formulation for reducing IL-4 mediated mast cell degranulation thus reducing itchiness and allergic response associated with rashes, including eczema, psoriasis, nonspecific pruritus, and urticaria as described above. The formulation comprises the basic composition and one or more additional ingredients as described above.

PMS Preparation

In certain embodiments, the invention provides a formulation for treating pain and increased muscle tension at rest as described above. The formulation comprises the basic composition and one or more additional ingredients as described above. The formulation may be applied to the lower abdomen for the treatment of premenstrual syndrome (PMS), for example.

Galactagogue Preparation

In certain embodiments, the invention provides a formulation for stimulating milk production as described above. The formulation comprises the basic composition and one or more additional ingredients as described above.

Joint Pain Preparation

In certain embodiments, the invention provides a formulation for treating pain as described above. The formulation comprises the basic composition and one or more additional ingredients as described above. The formulation may be used with near infrared light 5-15 minutes per joint as described above.

Antimicrobial Preparation

In certain embodiments, the invention provides a formulation for preventing and treating skin infections as described above. The formulation comprises the basic composition and one or more additional ingredients as described above.

Dental/Gum Preparation/Oil for Floss

In certain embodiments, the invention provides a formulation for preventing and treating infections as described above. The formulation comprises the basic composition and one or more additional ingredients as described above. Several drops of this formulation may be applied to ribbon floss prior to flossing to prevent and treat gingivitis.

Needle-Free Vaccines and Medications

In certain embodiments, the invention provides a formulation for improving transdermal penetration of other substances as described above. The formulation comprises the basic composition and one or more additional ingredients as described above. In certain embodiments, a half-bubble sticker filled with Liquid Skin plus a vaccine or medication (e.g., insulin) may be adhered onto skin until absorbed.

Self-Tan Preparation

In certain embodiments, the invention provides a formulation for improving transdermal penetration of other substances as described above. The formulation comprises the basic composition and one or more additional ingredients as described above. In certain embodiments, the formula may form 25% of the final concentration, with concentrated black tea and henna forming 75% of the final concentration. This pigmenting solution may be applied evenly to exfoliated skin and allowed to set for 2 hours to provide the appearance of tanned skin, without the associated skin damage caused by ultraviolet radiation.

Sunblock Preparation

In certain embodiments, the invention provides a formulation for improving transdermal penetration of other substances as described above. The formulation comprises the basic composition and one or more additional ingredients as described above. In certain embodiments, the formula may form from about 25% to about 30% of the final volume, with carrot seed oil (SPF 35-40) forming from about 25% to about 30% of the final concentration, with red raspberry seed oil (SPF 25-50) forming from about 25% to about 30% of the final concentration for immediate acting sunscreen properties. In certain embodiments, the addition of FGDE diatoms loaded with carrot seed and red raspberry seed oils (from about 1% to about 20% by volume of the final volume) may be considered for a longer-lasting time-released natural sunblock effect.

Henna Preparation

In certain embodiments, the invention provides a formulation for improving transdermal penetration and retention of other substances as described above. The formulation comprises the basic composition and one or more additional ingredients as described above. In certain embodiments, the basic composition may comprise from about 25% to about 30% of the final volume, with henna forming from about 70% to about 75% to lead to longer-lasting designs. Alternatively, the formulation may be applied to the skin and allowed to absorb for a few minutes prior to applying henna designs.

Tattoo Moisturizer

In certain embodiments, the invention provides a formulation for moisturizing the skin, and with ingredients to improving wound healing, skin texture, health and cellular regeneration as described above. The formulation comprises the basic composition and one or more additional ingredients as described above. This formulation may be applied to intact skin surrounding a newly placed tattoo to deeply moisturize and to optimize tattoo integrity and healing while minimizing scarring.

Keloid and Scar Preparation

In certain embodiments, the invention provides a formulation for improving wound healing, skin texture, health and cellular regeneration as described above. The formulation comprises the basic composition and one or more additional ingredients as described above. Application of this formulation may result in improvement in the appearance of scars.

Ulcerative Colitis/Inflammatory Bowel Disease/Irritable Bowel Syndrome/Celiac Disease Preparation In certain embodiments, the invention provides a formulation for improving healing of the injured mucosa of the gastrointestinal tract when taken internally, as described above. The formulation comprises the basic composition and one or more additional ingredients as described above. Capsules with different dissolving coefficients may be used to target the proximal, intermediate, and distal regions of the gastrointestinal tract.

Restless Legs and Cramp Preparation

In certain embodiments, the invention provides a formulation for providing bioactive compounds required for muscle relaxation when applied topically, as described above. The formulation comprises the basic composition and one or more additional ingredients as described above.

Diabetes/Hyperlipidemia/Obesity/Hypertriglyceridemia/Metabolic Syndrome Formula

In certain embodiments, the invention provides a formulation for improving insulin resistance, hyperlipidemia, hyperglycemia and hypertriglyceridemia when taken internally, as described above. The formulation comprises the basic composition and one or more additional ingredients as described above.

Diabetes/Hyperlipidemia/Obesity/Hypertriglyceridemia/Metabolic Syndrome/Insulin Resistance/Abnormal Sleep Debt/Osteopenia/Osteoporosis/Anemia of Chronic Disease Formula 2

In certain embodiments, the invention provides a formulation for improving insulin resistance, hyperlipidemia, hyperglycemia, hypertriglyceridemia, obesity, metabolic syndrome, abnormal sleep debt, osteopenia, osteoporosis and anemia of chronic disease when taken internally, as described above. The formulation comprises the basic composition and one or more additional ingredients as described above Abnormal Sleep Debt Formula 1

In certain embodiments, the invention provides a formulation for reducing abnormal sleep debt when taken internally, as described above. The formulation comprises the basic composition and one or more additional ingredients as described above Osteopenia/Osteoporosis/Anemia of Chronic Disease Formula 1

In certain embodiments, the invention provides a formulation for improving insulin resistance, hyperlipidemia, hyperglycemia, hypertriglyceridemia, obesity, metabolic syndrome, abnormal sleep debt, osteopenia, osteoporosis and anemia of chronic disease when taken internally, as described above. The formulation comprises the basic composition and one or more additional ingredients as described above Leukoplakia/Tongue Lesion/Oral and Vaginal Mucosa Healing Formulation In certain embodiments, the invention provides a formulation for improving lesions of the mucosa when applied topically, as described above. The formulation comprises the basic composition and one or more additional ingredients as described above.

Pitting Edema/Heavy Lymph Load

In certain embodiments, the invention provides a formulation for improving pitting edema and/or lymphedema when applied topically, as described above.

It shall be noted that each preparation used herein is referred to by systematic name, as trade names will be determined later. For example, for the treatment of Pain, the formulation is designated Pain Preparation 1.0 to signify preparation for pain, version 1.0, 2.0 for the next iteration, etc.

Example 1

Pain Preparation 1.0 (PP1)

PP1 was 5 ml of German chamomile essential oil in 4 fluid ounces of emu oil, mixed thoroughly. German chamomile essential oil (over Roman chamomile essential oil) was investigated because the inventor recognized that it could exert its effects on the Central Nervous System (CNS) despite it being applied distally. Emu oil was used for its ability to penetrate deeply and deliver ingredients admixed therein.

The formulation was tested and found to be effective for relieving abnormal muscle tension when other topical preparations purchased on the market failed.

The formulation was also found to be effective for relieving insomnia, which is believed to be due to the formulation's mild anxiolytic properties.

The formulation was also found to be effective in a patient with chronic neck pain from multiple neck injuries who had no history of neck surgery. The patient used PP1, the near infrared (NIR) light, along with other natural methods of pain management, and found it effective for the treatment of pain.

PP1 was also tried in a patient with intractable neck pain status post multiple neck surgeries who was looking for a natural topical solution for the pain. The patient had tried opiate pain pills and patches to no avail. The patient applied PP1 to her neck and found it effective for pain relief shortly after application.

PP1 could be used alone, or in conjunction with a near-infrared (NIR) lamp (from approximately 600 nm to 2500 nm. The NIR lamp may be used, e.g., to dilate blood vessels and increase local blood flow to >400% within seconds of applying the light, ~10 inches from the skin, for 5-60 minutes at a time or as tolerated (PMID 28935419).

PP1 had a distinctive odor. A cold-pressed orange essential oil, as well as peppermint essential oil, was initially added to improve the odor of PP1; and the use of perfumed anointing oil was contemplated for inclusion in the formulation. This led to the design of Preparation 2.0.

Example 2

Pain Preparation 2.0 (PP2)

PP2 versions comprised 20-30 drops (1-1.5 ml) of German chamomile oil, with the addition of 40 drops (2 ml) premium cold-pressed orange essential oil, 10 drops (0.5 ml) peppermint essential oil, and 10 drops (0.5 ml) Bridal Garden Jerusalem Anointing Oil by www.thenewjerusalem.co. The remaining balance was Emu oil up to a final volume of 1 fluid ounce. 12 bottles of PP2 were distributed to 12 subjects who agreed that the new formulation smelled pleasant and was more effective than the original.

PP2 was applied in the evening on two patients with neck stiffness who reported relief from stiffness and pain shortly thereafter. Patients remained at 0/10 pain the next morning and both stated they slept well, felt relaxed, and that their neck muscles were no longer stiff.

PP2 was also tried in a patient suffering from severe eczema for the past 6 years. His hands were covered with patches of cracked, dry, thickened, bleeding skin. After he applied PP2 to his hands (3 applications over 48 hours) he noted improvement as the lesioned skin became noticeably softer, thinner, and with a more normal texture. The pinpoint bleeding had closed. He noted additional improvement when PP2 was applied to damp hands with an occlusive barrier cream applied on top overnight. His previously lesioned skin felt almost smooth after the third application.

Example 3

Pain Preparation 3.0 (PP3)

PP3 was designed with an immediate-acting portion for instant pain relief, as well as a long-acting portion that would continually release bioactive substances such as the terpenoids, sesquiterpenes and flavonoids found in Moroccan Chamomile Oil, German Chamomile Oil, Roman Chamomile Oil; as well as minerals, amino acids, and vitamins required for tissue repair. The long-acting portion may provide effects for at least 2-8 weeks (PMID 31618958).

Naturally occurring micron-sized biosilicates such as Food Grade Diatomaceous Earth (FGDE) were contemplated for use in PP3. These biosilicates are already preformed, do not require toxic chemicals to create, are chemically inert, are safely tolerated by living organisms for ingestion or topical application, have a large surface area for loading of pharmaceutically active compounds, thermostability, and most importantly safely serve as inert carriers of pharmaceutically active compounds without interfering with their native function (PMID 31618958).

Additionally, loading these biosilicates with pharmaceutically active compounds simply requires incubating the hydrated diatoms/biosilicates with compounds of interest in sequential order to allow for attachment of the pharmaceutically active substances onto the biosilicates (PMID 31618958). In other embodiments, hydrated biosilicates may be loaded with only one active compound; and a mixture of such singly loaded biosilicates may be considered depending on desired effect in target tissues.

It was contemplated that sequential incubations with other substances will extend the complexes with each new additional substance. When the single complex or the multiply loaded complex is admixed with Liquid Skin to facilitate absorption into the skin, with time and body heat the temporary bonds holding the pharmaceutically active substances together will break and release the individual active components into the tissue in need of repair. This process is time-released as it requires time (and increased kinetic/thermal energy; supplied by contact with a human body for example) for the bonds to break. This delayed release of active compounds will confer PP3 with a longer duration of effectiveness.

The design was to first create the long-acting portion, and then add the immediate-acting portion (including the anxiolytic), as these should be readily available for immediate effectiveness. An objective is to have immediate pain relief, as well as extended release of minerals, amino acids, vitamins, and bioactive plant flavonoids, terpenoids, sesquiterpenes, etc. which promote tissue regeneration and repair into the specific tissues that need it. Thus, with each application, the tissues will be directly supplied with raw materials required for tissue formation and repair, facilitating healing and recovery.

PP3 could be made in multiple strengths (See Table 3 for sample recipes).

TABLE 3

| | PP3 Formulation Sample Recipes by Patient Population | | | | |
|---|---|---|---|---|---|
| | Function | Extra Strength* | Adult | Elderly or Child | Infant <1 yr |
| Loaded Biosilicates (Long-Acting Fraction) | Time release delivery of minerals, amino acids, vitamins & bio-actives for long-acting relief of pain and anxiety, delivery of substances required for tissue repair. | 3 ml | 2 ml | 1 ml | 0.5 ml |
| German Chamomile | Immediate-acting relief of pain, anxiety, abnormal muscle tension, local allergy, itch, inflammation, rashes. Topical antimicrobial. | 0.15 ml | 0.05 ml | 0.025 ml | 0.0125 ml |
| Moroccan Chamomile | | 0.30 ml | 0.10 ml | 0.05 ml | 0.025 ml |
| Roman Chamomile | | 0.15 ml | 0.05 ml | 0.025 ml | 0.0125 ml |
| Jasmine | Immediate-acting relief of anxiety, insomnia and abnormal muscle tension | 0.15 ml | 0.05 ml | 0.025 ml | 0.0125 ml |
| Lemongrass | Immediate-acting relief of pain, depression, fever, abnormal muscle tension & spasms, insomnia. Topical antimicrobial. Anticancer activity. | 0.15 ml | 0.05 ml | 0.025 ml | 0.0125 ml |
| Emu oil | Penetrates human skin surface & confers this ability on admixed substances. Decreased in myristic acid, palmitoleic acid, and lauric acid as compared to human sebum. | 11.10 ml | 12.70 ml | 13.85 ml | 14.43 ml |
| | Total Volume: | 15 ml | 15 ml | 15 ml | 15 ml |
| | Immediate Acting % Essential Oil v/v | 6% | 2% | 1% | 0.5% |

*Out of an abundance of caution, stipulations could be made, for example such that the Extra Strength formula is only intended for short-term (1-14 days) use in adults 18 years or older, and in healthy elderly (preferably with less than 5 chronic illnesses) until safety is validated. The minimum amount (one drop) per site per day should be used, as the increased proportion of the long-acting loaded nanoparticles will continually deliver active ingredients.

It is advisable for the mixtures to be admixed in a 15-ml dark-glass (e.g., green or blue as these are darker and protect from light) dropper bottle for precise drop by drop administration (vs a roller ball top, which would be difficult to quantify the amount used).

Example 4

A Process for Preparing PP3

Prepare German Chamomile Essential Oil-Grain Alcohol Mixture for Long-Acting Portion:
1) Add 4 ml 120 proof grain alcohol to 4 fluid ounces (118 ml) of German chamomile essential oil to preserve chamazulene and bisabolol. Mix well. Set aside at room temperature for at least 1 hour before using.

Prepare Roman Chamomile Essential Oil-Grain Alcohol Mixture for Long-Acting Portion:
1) Add 1 ml 120 proof grain alcohol to 1 fluid ounce (30 ml) of Roman chamomile essential oil to preserve chamazulene and bisabolol. Mix well. Set aside. Set aside at room temperature for at least 1 hour before using.

Prepare German Chamomile Essential Oil-Grain Alcohol Mixture for Short-Acting Portion:
1) Add 0.5 ml 190 proof grain alcohol to 4 fluid ounces (118 ml) of German chamomile essential oil to preserve chamazulene and bisabolol. Mix well. Set aside at room temperature for at least 1 hour before using.

Prepare Roman Chamomile Essential Oil-Grain Alcohol Mixture for Short-Acting Portion:
1) Add 0.5 ml 190 proof grain alcohol to 4 fluid ounces (118 ml) of Roman chamomile essential oil to preserve chamazulene and bisabolol. Mix well. Set aside. Set aside at room temperature for at least 1 hour before using.

Prepare Moroccan Chamomile Oil-Grain Alcohol Mixture for Short-Acting Portion:
1) Add 1 ml 190 proof grain alcohol to 8 fluid ounces (236 ml) of Moroccan chamomile essential oil to preserve chamazulene and bisabolol. Mix well. Set aside. Set aside at room temperature for at least 1 hour before using.

Prepare Dead Sea Salt Solution:
1) Take a baking pan and line it with aluminum foil, shiny side up
2) Spread out several cups of dead sea salt and spread out in a 1-inch layer
3) Shine a Near Infrared Light bulb on the salt layer, positioning the bulbs no more than 3" away from the salt surface. Be sure that every salt surface is exposed to the light.
4) Shine the NIR Lights on the salt for at least 1 hour.
5) Dilute 1:10 in purified water (100 g salt in 1000 ml purified water). Allow time to dissolve the salts at room temperature, about 10-15 minutes.
6) Allow to cool and store in a glass bottle with a lid. Store remaining salt. Turn off NIR lights.

Prepare Saturated Dead Sea Salt Solution:
1) Add 1 cup of dead sea salt to 2 cups of water in a large glass jar, stir to mix thoroughly
2) Microwave for 3 minutes on high heat and stir to mix thoroughly.
3) Repeat microwaving at 1-minute intervals at high heat, stirring to force more salt to dissolve into the solution, until the liquid is visibly boiling
4) Remove from heat, stir thoroughly.
5) Keep covered at room temperature overnight.
6) Decant or pipette off the super saturated salt solution into a separate glass jar with a lid, leaving behind the remaining undissolved salt layer at the bottom.
7) Store super saturated salt solution at room temperature, covered.

Prepare Holy Anointing Oil:
1) Measure out 10 ml Organic Extra Virgin Olive Oil into a dark glass bottle with a secure dropper lid to protect from light.
2) Add 5 ml of organic Myrrh essential oil
3) Add 2.5 ml of organic Cinnamon essential oil
4) Add 2.5 ml of organic Calamus essential oil
5) Add 5 ml of organic Cassia essential oil
6) Add 5 ml of organic Frankincense essential oil
7) Mix well. Makes a total of 30 ml.
8) Keep in a dark glass bottle with a secure dropper lid to protect from light.
9) Keep away from light and store in a cool place.

Prepare Traditional Chinese Medicine Herbs:
1) In a glass quart jar with a lid, combine the following:
2) Organic Ginger essential oil 120 ml.
3) Organic Chinese Licorice (glycyrrhiza uralensis) (1-part Dry herb extracted in 3 parts water and mixed with vegetable glycerin Herbal Extract) 120 ml
4) Organic Bupleurum Chinese (1-part bupleurum extracted in 3 parts pharmaceutical grade alcohol and purified water, with vegetable glycerin as carrier) 240 ml
5) Total volume is 480 ml.

Prepare Seed and Orange Oil Blend:
1) In an amber glass jar with a lid, combine the following:
2) Organic Cold-Pressed Pomegranate seed oil 60 ml
3) Organic Cold-Pressed Orange essential oil 30 ml
4) Organic Cold-Pressed Blackseed essential oil 10 ml
5) Organic Clove essential oil 10 ml
6) Final volume 110 ml. Store in an amber glass bottle with lid until ready for use.

Prepare Long-Acting Loaded Biosilicates/Food Grade Diatomaceous Earth (FGDE):
1) Pour 500 ml of dead sea salt solution into a quart-sized glass jar with a lid.
2) Put on a mask and eye protection to prevent inhalation of dry FGDE which can cause interstitial lung disease from improper handling/inhalation.
3) Add 50 g of Food Grade Diatomaceous Earth to dead sea salt solution to hydrate and mineralize FGDE, thus preparing nanoparticles for loading with German chamomile essential oil and Roman chamomile essential oil.
4) Use whisk to create a homogeneous mixture
5) Add the German chamomile essential oil+alcohol mixture, as well as the Roman chamomile essential oil+alcohol to the FGDE+dead sea salt solution. Do not be alarmed as the oils will float to the surface, and the FGDE will eventually settle to the bottom.
6) Use whisk to create a homogeneous mixture
7) Add 15 g each of Organic Pea Protein and Organic Brown Rice Protein.
8) Add a total of 450 mg each of L-Histidine, L-Isoleucine, L-Leucine, L-Lysine, L-Methionine, L-Phenylalanine, L-Threonine, L-Valine)
9) Use whisk to create a homogeneous mixture
10) Add a total of 700 mg of Vitamin B-6
11) Use whisk to create a homogeneous mixture
12) Add a total of 7000 mg of N-Acetyl Cysteine
13) Use whisk to create a homogeneous mixture
14) Add a total of 3500 mg of Niacinamide
15) Use whisk to create a homogeneous mixture
16) Add a total of 7000 mg of Vitamin C
17) Use whisk to create a homogeneous mixture
18) Add a total of 10,500 mcg Retinol Activity Equivalents (RAE) as Vitamin A palmitate and 49 mcg RAE as beta-carotene.
19) Use whisk to create a homogeneous mixture
20) Add a total of 42,000 IU (1050 mcg) of Vitamin D.
21) Use whisk to create a homogeneous mixture
22) Cap tightly and store at room temperature overnight or until the blue oil layer floats to the surface.
23) Use whisk to create a homogeneous mixture
24) While homogenized, pour into a glass container large enough to hold at least 4000 ml
25) Fold in 960 ml of emu oil
26) Use whisk to create a homogeneous mixture out of the Traditional Chinese Medicine Herb Mixture. Pour 480 ml into the glass container with the main mixture and blend well.
27) Use whisk to create a homogeneous mixture out of the Seed and Orange Oil Blend. Add the 110 ml of the Seed and Orange Oil Blend to the main mixture and blend well.

28) Add 30 ml of Holy Anointing Oil to the main mixture and blend well. Makes a total of 2,713 ml.

This is the long-acting portion of the final preparation, as it contains the natural biosilicate nanoparticles loaded with German and Roman chamomile essential oils, complexed with vitamins, minerals, and amino acids. Be sure to mix to homogeneity prior to using.

Note: Alternatively, separate batches of diatoms/biosilicates/FDGE each individually loaded with one could be created (e.g., take dead sea saltwater-soaked diatoms already loaded with minerals and add each compound separately, creating for example vitamin-loaded FDGE, mineral-loaded FDGE, amino acid loaded FDGE, etc.), then take 1 aliquot of each type of loaded diatom and combine.

Prepare Instant-Acting Alcohol-Preserved Chamomile Blend:

1) Combine the alcohol-preserved German chamomile essential oil (120 ml total volume) with the alcohol-preserved Moroccan chamomile essential oil (240 ml total volume) with the alcohol-preserved Roman chamomile essential oil (120 ml total volume) for a final total volume of 480 ml.

Prepare Anxiolytic and Antidepressant Blend:

1) Combine organic jasmine grandiflorum essential oil and organic lemongrass essential oil in a 1:1 ratio. Store in a dark-colored glass container with lid until use.

Example 5

Pain Preparation 3.1 (PP3.1)

PP3.1 was prepared.

TABLE 3

PP3.1 Recipes

| | Function | Extra Strength* |
|---|---|---|
| Loaded Biosilicates (Long-Acting Fraction) | Time release delivery of minerals, amino acids, vitamins & bio-actives for long-acting relief of pain and anxiety, delivery of substances required for tissue repair. | 3 ml |
| German Chamomile | Immediate-acting relief of pain, anxiety, abnormal muscle tension, local allergy, itch, inflammation, rashes. Topical antimicrobial. | 0 ml |
| Moroccan Chamomile | | 2 ml |
| Roman Chamomile | | 0.5 ml |
| Jasminum Officinale Therapeutic Perfume Oil (Simplers Botanicals) | Diluted Perfume Oil to mask smell of German Chamomile | 1.25 ml |
| Vanilla Planifolia Therapeutic Perfume Oil (Simplers Botanicals) | Diluted Perfume Oil to mask smell of German Chamomile | 1.25 ml |
| Emu Oil | Penetrates human skin surface & confers this ability on admixed substances. Decreased in myristic acid, palmitoleic acid, and lauric acid as compared to human sebum. | 12 ml |
| Total Volume: | | 15 ml |
| Immediate Acting % Essential Oil v/v | | 17% |

Example 6

Anti-Aging, Anti-Wrinkle Properties of PP3.1

PP3.1 was applied sporadically (3× in 7 days) on a face for 2 weeks. After two applications, the patient noticed that the deep horizontal line across the bridge of the patient's nose that the patient had for the past 10 years was no longer visible unless the patient wrinkled the nose on purpose; and that the enlarged pores on the T-zone (forehead, nose, chin) were significantly smaller, the skin surface itself was finer and more radiant. PP3.1 reduced wrinkles and pore size, and improved skin radiance and texture.

Ingredients for PP1-PP3.1 were chosen and formulated so as to stimulate 4 canonical transcription factors Sox2, Oct-4, c-Myc, and Klf4 (PMID 16904174). It was reported that stimulation of Sox2, Oct-4, c-Myc, and Klf4 in terminally differentiated cells can reprogram them back into an undifferentiated stem cell state (e.g., using viral vectors to drive expression of transcription factors Sox2, Oct-4, c-Myc, and Klf4 in mature skin cells was sufficient to revert them back into a stem cell state) (See FIG. 25 and (PMID 16904174)). This original work (PMID 16904174) by Dr. Shinya Yamanaka earned him the Nobel Prize in Medicine but applications of his work have mostly remained in the lab and have not been translated into the clinical setting for use in human patients.

In essence, the difference between earlier work and PP3.1 appears to be that the latter transports a combination of signals into the cell using natural ingredients without the use of a viral vector and can transform the differentiated skin cells back into a "biologically younger" pluripotent stem cell state.

Figure 25:
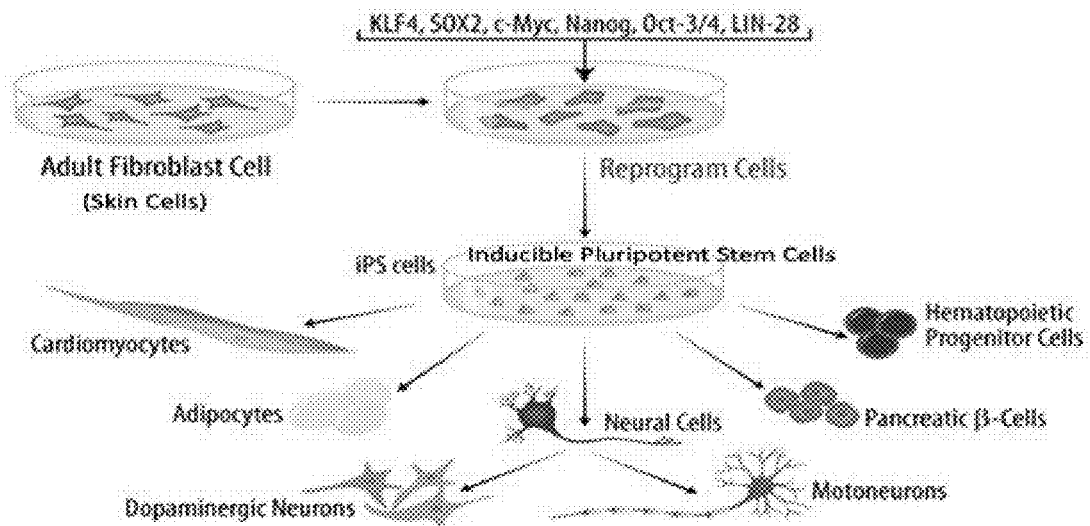
FIG. 25. Pluripotency Can Be Induced by Stimulation of 4 Transcription Factors in a Terminally Differentiated Cell to Give Rise to Multiple Other Cell Types. (obtained from http://2.bp.blogspot.com/-j9cpH1VCTFU/TiVeGabbeoI/AAAAAAAAAkI/W4c86aZASIY/s640/ipscs.jpg)
Figure 26:
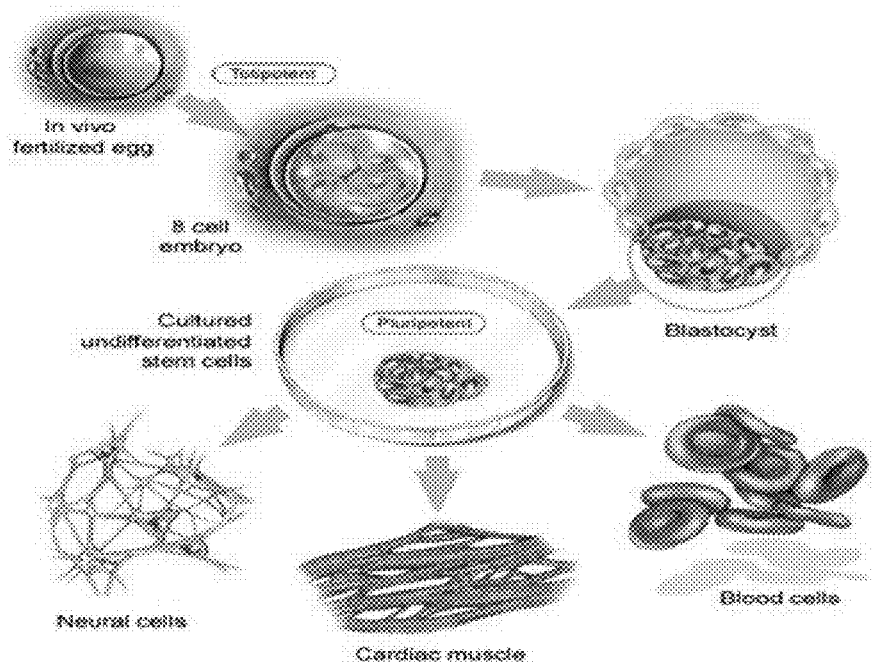
FIG. 26. Totipotent Stem Cells from Embryos Give Rise to Pluripotent Stem Cells Capable of Generating Multiple Cell Types (obtained from https://lh5.googleusercontent.com/-jZ3YrRhTVRU/TXhVpt4GvxI/AAAAAAAAAB4/pJoGVRefPwk/s1600/pluripotent-stem-cells.jpg)
Figure 27:
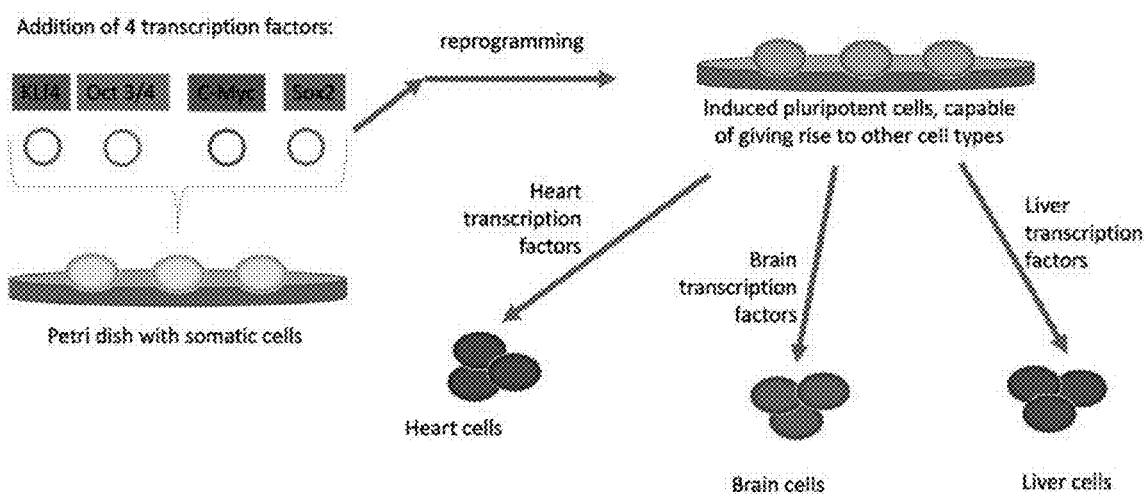
FIG. 27. Reprogramming of Somatic Cells to A Pluripotent Stem Cell Using 4 Transcription Factors (Yamanaka Transcription Factors)

Pluripotency is the ability to give rise to other cell types, depending on the signals in the cell's microenvironment; thus, it is possible to regenerate neurons, blood vessels, connective tissues, and a variety of other cell types appropriate to the specific cell environment (See FIG. 25). For example, when PP3.1 is applied to the scalp it activates hair follicles to produce more hair, when applied to the skin it stimulates production of additional connective tissue (such as within a wrinkle) or additional skin cells. The local environmental signals within any given tissue will direct the induced pluripotent stem cells to restore the tissue as needed. Signals within facial skin will direct production of more facial skin, while signals within the scalp will direct production of more follicles/hair. Thus, there is no concern for scalp hairs growing on the face, for example.

Increasing the number of stem cells in the skin has a potential to promote youthfulness, decrease inflammation, and promote rapid wound healing as well as the formation of new skin. It shall be noted that there are endless applications for any topical preparation capable of creating inducible stem cells out of terminally differentiated skin cells, or any other cell to which it is applied. For example, in a patient with peripheral neuropathy it may be possible to regenerate neurons in the tissues underlying the skin where PP3.1 is applied. In a patient with a burn requiring new blood vessels, connective tissue and skin cells it may be possible to regenerate each of these. All that is required is being able to deliver PP3.1 or future iterations into the injured tissue.

Example 7

Skin Brightening Properties of PP3.1

Use of PP3.1 resulted in more rapid healing of blemishes as well as a brightening effect. The quality of a patient's skin was more radiant, healthy, and vibrant. One possible explanation is that licorice root extract contains glabridin, which has been shown to inhibit melanogenesis and inflammation, as well as UBV-induced pigmentation (PMID 9870547). Coating the glabridin with the lipid mixture conferring skin penetrative properties delivered this into tissues leading to a skin-brightening effect.

Example 8

Hair Retention Properties of PP3.1

A few drops of PP3.1 was sporadically applied to the center part of a patient's scalp (1 application approximately every 3-7 days). Hair retention was noted, as well as growth of new hairs along the part.

Example 9

Ulcer Healing Properties of PP3.1

A patient developed a sore spot/ulcer when she accidentally bit the tip of her tongue. One drop of PP3.1 was placed on the ulcer and the pain instantly resolved on contact; the ulcer immediately began to heal and shrink in size, and by morning the ulcer was gone. This is a much more powerful response than in PP1, PP2 and PP3. The floral/bitter taste may be a repellent to some, but the effectiveness will likely make up for it. This preparation facilitates rapid healing by stimulating a stem cell response in the injured tissue, in addition to treating pain.

Example 10

Validation of Long-Term Release of Active Compounds and Lymph Fluid Drainage Properties of PP3.1

After a trauma, a patient was unable to lift her right leg more than an inch off the floor due to a sprained right groin, sprained right gluteus muscle, sprained right hip and lower back with rupture of one of the right pelvic stabilizing muscles in addition to disc herniation at L3 and L4. Approximately 10 drops of PP3.1 total were applied to affected areas and a set of near-infrared lamps were utilized for 5 minutes to allow for deeper penetration of PP3.1.

Twenty-three hours after application of PP3.1, the patient went to get a lymphatic drainage/deep tissue massage. The masseuse began working on the injured right gluteus/hip/groin and remarked that the area was neither inflamed nor swollen. The patient noted a lack of pain only on the areas where PP3.1 had been applied despite the superficial lymphatic drainage massage, which normally causes discomfort. When the masseuse began the same massage in areas where PP3.1 had not been applied, the patient experienced the usual discomfort.

It shall be noted that the patient was able to tolerate deeper pressure on the injured side as compared to the uninjured side. While the masseuse worked on the right/injured side the patient could feel light/medium/deep touch the same as usual; no numbness was noted. Therefore, it was hypothesized that a dampening of inflammation resulting in less lymph fluid trapped in the patient's tissues resulting in less pain. Additionally, PP3.1 could raise the patient's threshold for pain by insertion of lipids into cell membranes, disrupting multimerization of pain receptors which is required for pain signaling. The long-term fraction (the loaded biosilicate nanoparticles) was found to be effective reducing swelling and pain. Additionally, since the patient did not experience a recurrence of pain, inflammation or swelling (as would be expected within 4-6 hours after taking traditional non-steroidal anti-inflammatories), this is evidence that the FDGE loaded diatom nanoparticles are effective for extended release of bioactive compounds. One application of PP3.1 was sufficient to provide relief.

Example 11

Wound Healing Properties of PP3.1

A patient had idiopathic peripheral neuropathy of the bilateral lower extremities and was mostly without sensation from his knees down, and thus did not notice for over a month that he had developed a slowly spreading infection due to poor wound healing. Approximately 1-month post-injury he was seen in Urgent Care and prescribed an oral antibiotic (cephalexin) which failed to control the skin infection; he was then given oral Bactrim as a replacement however this also failed to control the cellulitis. Thus, he was hospitalized and received an IV antibiotic (clindamycin) overnight and then was discharged home on oral clindamycin. A few days later this was switched to oral linezolid, when it became apparent that his wound persisted without healing. He remained on linezolid for 3 weeks, and while MRI showed that the infection had not spread to his bone, the wound persisted.

The patient then showed his wound, which had not healed in the past four months, to a family medicine practitioner. The family medicine practitioner applied 3 drops of PP3.1 to the wound and covered up the patient's leg.

Twenty-four hours later, examination of the wound showed decreased edema, however some erythema and warmth near the wound site with some mild fluctuance underneath was noted. The Infectious Disease specialist who had been managing the patient's care was consulted and was told that observation without further antibiotic-intervention was appropriate. Desiring a more rapid healing response and noting the continued presence of infection in the wound, the family practitioner applied Antimicrobial Blend 1 formulation made in accordance with the present invention.

Antimicrobial Blend 1, or AB1 which was previously made by the inventor to protect against colds/flu was admixed with PP3.1 in a 1:1 ratio and spread in a thin layer over the patient's anterior right calf, and thickly over the wound site. A blow dryer was used diffusely for several minutes over the areas where the mixture was applied, to gently increase circulation.

Shortly after the application with heat, the wound skin began to change and turn mildly erythematous. Multiple tiny blebs measuring 2-3 mm formed, filled with a clear yellow serous fluid. These resolved within minutes to hours while the lesion itself began to coalesce. The patient noted that the heat helped so he spent the day sitting outside under the sun with his wound exposed to sunshine. The brawny changes of vascular insufficiency began dissipating within a few minutes of application+heat. The change was most noticeable 6 hours later.

After 6 hours, the edema dissipated, the patient's leg shrunk by at least about 30-40%, his wound had partly closed, and the brawny changes of venous insufficiency that had been there for decades were noticeably improved. When each application had fully absorbed into the skin, the patient would thickly apply a fresh round of AB1+PP3.1 and use the blow dryer or sunshine to improve absorption.

It shall be noted that this wound had not healed in 4 months, but when provided a combination of appropriate nutrients and bioactive ingredients the immune system and stem cells responded rapidly and appropriately. By the end of 9 hours his 3+ pitting edema of bilateral lower extremities had completely resolved. His brawny discoloration had minimized to the point of looking like a tan, and his wound had further shrunk in size to a small scab. His legs were more comfortable due to the resolved edema, he walked better, and he noted slightly improved sensation in both feet and lower legs. He stated that his balance had improved and that he felt steadier on his feet. In the past two decades with the progression of the peripheral neuropathy, the patient had gradually lost the hair on his anterior shins starting from the ankles and progressing upwards towards his knees. After several weeks of daily application of AB1+PP3.1, the patient noted regrowth of hair that began near his knees and progressed downwards towards his ankles.

The patient also noted that previously he was unable to wear his moccasin house slippers as his ankles and feet were so swollen that he would struggle to fit his feet into his slippers. 9 hours after initial treatment the patient's ankles were normal in size and shape such that his slippers were actually loose, with a large gap causing the moccasins to fall off his foot, which he had never experienced before.

It was concluded that AB1+PP3.1 in a 1:1 ratio may be used in wound care to help non-healing wounds to close rapidly, to improve edema and to improve regrowth of hair. However due to the strong smell and concentration of AB1 care will need to be used when applying the mixture on the face or near mucus membranes. It is important to note that a patient must first be patch-tested for allergies to the mixture, which should not be applied to broken skin.

Example 12

Antimicrobial Blend (AB1)

To 500 ml Organic Extra Virgin Olive Oil add:
30 ml Clove essential oil (*Eugenia caryophyllus*)
30 ml Cinnamon essential oil (*Cinnamonum cassia*)
30 ml Rosemary essential oil (*Rosmarinus officinalis*)
30 ml Eucalyptus essential oil (*Eucalyptus globulus*)
30 ml Lemon essential oil (*Citrus limon*)
10 ml Ravintsara essential oil (*Cinnamomum camphora*)
5 ml Cinnamon Leaf essential oil (*Cinnamomum vera*)
Mix all ingredients well. Store in a dark glass bottle and protect from heat and light. This 165 ml of essential oil to 665 ml total volume, or a 1:4 dilution.

Example 13

Pain Preparation 4 (PP4)

Pain Preparation 4 (PP4) incorporates the following designs and improvements, among others if desired. The main improvement here will be the addition of vegetable oils in proportions that will bring it closer to mimicking human skin/oil.

TABLE 4

PP4 Formulation Sample Recipes by Patient Population

| | Function | Extra Strength* | Adult (>18 yo) | Elderly or Child <18 | Infant <1 yr |
|---|---|---|---|---|---|
| Loaded Biosilicates | Time release delivery of minerals, amino acids, vitamins & bio-actives for long-acting relief of pain and anxiety, delivery of substances required for tissue repair. | 3 ml | 2 ml | 1 ml | 0.5 ml |
| German Chamomile | Immediate-acting relief of pain, anxiety, abnormal muscle tension, local allergy, itch, inflammation, rashes. Topical antimicrobial. | 0.15 ml | 0.05 ml | 0.025 ml | 0.0125 ml |
| Moroccan Chamomile | | 0.30 ml | 0.10 ml | 0.05 ml | 0.025 ml |
| Roman Chamomile | | 0.15 ml | 0.05 ml | 0.025 ml | 0.0125 ml |
| Jasmine | Immediate-acting relief of anxiety, insomnia and abnormal muscle tension | 0.15 ml | 0.05 ml | 0.025 ml | 0.0125 ml |
| Lemongrass | Immediate-acting relief of pain, depression, fever, abnormal muscle tension & spasms, insomnia. Topical antimicrobial. Anticancer activity | 0.15 ml | 0.05 ml | 0.025 ml | 0.0125 ml |
| Coconut Oil | Supplements lauric acid in Emu Oil to mimic human sebum | 0.5 ml | 0.5 ml | 0.5 ml | 0.5 ml |
| Macadamia | Supplements myristic and palmitoleic acids in emu oil to mimic human sebum | 4 ml | 4 ml | 4 ml | 4 ml |

TABLE 4-continued

PP4 Formulation Sample Recipes by Patient Population

| | Function | Extra Strength* | Adult (>18 yo) | Elderly or Child <18 | Infant <1 yr |
|---|---|---|---|---|---|
| Emu Oil | Penetrates human skin surface & confers this ability on admixed substances. Decreased in myristic acid, palmitoleic acid, and lauric acid as compared to human sebum. | 6.6 ml | 8.2 ml | 9.35 ml | 9.92 ml |
| | Total Volume: | 15 ml | 15 ml | 15 ml | 15 ml |
| | Immediate Acting % Essential Oil v/v | 6% | 2% | 1% | 0.5% |

*Out of an abundance of caution, stipulations could be made, for example such that the Extra Strength formula is only intended for short-term (1-14 days) use in adults 18 years or older, and in healthy elderly (preferably with less than 5 chronic illnesses) until safety is validated. The minimum amount (one drop) per site per day should be used, as the increased proportion of the long-acting loaded nanoparticles will continually deliver active ingredients.

Note that the mixtures should be admixed in a 15-ml dark-glass (preferably green or blue as these are darker and protect from light) dropper bottle for precise measurement.

The inventor learned from the above cases that the immediate-acting essential oils are effective and may potentially be used safely in concentrations closer to 20%-30%, in contradistinction to the 6% or lower, as described in various textbooks.

Example 14

PP5. Pain Preparation 5

PP5 was prepared as follows:
1) Long-Acting Loaded Biosilicates/Food Grade Diatomaceous Earth (FGDE): 3 ml
2) 1:1:1 mixture of German chamomile essential oil, Moroccan chamomile essential oil, Roman chamomile essential oil: 2.5 ml
3) 1:1 mixture of Jasmine and Lemongrass essential oils: 2.5 ml
4) MNO+CO (Macadamia Nut Oil+Coconut Oil Stock): 2.0 ml
5) Mix all the above in a 15 ml glass dropper bottle to homogeneity
6) Divide contents into 3 15 ml glass dropper bottles add emu oil up to 15 ml.
7) Store at room temperature, protect from light and heat.

Example 15

PP6. Pain Preparation 6

TABLE 5

PP6 Formulation Sample Recipes by Patient Population

| | Function | Extra Strength* | Adult (>18 yo) | Elderly or Child <18 | Infant <1 yr |
|---|---|---|---|---|---|
| Loaded Biosilicates | Time release delivery of minerals, amino acids, vitamins & bio-actives for long-acting relief of pain and anxiety, delivery of substances required for tissue repair. | 3 ml | 2 ml | 1 ml | 0.5 ml |
| German Chamomile | Immediate-acting relief of pain, anxiety, abnormal muscle tension, local allergy, itch, inflammation, rashes. Topical antimicrobial. | 0.15 ml | 0.05 ml | 0.025 ml | 0.0125 ml |
| Moroccan Chamomile | | 0.30 ml | 0.10 ml | 0.05 ml | 0.025 ml |
| Roman Chamomile | | 0.15 ml | 0.05 ml | 0.025 ml | 0.0125 ml |
| Frankincense | Immediate-acting relief of pain, disrupts lipid rafts, modulation of pain receptors | 1 ml | 0.75 ml | 0.5 ml | 0.25 ml |
| Myrrh | | 1 ml | 0.75 ml | 0.5 ml | 0.25 ml |
| Jasmine | Immediate-acting relief of anxiety, insomnia and abnormal muscle tension | 0.15 ml | 0.05 ml | 0.025 ml | 0.0125 ml |
| Lemongrass | Immediate-acting relief of pain, depression, fever, abnormal muscle tension & spasms, insomnia. Topical antimicrobial. Anticancer activity. | 0.15 ml | 0.05 ml | 0.025 ml | 0.0125 ml |
| Coconut Oil | Supplements lauric acid in Emu Oil to mimic human sebum | 0.5 ml | 0.5 ml | 0.5 ml | 0.5 ml |
| Macadamia | Supplements myristic and palmitoleic acids in Emu Oil to mimic human sebum | 4 ml | 4 ml | 4 ml | 4 ml |

TABLE 5-continued

PP6 Formulation Sample Recipes by Patient Population

| | Function | Extra Strength* | Adult (>18 yo) | Elderly or Child <18 | Infant <1 yr |
|---|---|---|---|---|---|
| Emu Oil | Penetrates human skin surface & confers this ability on admixed substances. Decreased in myristic acid, palmitoleic acid, and lauric acid as compared to human sebum. | 6.6 ml | 8.2 ml | 9.35 ml | 9.92 ml |
| | Total Volume: | 17 ml | 16.5 ml | 16 ml | 15.5 ml |
| | Immediate Acting % Essential Oil v/v | 17% | 11% | 7% | 3.7% |

Example 16

Preparation of Macadamia Nut Oil+Coconut Oil Stock Mixture "MNO+CO"

The MNO+CO mixture could be prepared as follows:
1) Gently warm 60 ml coconut oil in a 75-degree water bath until melted (coconut oil melts above 72 degrees F.).
2) Add to 400 ml macadamia nut oil and mix well until completely homogeneous
3) Store at room temperature until ready for use, it will remain liquid.

Example 17

Preparation of Basic "Liquid Skin" (Emu/Vegetable Oil Blend Mimicking Human Sebum Fatty Acid Composition)

Liquid skin could be prepared as follows.
1) Add 107 ml of MNO+CO (macadamia nut oil+coconut oil stock) to 1893 ml Emu Oil and blend thoroughly until completely homogeneous.
2) Aliquot into glass bottles. Store at room temperature.
3) It is ready to apply or may be admixed with other bioactive compounds.

Example 18

Preparation of basic "Vegan Liquid Skin"

Vegan Liquid Skin could be prepared as follows:
1. Add 107 ml of MNO+CO (macadamia nut oil+coconut oil stock) to 1893 ml high oleic sunflower seed oil and blend thoroughly until completely homogeneous.
2. Aliquot into glass bottles. Store at room temperature.
3. It is ready to apply or may be admixed with other bioactive compounds.
4. Note that basic "Liquid Skin" or "Vegan Liquid Skin" is sufficient to improve incorporation and absorption of other bioactive compounds into the skin. Both of these may further be modified by addition of ceramides, phospholipids and other compounds as listed in the chart below.

Example 19

Antimicrobial Blend 1 (AB1)

AB1 is an antimicrobial formula with antibacterial, antifungal, and antiviral properties. Antibacterial properties are strongest, followed by antiviral, then antifungal. AB1 could be prepared as follows:
1) Pour 1/2 gallon of high oleic sunflower seed oil=1893 ml into a 2 L glass jar with lid
2) Add 107 ml of MNO+CO2 (macadamia nut oil+coconut oil stock) for a final volume of 2000 ml
3) Add 120 ml each of essential oil of clove, cinnamon, rosemary, eucalyptus, lemon as well as 40 ml of ravintsara essential oil, 20 ml of cinnamon leaf essential oil
4) Mix well and store at room temperature. Protect from excess heat and light.

Example 20

Antimicrobial Blend 2 Oil

AB2 is an antimicrobial formula with wound healing, antibacterial, antifungal, and antiviral properties). AB2 could be prepared as follows:
1) Pour ½ gallon of high oleic sunflower seed oil=1893 ml into a 2 L glass jar with lid
2) Add 107 ml of MNO+CO2 (macadamia nut oil+coconut oil stock) for a final volume of 2000 ml
3) Add 120 ml each of essential oil of clove, cinnamon, rosemary, eucalyptus, lemon as well as 40 ml of ravintsara essential oil, 20 ml of cinnamon leaf essential oil, and 30 ml of frankincense essential oil
4) Mix well and store at room temperature. Protect from excess heat and light.

Example 21

Antimicrobial Blend 2 Lite

ABL2 is a dilute version of AB2. AB2 is diluted by 50% by doubling the carrier oil. It is more tolerable for those who are sensitive to strong smells and for children and elderly.

Example 22

Antimicrobial Blend 2 Breathe Formula

AB2B is based on AB2 and includes additional ingredients to facilitate bronchodilation. It may be prepared as follows.

1) Pour 1/2 gallon of high oleic sunflower seed oil=1893 ml into a 2 L glass jar with lid
2) Add 107 ml of MNO+CO2 (macadamia nut oil+coconut oil stock) for a final volume of 2000 ml
3) Add 500 ml essential oil of peppermint, 120 ml each of essential oil of clove, cinnamon, rosemary, eucalyptus, lemon as well as 40 ml of ravintsara essential oil, 20 ml of cinnamon leaf essential oil, and 30 ml of frankincense essential oil, 90 ml spearmint essential oil, and 30 ml wintergreen essential oil.
4) Mix well and store at room temperature. Refer to Table 1 for dosing of wintergreen essential oil.

Example 23

AB1 Triple Antimicrobial Formula

AB1T is based on AB2 but include white thyme essential oil. 120 ml of white thyme essential oil is added to the formulation of AB2 for additional antiviral, antibacterial, and antifungal benefits.

A 40-year-old female with toenail fungus of all toenails for the past three years had tried multiple prescription and over-the-counter medical treatments but the fungus persisted, resulting in discolored, brittle, porous toenails. She was unable to wear toenail polish as it worsened the infection. 30 minutes after she applied AB1 T to affected areas, the areas with fungal infection, including the nailbeds and surrounding skin had become reddened. 24 hours after application of AB1T, the reddening had resolved, and the appearance of the toenails normalized. Following the application, the brittle and porous nails grew out and were replaced with healthy toenails. The toenail fungus has not recurred since initial application of AB1T.

Example 24

Antimicrobial Blend Extended-Release Formula
(AB1 ER—Formulated with FDGE for Extended Release of Active Compounds)

AB1 ER can be prepared as follows:
1) While properly masked and in a ventilated space, add 60 g of FDGE to 250 ml of saturated dead sea salt water and mix well.
2) Add 250 ml ABL1, (or whichever formula desired to be made into an extended release)
3) Add 24 ml of emu oil
4) Add 10 ml of MNO+CO2 (macadamia nut oil+coconut oil stock)
5) Mix well and label as AB1 ER fraction.
6) Add 3 ml of AB1 ER to a 15 ml glass dropper bottle
7) Add balance of AB1 up to 15 ml.
8) Shake and mix well to homogeneity prior to use.
9) Store at room temperature and protect from heat and light Example 25

Wound Healing Formula (AB1+PP3/PP4/PP5 or subsequent PP formulas combined in a 1:1 ratio); to be applied to intact skin surrounding a wound to facilitate rapid healing. May apply Near Infrared Light or heat or sunlight as described above to stimulate stem cells and further facilitate rapid wound healing.

Example 26

Antimicrobial Blend Formula 1 (ABUF1)

ABUF1 has a high potency activity against bacteria, fungi, and viruses. ABUF1 can be prepared as follows:
1) Pour ½ gallon of high oleic sunflower seed oil=1893 ml into a 2 L glass jar with lid
2) Add 107 ml of MNO+CO2 (macadamia nut oil+coconut oil stock) for a final volume of 2000 ml
3) Add 1000 ml olive oil
4) Add 120 ml each of essential oil of clove, cinnamon, rosemary, eucalyptus, lemon as well as 40 ml of ravintsara essential oil, 20 ml of cinnamon leaf essential oil, 30 ml of frankincense essential oil, 30 ml each of white thyme, rosalina, palmarosa, niaouli, laurel leaf, and litsea leaf essential oils.
5) Mix well and store at room temperature. Protect from excess heat and light.

A 60-year-old female presented with sudden onset development of localized reddening, swelling, and purple patches on her fingers which spread from finger to finger of both hands for several weeks despite steroid creams prescribed by her dermatologists. She was unable to bend her fingers or use her hands due to the pain and swelling. After ruling out autoimmune and other differential diagnoses, biopsy showed she had vasculitis of unknown cause suspected to be COVID fingers as she met clinical criteria for COVID infection. After application of ABUF1 several times daily to her hands the swelling and pain decreased, allowing her to use her hands again without discomfort. The lesions stopped spreading, and by one week the lesions had faded.

A 62-year-old F with a history of Raynaud's phenomenon since her youth applied ABUF1 to her hands and noted relief from poor circulation, pain, and swelling of her hands upon application.

A 60-year-old F with a history of Rheumatoid Arthritis (RA) on standard prescription medications for RA noted improvement of painful joints within a few minutes after AB1 or ABUF1 was applied to hands, shoulders, and knees.

Example 27

Antimicrobial Blend Formula 2 (ABF2)

ABUF2 has high potency activity against bacteria, fungi, viruses and trypanosomes. ABF2 could be prepared as follows:
1) Pour 1/2 gallon of high oleic sunflower seed oil=1893 ml into a 2 L glass jar with lid
2) Add 107 ml of MNO+CO2 (macadamia nut oil+coconut oil stock) for a final volume of 2000 ml
3) Add 1000 ml olive oil
4) Add 120 ml each of essential oil of clove, cinnamon, rosemary, eucalyptus, lemon, xiang mao, white thyme, and lemongrass (Cymbopogon citratus)
5) Add 40 ml each of ravintsara, frankincense, and myrrh essential oils
6) Add 30 ml each of rosalina, palmarosa, niaouli, laurel leaf, and litsea leaf essential oils
7) Add 20 ml of cinnamon leaf essential oil
8) Mix well and store at room temperature. Protect from heat and light.

Example 28

Lymphedema Formula (AB1LY)

AB1LY can be prepared as follows:
1) Pour ½ gallon of high oleic sunflower seed oil=1893 ml into a 2 L glass jar with lid
2) Add 107 ml of MNO+CO2 (macadamia nut oil+coconut oil stock) for a final volume of 2000 ml
3) Add 150 ml of lemon, rosemary, and cinnamon essential oils
4) Add 120 ml each of essential oils of clove, eucalyptus, frankincense and myrrh
5) Add 40 ml of ravintsara essential oil
6) Add 30 ml each of grapefruit, fennel, cypress, geranium, juniper berry essential oils
7) Add 20 ml of cinnamon leaf essential oil
8) Mix well and store at room temperature. Protect from excess heat and light.

AB1LY could be applied topically to reduce swelling.

Example 29

Hypertension Formula (HYPF1)

HYPF1 can be prepared as follows:
1) Pour ½ gallon of high oleic sunflower seed oil=1893 ml into a 2 L glass jar with lid
2) Add 107 ml of MNO+CO2 (macadamia nut oil+coconut oil stock) for a final volume of 2000 ml
3) Add 120 ml each of essential oil of frankincense, myrrh, galangal, xiang mao, melissa (lemon balm)
4) Add 30 ml each of essential oil of lavender, bergamot, clary sage, rose, sweet marjoram, coriander, celery seed, wintergreen, neroli.
5) Add 5 drops each of essential oil of jasmine and ylang ylang.
6) Mix well and store at room temperature. Protect from excess heat and light.

HYPF1 could be applied topically to address headaches and other symptoms associated with hypertension while waiting for anti-hypertensive medications to work. Note the recommendations for dosing of wintergreen essential oil listed in Table 1.

Example 30

Headache Formula (HDF1)

HDF1 could be prepared as follows:
1) Pour ½ gallon of high oleic sunflower seed oil=1893 ml into a 2 L glass jar with lid
2) Add 107 ml of MNO+CO2 (macadamia nut oil+coconut oil stock) for a final volume of 2000 ml
3) Add 240 ml each of peppermint and galangal essential oil
4) Add 120 ml each of essential oil of frankincense, myrrh, xiang mao, melissa (lemon balm)
5) Add 60 ml each of essential oil of wintergreen, and neroli
6) Add 5 drops each of essential oil of jasmine and ylang ylang
7) Mix well and store at room temperature. Protect from excess heat and light.

HDF1 could be applied topically to address headaches. Note the recommendations for dosing of wintergreen essential oil listed in Table 1.

Example 31

Relaxation/Sleep Formula

Relaxation/Sleep formula could be prepared as follows:
1. Pour ½ gallon of high oleic sunflower seed oil=1893 ml into a 2 L glass jar with lid
2. Add 107 ml of MNO+CO2 (macadamia nut oil+coconut oil stock) for a final volume of 2000 ml
3. Add 300 ml of peppermint essential oil, 120 ml of geranium essential oil, along with 60 ml each of orange and frankincense essential oils, 30 ml each of blue tansy and celery seed essential oils, 1 ml each of licorice and ginger extract
4. Add 5 drops each of essential oil of jasmine and ylang ylang
5. Mix well. Divide into two 2 L glass jars with lids and per jar add 30 ml MNO+CO (macadamia nut oil+coconut oil stock), 473 ml emu oil, with 1000 ml of high oleic sunflower seed oil
6. Mix well and store at room temperature. Protect from excess heat and light.

Relaxation/Sleep formula could be applied topically to the face, back of the neck and throat prior to bedtime.

Example 32

Hair Growth

A topical formula that stimulates hair growth could be prepared as follows:
1. Pour ½ A gallon of high oleic sunflower seed oil=1893 ml into a 2 L glass jar with lid
2. Add 107 ml of MNO+CO2 (macadamia nut oil+coconut oil stock) for a final volume of 2000 ml
3. Add 1000 ml emu oil
4. Add 2000 g of lecithin and blend at high speed until fully dissolved and homogeneous.
5. Add 240 ml each of rosemary and pine needle essential oils
6. Add 120 ml each of essential oil of clove, cinnamon, rosemary leaf, eucalyptus, lemon, frankincense, and myrrh
7. Add 40 ml of ravintsara essential oil, 20 ml of cinnamon leaf essential oil
8. Add 30 ml each of essential oil of lavender, peppermint, carrot seed oil, geranium, and ginger essential oils. This is the instant acting portion of the Hair Growth Topical Formula
9. Mix well and store at room temperature. Protect from excess heat and light.
10. To make the Long-Acting Portion for Hair Growth Topical with FDGE: In a separate 500 ml glass container, mix 350 ml of saturated dead sea salt water to 200 g of FDGE (be sure to properly mask with N95 and work in a ventilated area to avoid breathing in dry FDGE). Mix well and add 750 mg each of essential amino acids (L-histidine, L-isoleucine, L-leucine, L-lysine, L-methionine, L-phenylalanine, L-threonine, L-valine in 1:1:1:1:1:1:1). Mix well until fully dissolved. Then add 50,000 mg biotin and mix well until fully dissolved. Add 10,000 mg vitamin C and mix well until fully dissolved. Add 4 g of zinc and mix well until fully dissolved. Add 4 g of a vitamin B complex (approximately 100 ng thiamine, 100 ng riboflavin, 200 ng niacin, 160 ng vitamin B6, 800 mcg folate, 1000 mcg vitamin B12, 400 mcg biotin, 100 mg pantothenic acid, 100 mg PABA, 77 mg phosphatidylcholine, 42 mg inositol, 200 mcg alpha-lipoic acid) and mix well until fully dissolved. Then add 100 ml of the previously made instant acting portion of the Hair Growth Topical Formula and mix well. Add 10 drops of 1,500 mcg RAE/drop and 1 fluid ounce of 125 mcg/500 mcg of vitamin D3 and K2 respectively. Mix well until fully dissolved. Add 50 g of ubiquinol which has been warmed in a water bath at 46 degrees C. until liquid and mix well. This is the Long-Acting Portion for Hair Growth.
11. Into each 15 ml bottle add 3 ml of Long-Acting Portion for Hair Growth. Add 12 ml of the Hair Growth Topical Formula (Instant Acting Portion).
12. Store at room temperature. Protect from excess heat and light. Mix well before applying to scalp daily at bedtime. For best results apply twice daily.

Example 33

Gastrointestinal Tract Healing Preparation

A formulation for oral administration for gastrointestinal tract healing could be prepared as follows:
1. Pour ½ gallon of emu oil=1893 ml into a 2 L glass jar with lid
2. Add 107 ml of MNO+CO2 (macadamia nut oil+coconut oil stock) for a final volume of 2000 ml
3. Add 100 ml of German chamomile/Roman chamomile/Moroccan chamomile essential oils that have been pre-mixed in a 1:1:1 ratio
4. Add 100 ml each of ginger and galangal essential oils.
5. Add 1300 g of lecithin granules and blend at high speed until fully homogenized.
6. Create 1000 mg gel capsules from this mixture. Use 4 gel formulations for capsules that are rapidly dissolving, intermediate dissolving, delayed dissolving, and extended delay dissolving in order to target the various parts of the digestive tract. For example, the rapidly dissolving capsules would be most useful for healing peptic ulcers of the most proximal parts of the gastrointestinal tract such as the stomach; the intermediate release would be best for healing duodenal ulcers, delayed release would be best for healing jejunal or ileal lesions, and extended delay release best for healing diseases of the colon and rectum such as in Ulcerative Colitis. Crohn's Disease affects any part of the GI tract and will require treatment with all four types of gel capsules. Suppositories of this formula can also be made to treat internal hemorrhoids and can be applied topically to external hemorrhoids. This formulation should help stimulate regeneration of the mucosal lining.
7. Case report: A patient had been bedridden for 2 decades with Ulcerative Colitis due to severe abdominal pain and diarrhea up to 15 times daily despite state-of-the-art treatment with mesalamine, biologics and steroids. He could only get up to use the bathroom. A family medicine practitioner advised him to take 1 g of emu oil daily, and to increase by 1 g per week until symptoms resolved, or side effects were encountered (at which point he should revert to dose that did not produce side effects). The patient took the emu oil as advised and within 1 week reported decreased abdominal pain, less frequent diarrhea to only 1-2 times daily, and that he was now able to participate in activities of daily living such as driving, shopping and running errands. He increased up to 2 g daily and was able to wean off prescription medications and eventually stopped taking the emu oil capsules.
8. Phosphatidylcholine (PC) is an important component of the mucosa of the GI tract and acts as a surfactant within the mucus to create a barrier which protects against erosion and microbial invasion. PC is critically reduced in patients with Inflammatory Bowel Disease, which includes Crohn's disease and Ulcerative Colitis (Parian et al Inflammatory Bowel Disease, Integrative Medicine Fourth Edition, 2018). For this reason, lecithin was incorporated into the formula to replenish PC in this patient population. The chamomile mixture combined with the emu oil will further stimulate mucosal stem cells to regenerate and repair ulcerated and inflamed tissues while reducing inflammation, and the macadamia and coconut oils will provide essential components of the cell membrane to repair a new gut lining.

The formulation may be taken internally.

Example 34

Insomnia Nasal Spray (INS1)

INS1 is a formulation for treating insomnia, anxiety, and improve metabolism of fat. INS1 could be prepared as follows:
1. In 2.5 L glass jar with lid, add 1155 ml high oleic sunflower seed oil to 660 ml of emu oil and 132 ml MNO+CO (macadamia nut oil+coconut oil stock) along with 67 ml of 3 mg/1 ml melatonin (to provide a final concentration of 100 mcg/ml or 100 meg/spray). This spray can be administered intranasally up to 4 sprays per night, as the 300 meg dose of melatonin has been shown to sufficient to restore melatonin levels to that characteristic of healthy young patients, are the best tolerated, improve sleep, do not lead to daytime grogginess, and avoid desensitization of melatonin receptors (Wurtman et. al. Low Doses of Melatonin Promote sleep Onset and Maintenance in Older People—An Update US Neurology, 2014; 10(2):117-9). Four sprays are allowed for loss of spray due to dripping.
2. Add 32 tablespoons of lecithin as an emulsifier and antioxidant and blend at high speed until fully homogenized.
3. To decrease anxiety and improve metabolism and fat utilization/lipolysis, add sterile filtered, stabilized oxytocin for a final dose of 24 international units (IU) per 1 ml spray for adults, or 12 IU per 1 ml spray for children (PMID 29898580, PMID 24067301, PMID 24297883, PMID 24352377) as well as 4 ml of organic Moroccan chamomile (*Tanacetum annuum*) essential oil for additional anti-anxiety benefits. Mix well at high speed until fully homogenized and aliquot into dark glass nasal spray bottles which dispense 1 ml per spray. Mix well prior to each administration.

Example 35

Eczema Preparation

An eczema preparation, in volume %, from about 15% to about 50% linoleic acid; and from about 0.05% to about 50% by volume for each type of chamomile essential oil (Roman/German/Moroccan chamomile); and from about 0% to about 5% of orange oil may be prepared. The formulation includes hyaluronic acid at a concentration between 0.05%-60% by volume. C16:1Δ6 fatty acids comprise between 5%-40% of the formulation by volume. The formulation may include full complement of 3:1:1:1 cholesterol, phospholipids, required to rebuild the skin barrier.

For a 15 ml bottle, 1-3 ml of the Long-Acting Preparation may be added.

Example 36

The Psoriasis/Eczema/Wrinkles/Anti-Aging/Formula (PEWAF1)

A formulation for treatment of eczema and psoriasis may be prepared as follows:
1. To 6×15 ml of PP4 (90 ml total) add 10 ml of AB1.
2. Mix well.
3. Add 96,0000 IU vitamin D
4. Add 6 ml hyaluronic acid
5. Add 6 ml vitamin E (1200 mg d-alpha tocopherol)
6. Add 30 drops Vit A (1507 mcg RAE/drop)
7. Add 6 ml vegetable glycerin
8. Add 6 ml vit K2 (MK7) 45 mcg/2 drops (note that 1 ml=20 drops)
9. Add 12 ml FDGE mixture as described previously
10. Add 400 mg ubiquinol which has been warmed to 46 degrees C. to melt it.
11. Mix well until homogenized and distribute into 15 ml glass dropper bottles. Should make about 9 bottles. Protect from heat and light.

The above formulation was tested and resolved new onset eczema in an adult woman in her 30's (lesions had cropped up in the past 2 weeks) after 2 applications applied 24 hours apart. The woman reported that the formula decreased itch on contact.

The formulation was tested in a man in his late 30's and a man in his early 40's, both who reported several year histories of eczema; both patients reported resolution of eczema after 3 applications applied 24 hours apart.

The formulation was also tested in a man in his 60's and resolved his persistent eczema which had been present for 3 years after 5 applications of the formula applied approximately 24 hours apart. At a 1-year follow-up, he reported zero recurrences after resolution with the 5$^{th}$ application.

The formulation was also tested in two children aged 1.5 years old (female) and 4 years old (male). Both pediatric patients reported improved pain on application. Peri-oral eczema was noted to have resolved completely in both children within 9 hours of application, with zero recurrences reported after resolution at a 1-year follow-up.

The formulation was tested in a female patient in her early 30's with a history of severe eczema since infancy which cropped up on all skin surfaces, including the genitals. She reported having tried various commercially available prescription and over-the-counter eczema formulas, including high potency steroids, and reported that she had allergic reactions to many of these topicals and that the steroid topicals eventually decreased in efficacy over time. Despite being on dupilumab injections twice per week she still reported severe eczema flares over large regions of skin. To date, the patient completed 5 applications of PEWAF2 24 hours apart and noted significant improvement after each application, but only on the areas where she applied the PEWAF2. Lesioned areas where she did not apply PEWAF2 remained lesioned. No allergic reactions were observed. Improvements included closing of open wounds and pinpoint bleeding, decreased pain, pruritus and erythema.

Example 37

Psoriasis/Eczema/Wrinkles/Anti-aging Formula 2 (PEWAF2)

PEWAF2 may be prepared as follows:
1) To 12 ml of PP4 add 1.5 ml AB1
2) Mix well.
3) Add 50,000 IU vitamin D
4) Add 2 ml Hyaluronic Acid
5) Add 2 ml vitamin E
6) Add 60 drops Vit A (1507 mcg RAE/drop)
7) Add 1 ml vegetable glycerin
8) Add 2 ml vit K2 (MK7) 45 mcg/2 drops (note that 1 ml=20 drops, so a total of 900 mcg.
9) Add 3 ml FDGE as described previously
10) Add 600 mg ubiquinol which has been warmed to 46 degrees C. to melt it.
11) Make myrrh+frankincense essential oil stock mixture as follows: add 30 ml myrrh essential oil to 45 ml frankincense essential oil and mix well. Store in a dark glass bottle with dropper.
12) Add 2 drops of the myrrh+frankincense essential oil stock mixture.
13) Add 1 ml of saturated dead sea salt solution
14) Add 1 ml of the 1:1:1 German chamomile+Roman chamomile+Moroccan chamomile essential oil stock mixture
15) Mix well until homogenized and distribute into 15 ml glass dropper bottles. Protect from heat and light. Apply to skin lesions.

PEWAF2 may be used for treatment of psoriasis, eczema, wrinkles and/or reducing/slowing down appearance of aging.

Example 38

Psoriasis/Eczema/Wrinkles/Anti-aging Formula with Anti-Itch Properties 3 (PEWAF3)

PEWAF3 may be prepared as follows:
1. To 12 ml of PP4 add 1.5 ml AB1
2. Mix well.
3. Add 50,000 IU vitamin D
4. Add 2 ml Hyaluronic Acid
5. Add 2 ml vitamin E
6. Add 60 drops Vit A (1507 mcg RAE/drop)
7. Add 1 ml vegetable glycerin
8. Add 2 ml vit K2 (MK7) 45 mcg/2 drops (note that 1 ml=20 drops, so a total of 900 mcg.
9. Add 3 ml FDGE as described previously
10. Add 600 mg ubiquinol which has been warmed to 46 degrees C. to melt it.
11. Make myrrh+frankincense essential oil stock as follows: add 30 ml myrrh essential oil to 45 ml frankincense essential oil and mix well. Store in a dark glass bottle with dropper.
12. Add 2 drops of the myrrh+frankincense essential oil stock.
13. Add 5 drops of essential oil of zanthoxylum coreanum nakai
14. Add 1 ml of saturated dead sea salt solution 15. Add 1 ml of the 1:1:1 German chamomile+Roman chamomile+Moroccan chamomile essential oil mixture.
16. Mix well until homogenized and distribute into 15 ml glass dropper bottles. Protect from heat and light. Apply to skin lesions.

PEWAF2 may be used for treatment of particularly itchy psoriasis, eczema, insect bites and other itchy rashes.

Example 39

Eczema Hand Healing Kit

A kit comprises one or more formulation(s) according to the invention, a sealing/occlusive barrier cream, and a 100% organic cotton gloves, and a set of instructions. Instructions may, e.g., recommend patient to wash affected areas with lukewarm water, then pat skin with towel leaving skin moist; immediately apply hydrated hyaluronic acid mixed with Liquid Skin (1:1) blend first, then Eczema Preparation, then apply sealing/occlusive barrier cream, then wear gloves just prior to going to sleep.

Example 40

Conditioner

One or more formulation(s) in accordance with the invention are mixed with a conditioner base in a 3:1 ratio. A conditioner may comprise 1%-20% Roman/German/Moroccan essential oil by volume, and 1%-10% of Long-Acting Fraction (FGDE loaded biosilicates). An objective is to use it as a hair mask—lathering up but then letting it sit on the scalp to let the long-acting fraction soak into the scalp. The conditioner may soften and moisturize the scalp.

Example 41

Face/Scalp Mud Mask

The mask includes approximately 5%-70% of Long-Acting Fraction (FGDE loaded biosilicates) but may contain anywhere from 5×-30× more FGDE to ensure more loaded diatoms. The mask may be prepared as follows:
1) Add approximately 1%-20% Roman/German/Moroccan essential oil by volume as the last step for immediate onset
2) Use Eczema Preparation and Liquid Skin as the balance in 1:1.

The mask may be applied to face/scalp or other affected areas and allow to soak in for 30 minutes to 1 hour. Best used if resting under a near-infrared light to increase circulation and penetration (use of proper eye protection will be required).

Example 42

Face Wash

A face wash may comprise Liquid Skin with hyaluronic acid in a 1:1 ratio as a basic composition for a gentle cleanser, the basic composition may comprise between 10%-80% of the final product by volume. The face wash may include most, if not all, of components of Eczema Preparation(s) in the approximate percentages described above. The face wash does not include saponins and detergents, as they may worsens eczema.

Example 43

Mask Spray Formulations

A spray comprising one or more formulation(s) of the invention may be prepared. The spray may be sprayed on the outside of a 3-ply surgical face mask (which may be worn over an N95 or KN95 without affecting the integrity of the N95 or KN95 mask), or may be sprayed on a cloth mask, e.g., to help with nausea for pregnant ladies, or to improve the mask-wearing experience. The spray may also have an additional benefit(s) of decreasing anxiety, improving mood, attention, and decreasing appetite.

Example 44

Sweet Mint (SM1) Spray

SM1 may be prepared as follows:
1) In a 200 ml glass container mix 100 ml of organic Medium Chain Triglycerides (MCT) oil with 5 ml each of spearmint and peppermint essential oils. Mix well and aliquot into 5 ml glass spray vials. Spray 1-2 sprays on the outside of any cloth or any 3-ply surgical masks (do not spray on N95 or KN95 as oils degrade their ability to filter).

SM1 has a sweet, refreshing, spacious scent.

A 25-year-old pregnant healthcare worker in her first trimester with morning sickness had trouble tolerating wearing a mask at work for 8+ hours. She repeatedly removed her mask to retch. After 1-2 sprays of SM1 onto the outside of her 3-ply surgical mask she felt better and was able to tolerate uninterrupted wearing of the mask for the rest of her shift with less nausea.

Example 45

Fresh Mint (FM1) Spray

FM1 may be prepared as follows:
In a 200 ml glass container mix 100 ml of organic Medium Chain Triglycerides (MCT) oil with 5 ml of spearmint and 10 ml of peppermint essential oils. Mix well and aliquot into 5 ml glass spray vials.

FM1 has a sharply spacious refreshing scent and may be sprayed with a spray vial, a mechanical pump or an aerosolized pump (e.g., 1-2 sprays) on the outside of any cloth or 3-ply surgical mask as described above. The spray should not be sprayed on N95 or KN95 masks, as oils degrade their ability to filter.

Example 46

Lemonwood Spice (LWS1) Spray

LWS1 has a clean smelling, woodsy with citrus scent. LWS1 may be prepared as follows.
In a 500 ml glass container mix 400 ml of organic Medium Chain Triglycerides (MCT) oil with 5 ml of organic black pepper (*Piper nigrum*), 30 ml lemongrass, 15 ml of atlas cedarwood, and 15 ml cypress (Spain) essential oils. Mix well and aliquot into 5 ml glass spray vials.

LWS1 may be sprayed with a spray vial, a mechanical pump or an aerosolized pump (e.g., 1-2 sprays) on the outside of any cloth or 3-ply surgical masks. The spray should not be sprayed on N95 or KN95 masks, as oils degrade their ability to filter.

Example 47

Calm Focus (CFS1) Spray

CFS1 has a clean smelling, light citrus, mint, spice, and a sweet grass scent. CFS1 may be prepared as follows:

In a 500 ml glass container mix 100 ml of organic Medium Chain Triglycerides (MCT) oil with 5 ml each of bergamot mint and gingergrass essential oils, and 1 ml of bergamot essential oil. Mix well, aliquot into 5 ml glass spray vials.

CFS1 may be sprayed with a spray vial, a mechanical pump or an aerosolized pump (e.g., 1-2 sprays) on the outside of any cloth or a 3-ply surgical mask. The spray should not be sprayed on N95 or KN95 masks, as oils degrade their ability to filter.

Example 48

Instant Sunshine Spray (ISS1)

ISS1 has a bright, uplifting, minty fresh citrus scent that produces an instant sensation of contentment, and may be prepared as follows:

In a 500 ml glass container mix 100 ml of organic Medium Chain Triglycerides (MCT) oil with 14 ml of bergamot, 5 ml of spearmint, 9 ml of tangerine, and 2 ml cardamom essential oils. Mix well, aliquot into 5 ml glass spray vials.

ISS1 may be sprayed with a spray vial, a mechanical pump or an aerosolized pump (e.g., 1-2 sprays) on the outside of any cloth or a 3-ply surgical mask. The spray should not be sprayed on N95 or KN95 masks, as oils degrade their ability to filter.

Example 49

Pest/Insect Control Spray

Formulations of the invention may be used to prepare a pest/insect control spray. The spray may comprise, e.g., plant-based essential oils. The essential oils may be selected such that they disinfect on contact, have a pleasant smell, and have antimicrobial (e.g., antifungal, antiviral and antibacterial) properties. The formulation is non-toxic to mammals and possesses beneficial properties as described in Table 1 but are toxic to invertebrates due to significant differences in vertebrate versus invertebrate physiology and anatomy. In certain embodiments, the formulation may provide beneficial effect(s) to humans, e.g., by virtue disinfecting the air and/or in direct contact of the aerosolized spray with nasal mucosa and/or skin.

The formulation may inactivate insect neurologic systems by interfering with invertebrate cell membrane function, e.g., transport of nutrients and or air required for survival of an insect. The formulation may enter insect spiracules (breathing holes) and interfere with respiration in insects leading to their rapid demise. The formulation may be carried back to insect dwellings and additionally cause demise of eggs, larvae and juveniles.

FDGE technology may be used to provide a release of the formulation for an extended period of time. The formulations may comprise FDGE loaded with dead sea salts to form long-lasting microscopic crystals which extend release of volatile essential oils.

The formulations may be prepared as follows:
1) In a 4 L glass jar add 300 g of FDGE while wearing a mask and working in a well-ventilated area. Add 500 ml saturated dead sea salt solution and mix well.
2) Pour mixture into a 4 L glass container. Add 200 ml cinnamon essential oil (repels ants), 500 ml peppermint (repels spiders and flies), 500 ml orange essential oil (anti-microbial, repels mosquitoes, ants, flying and creeping insects), 500 ml white thyme essential oil (anti-microbial, insect repellant). Leave at room temperature overnight to load FDGE to create a saturated long-acting fraction. Then add balance up to 4 liters of isopropyl alcohol to create a concentrated solution. Mix well before aliquoting. Aliquot 50 ml of well-mixed concentrate into a 500 ml glass spray bottle, using isopropyl alcohol to bring up final volume to 500 ml. Mix well before spraying on surfaces (counters, floors, tile, etc.) and wiping dry to sanitize, deodorize, and to create a barrier that is repellent as well as toxic to insects but not to humans.

The formulation was tested and found effective against ants, cockroaches, pill bugs, mosquitoes, flies and earwigs; and may be effective against other unlisted insects.

The formulation may be used weekly, bi-weekly, every three weeks, or monthly depending on need.

Humans do not have spiracules and, consequently, should not be adversely affected by the use of the spray formulation.

Example 50

Scar/Keloid Formulation

PP4, PP5 or subsequent PP formulations may be combined in 1:1 ratio with AB1 to provide a formulation for treatment of scar/keloids. Psoriasis/Eczema, as well as AB1 formulations may also be used to treat scars/keloids.

The formulation was prepared and tested.

A young cancer patient with a surgical scar that she has had for several years applied the scar formulation and noted an improvement within 24 hours of the first application.

A 65-year-old female also used the formulation and noted improvement to a dark brown keloid scar she'd had for over 5 years. After application of the formulation, the keloid, which had initially measured approximately ¼×⅛"×¹⁄₁₆" and was dark brown, had visibly flattened and lightened in color. With every application the keloid was noted to become smaller and flatter.

Example 51

Hyperlipidemia/Non-Alcoholic Fatty Liver/Weight Loss Preparation (HLD/NASH/WL1)

HLD/NASH/WL1 may be prepared as follows:
1) Add 100 ml of kaffir lime leaf water extract to 200 ml galangal water extract, 200 ml ginger ethanolic extract, 100 ml lemongrass water extract, 100 ml extracts of fruit/bark/leaf from zanthoxylum armatum
2) While properly masked and in a ventilated space, add 300 g of FDGE to the water extract mixture and mix thoroughly.
3) Add 300 g each of resveratrol (grape seed extract) and grape skin extract and mix thoroughly.
4) Add 200 ml of emu oil 5) Add 20 ml of MNO+CO2 (macadamia nut oil+coconut oil stock)
6) Add 100 ml kaffir lime leaf essential oil, 400 ml blackseed essential oil (nigella sativa), 200 ml galangal essential oil, 200 ml ginger essential oil, 100 ml lemongrass essential oil, 50 ml zanthoxylum armatum essential oil and mix thoroughly.
7) Mix well.

HLD/NASH/WL1 may be taken in liquid form or as capsules, but may be formulated for injection, infusion, or introduced via other routes. It may be taken alone or as part of a comprehensive weight loss plan to normalize lipid metabolism.

Example 52

Alzheimer's Disease/Parkinson's Disease/Dementia/Neurodegeneration Formula 1

NDGNF1 may be prepared as follows:
1) While properly masked and in a ventilated space, add 300 g of FDGE to 550 ml of dead sea salt water in a 2 L glass jar with lid.
2) Add 500 g of grape seed extract (standardized to 95% proanthocyanidins) and mix well. Add 250 ml of sterile filtered water.
3) Add 500 g of grape skin extract (standardized to 95% polyphenols) and mix well. Add 250 ml of sterile filtered water.
4) Add 500 g of resveratrol (standardized to at least 8% potency yield) and mix well.
5) Mix well.
6) Add 1000 g lecithin and mix well.
7) Add 214 ml of MNO+CO2 (macadamia nut oil+coconut oil stock)
8) Add 2000 ml emu oil and mix well.
9) Make into gel capsules. Take 1 g to 4 g orally on a daily basis. To make into a nasal spray, substitute 1000 ml vegetable glycerin for lecithin, aliquot into dark glass nasal spray bottles, and spray each nostril 1-4 times daily to deposit active ingredients as close to the brain vasculature for rapid uptake. These formulations may be taken as part of a comprehensive neurorehabilitation, strength-, balance-, and cardiovascular-training program to improve brain function, prevent or slow progression of dementia, Alzheimer's Disease, Parkinson's Disease, and neurodegeneration.

Safety: It is believed that the preparations described herein are safe for use in all humans when used as directed in the age categories provided, with the exception of those who have documented allergic reaction to any of the ingredients; with exception of pregnant women who should avoid Alpinia galangal as it possesses abortifacient properties at high concentrations, and with exception of newborns with cardiac defects in which prostaglandin E2 is required to keep the ductus arteriosus open, since some components of chamomile extracts inhibit prostaglandin E2. Additionally, formulas containing wintergreen essential oil as an ingredient should generally be dosed according to guidelines listed in Table 1.

The formulations disclosed herein may be prepared on a commercial scale by the methods known in the art.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A formulation comprising:
   (i) a base composition comprising a lipid comprising fatty acids, and
   (ii) one or more additional ingredient(s) dispersed in the base composition, the additional ingredient(s) selected from a group consisting of a phospholipid, a ceramide, cholesterol, a fatty acid, an essential oil, a vitamin, a mineral, a therapeutic agent, an exosome, a bioactive ingredient, or a combination of two or more of any of the foregoing,
   wherein the fatty acids in the base composition are of a type and in amounts that render a fatty acid composition of the base composition substantially identical to a fatty acid composition of a cell membrane or a cell organelle or a sebum or an exosome of a mammalian cell, and
   the base composition comprises from about 30% to about 99% of the formulation by volume.

2. The formulation of claim 1, wherein the fatty acids are selected from a group consisting of myristic acid (C14:0), lauric acid (C12:0), palmitic acid (C16:0), arachidonic acid (C20:4 n-6), stearic acid (C18:0), oleic acid (C18:1 n-9), linoleic acid (C18:1 n-9), linoleic acid (C18-3 n-9), crotonic acid (C4H602), myristoleic acid, palmitoleic (C16:1) acid, sapienic acid (C16:1 n-10), oleic acid (C18:1 n-9), elaidic acid or trans-oleic acid (C18:1 n-9), vaccenic acid (C18:1 n-7), gadoleic acid (C20:1 n-11), eicosenoic acid (C20:1 n-9), erucic acid (C22:1 n-9) nervonic acid (C24:1 n-9), or a combination of two or more of any of the foregoing.

3. The formulation of claim 1, wherein the fatty acid composition of the base composition is substantially identical to a fatty acid composition of the cell membrane, and the mammalian cell is a human cell.

4. The formulation of claim 1, wherein the lipid is a mixture comprising coconut oil and macadamia nut oil.

5. The formulation of claim 4, wherein the mixture further comprises emu oil.

6. The formulation of claim 4, wherein the mixture further comprises high oleic sunflower seed oil.

7. The formulation of claim 4, wherein the mixture further comprises olive oil.

8. The formulation of claim 1, wherein the formulation comprises more than one additional ingredient.

9. The formulation of claim 8, wherein the formulation comprises a mixture of essential oils of German chamomile, Roman chamomile, and Moroccan chamomile, the mixture comprising from about 5% to about 30% of the formulation by volume.

10. The formulation of claim 1, wherein the lipid is coconut oil, the one or more additional ingredient(s) are selected from a group consisting of essential oils, and the base composition comprises from about 70% to about 99% of the formulation by volume.

11. The formulation of claim 1, wherein the one or more additional ingredient(s) are selected from a group consisting of essential oils.

12. The formulation of claim 11, wherein the base composition comprises from about 70% to about 99% of the formulation by volume.

13. The formulation of claim 12, wherein the lipid is an oil, and the oil selected from a group consisting of animal oils, vegetable oils and mixtures thereof.

14. The formulation of claim 11, wherein the fatty acids and essential oils are in an effective amount to reduce severity or alleviate pain.

15. A formulation comprising:
(i) a base composition comprising a lipid comprising fatty acids, and
(ii) one or more additional ingredient(s) dispersed in the base composition, the additional ingredient(s) selected from a group consisting of a phospholipid, a ceramide, cholesterol, a fatty acid, an essential oil, a vitamin, a mineral, a therapeutic agent, an exosome, a bioactive ingredient, or a combination of two or more of any of the foregoing,
wherein the fatty acids are in a ratio that allows the formulation to cross or integrate into a membrane of a cell, and
the base composition comprises from about 30% to about 99% of the formulation by volume.

16. The formulation of claim 15, wherein the one or more additional ingredient(s) are selected from a group consisting of essential oils.

17. The formulation of claim 16, wherein the base composition comprises from about 70% to about 99% of the formulation by volume.

18. The formulation of claim 17, wherein the lipid comprises an oil, and the oil selected from a group consisting of animal oils, vegetable oils and mixtures thereof.

19. The formulation of claim 15, which is a topical preparation.

20. The formulation of claim 19, which is a solution or an emulsion.

21. A formulation comprising:
(i) a base composition comprising a lipid comprising fatty acids, and
(ii) an essential oil dispersed in the base composition,
wherein the fatty acids in the base composition are of a type and in amounts that render a fatty acid composition of the base composition substantially identical to a fatty acid composition of a cell membrane or a cell organelle or a sebum or an exosome of a mammalian cell, and
the base composition comprises from about 30% to about 99% of the formulation by volume.

22. The formulation of claim 21, wherein the fatty acid composition of the base composition is substantially identical to a fatty acid composition of the cell membrane, and the mammalian cell is a human cell.

23. The formulation of claim 22, wherein the formulation further comprises a phospholipid, a ceramide, cholesterol, a fatty acid, a vitamin, a mineral, a therapeutic agent, an exosome, a bioactive ingredient, or a combination of two or more of any of the foregoing.

24. The formulation of claim 23, wherein the lipid is an oil, and the oil selected from a group consisting of animal oils, vegetable oils and mixtures thereof.

25. The formulation of claim 24, wherein the lipid is a mixture comprising coconut oil and macadamia nut oil.

26. The formulation of claim 21, wherein the lipid comprises palmitic acid, stearic acid, oleic acid, and linoleic acid.

27. The formulation of claim 1, wherein the lipid comprises palmitic acid, stearic acid, oleic acid, and linoleic acid.

* * * * *